US008846676B2

(12) United States Patent
Almario Garcia et al.

(10) Patent No.: US 8,846,676 B2
(45) Date of Patent: Sep. 30, 2014

(54) 6-CYCLOAMINO-3-(PYRID-4-YL)IMIDAZO[1,2-B]PYRIDAZINE DERIVATIVES, PREPARATION THEREOF AND THERAPEUTIC USE THEREOF

(75) Inventors: Antonio Almario Garcia, Paris (FR); Mathieu Barrague, Bridgewater, NJ (US); Philippe Burnier, Maisons-Laffitte (FR); Cecile Enguehard-Gueiffier, Tours (FR); Zhongli Gao, Flemington, NJ (US); Pascal George, Longvilliers (FR); Alain Gueiffier, Tours (FR); Adrien Tak Li, Fontenay Aux Roses (FR); Frederic Peuch, Gif sur Yvette (FR); Roy Vaz, Branchburg, NJ (US); Qiuxia Zhao, Green Brook, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/617,678

(22) Filed: Sep. 14, 2012

(65) Prior Publication Data

US 2013/0012516 A1 Jan. 10, 2013

Related U.S. Application Data

(60) Division of application No. 12/647,059, filed on Dec. 24, 2009, now Pat. No. 8,354,405, which is a continuation of application No. PCT/FR2008/000902, filed on Jun. 26, 2008.

(60) Provisional application No. 60/946,785, filed on Jun. 28, 2007.

(30) Foreign Application Priority Data

Jun. 28, 2007 (FR) ...................... 07 04661

(51) Int. Cl.
*A01N 43/58* (2006.01)
*A01N 43/60* (2006.01)
*A61K 31/50* (2006.01)
*A61K 31/495* (2006.01)
*C07D 487/04* (2006.01)

(52) U.S. Cl.
CPC .................... *C07D 487/04* (2013.01)
USPC .......................... 514/248; 544/236

(58) Field of Classification Search
USPC .......................... 514/248; 544/236
See application file for complete search history.

(56) References Cited

U.S. PATENT DOCUMENTS

| 7,402,672 | B2 | 7/2008 | Metz et al. |
| 7,820,670 | B2 * | 10/2010 | Chen et al. ............... 514/252.06 |
| 2009/0176788 | A1 | 7/2009 | Falco et al. |
| 2010/0227861 | A1 | 9/2010 | Bearss et al. |

FOREIGN PATENT DOCUMENTS

| EP | 1790650 | 5/2007 |
| WO | 02/066481 | 8/2002 |
| WO | 2004/016614 | 2/2004 |
| WO | 2006/070943 | 7/2006 |
| WO | 2007/013673 | 2/2007 |

OTHER PUBLICATIONS

Bryant, et al., Psychopharmacology (Berl), May 2009; 203(4): 703-711.*
Nievergelt, et al., Am. J. Med. Genetics Part B (Neuropsychiatric Genetics) 141B:234-241 (2006).*
C. McClung, 21 European Neuropsychopharmacology, S683-S693, S685 (2011).*
K.M. Walton et al., 330 The Journal of Pharmacology and Experimental Therapeutics, 430-439 (2009).*
Abignente., E., et al., Research on Heterocyclic Compounds. XX. Synthesis of Trifluoromethyl Derivatives of Fused Imidazole Systems, J. Heterocyclic Chem., vol. 23, (1986), pp. 1031-1034.
Hervet, M., et al., Reactivity of 2-Substited Imidazo[1,2-b]Pyridazines: Preparation of 3-Nitro, Nitroso and Chloro Derivatives, J. Heterocyclic Chem., vol. 39, pp. 737-742, (2002).
Ishikawa, T., et al., Studies on Anti-MRSA Parenteral Cephalosporins, The Journal of Antibiotics, vol. 53, No. 10, (2000), pp. 1053-1070.
Jurgee, M., et al., Pyridazines, LXX. Reactions of Azidoazolopyridazines with Unsaturated Compounds, J. Heterocyclic Chem., vol. 12, (1975), pp. 253-255.

(Continued)

*Primary Examiner* — James O Wilson
*Assistant Examiner* — Alexander R Pagano
(74) *Attorney, Agent, or Firm* — Scully, Scott, Murphy & Presser, P.C.

(57) ABSTRACT

The invention relates to the 6-cycloamino-3-(pyridin-4-yl) imidazo[I,2-b]pyridazine derivatives corresponding to general formula (I):

(I)

Wherein $R_2$, $R_3$, $R_7$, $R_8$, A, L and B are as defined herein. Also disclosed are the preparative methods and therapeutic use thereof.

19 Claims, No Drawings

(56) References Cited

OTHER PUBLICATIONS

Mavel, S., et al., Synthesis of Imidazo[2,1-a]phthaizaines, Potential Inhibitors of p38 MAP Kinase, Prediction of Binding Afinities of Protein Ligands, Archiv der Pharmazie, vol. 335, No. 1, pp. 7-14, (2002).
Mourad, A.E., et al., Synthesis of Imidazol[1,2-b]Pyridazines: Fenbendazole, Oxifenbendazole Analogs and Related Derivatives. J. Heterocyclic Chem., vol. 30, pp. 1365-1372, (1993).
Pollak, A., et al., Synthesis of Pyridazine Derivatives—XVI Methyl Substituted Imidazo(1,2-b)Pyridazines By Synthesis and Homolytic Methylation. Tetrahedron, vol. 24, pp. 2626-2629, (1968).
Watanabe, M. et al., Peripheral Conjugate System; Part 2, Synthesis of Diimidazo[1,2-b]Pyridazine, Synthesis, pp. 761, (1977).
Werbel, L. M., et al., Synthesis of Fused Imidazo-Heterocyclic Systems, J. Heterocyclic Chem., vol. 2, pp. 287-290, (1965).
Yoneda, F., et al., Pyridazin-Derivate. VI. Synthese der Derivate des imidazo[1,2-b]Pyridazins., Chem. Pharm. Bill., vol. 12, No. 11, pp. 1351-1356, (1964).
Allada, R., et al., "A Mutant Drosophila Homolog of Mammalian Clock Disrupts Circadian Rhythms and Transcription of period and timeless", Cell, 93:791-804 (1998).
Badura, L., et al., "An Inhibitor of Casein Kinase Iε Induces Phase Delays in Circadian Rhythms under Free-Running and Entrained Conditions", The Journal of Pharmacology and Experimental Therapeutics, 322 (2):730-738 (2007).
Benedetti, F., et al., "Morning Light Treatment Hastens the Antidepressant Effect of Citalopram: A Placebo-Controlled Trial", J Clin Psychiatry, 64:648-653 (2003).
Camacho, F., et al., "Human casein kinase Iδ phosphorylation of human circadian clock proteins period 1 and 2", FEBS Letters, 489:159-165 (2001).
Crosthwaite, S., et al., "Neurospora wc-1 and wc-2: Transcription, Photoresponses, and the Origins of Circadian Rhythmicity", Science, 276:763-769 (1997).
Dunlap, J., "Genetic and Molecular Analysis of Circadian Rhythms", Annu. Rev. Genet, 30:579-601 (1996).
Dunlap, J., "Molecular Bases for Circadian Clocks", Cell, 96:271-290 (1999).
Etchegaray, J., et al., "Casein Kinase 1 Delta Regulates the Pace of the Mammalian Circadian Clock", Molecular and Cellular Biology, 29(14):3853-3866 (2009).
Hall, J., "Are Cycling Gene Products as Internal Zeitgebers No Longer the Zeitgeist of Chronobiology?", Neuron, 17:979-990 (1996) the document is pp. 799-802.
Hastings, M., "Central clocking", Trends Neurosci., 20:459-464 (1997).
Keesler, G., et al., "Phosphorylation and destabilization of human period 1 clock protein by human casein kinase Iε", Neuroreport, 11(57):951-955 (2000).
Kloss, B. et al., "The Drosophila Clock Gene double-time Encodes a Protein Closely Related to Human Casein Kinase Iε", Cell, 94:97-107 (1998).
Konda, T., et al., "Circadian Clock Mutants of Cyanobacteria", Science, 266:1233-1236 (1994).
Kripke, D., "Light treatment for nonseasonal depression: speed, efficacy, and combined treatment", Journal of Affective Disorders, 49:109-117 (1998).
Lalli, E., et al., "Orphan Receptor DAX-1 Is a Shuttling RNA Binding Protein Associated with Polyribosomes via mRNA", Molecular and Cellular Biology, 20(13):4910-4921 (2000).
Lowrey, P., et al., "Positional Syntenic Cloning and Functional Characterization of the Mammalian Circadian Mutation tau", Science, 288-483-491 (2000).
McCall, WV, "A psychiatric perspective on insomnia", J Clin Psychiatry, 62(Suppl 10):27-32 (2001) Abstract Only.
Price, J., et al., "double-time Is a Novel *Drosophila* Clock Gene that Regulates PERIOD Protein Accumulation", Cell, 94:83-95 (1998).
Ralph, M., et al., "A Mutation of the Circadian System in Golden Hamsters", Science, 241:1225-1227 (1988).
Reppert, S., et al., "Forward Genetic Approach Strikes Gold: Cloning of a Mammalian Clock Gene", Cell, 89:487-490 (1997).
Shearman, L., et al., "Two period Homologs: Circadian Expression and Photic Regulation in the Suprachiasmatic Nuclei", Neuron, 19:1261-1269 (1997).
Spengler, C., et al., "An endogenous circadian rhythm of respiratory control in humans", Journal of Physiology, 526 (3):683-694 (2000).
Takano, A., et al., "Cloning and characterization of rat casein kinase 1ε", FEBS Letters, 477:106-112 (2000).
Tam, EM, et al., Treatment of seasonal affective disorder: a review.:, Can J Psychiatry 40(8):457-466 (1995), Abstract Only.
Terman, J., et al., "Circadian Time of Morning Light Administration and Therapeutic Response in Winter Depression", Arch Gen Psychiatry, 58:69-75 (2001).
Thase, ME, "Antidepressant teratment of the depressed patient with insomnia.", J Clin Psychiatry, 60(Suppl 17):28-31 (1999) Abstract Only.
Vielhaber, E., et al., "Nuclear Entry of the Circadian Regulator mPER1 Is Controlled by Mammalian Casein Kinase Iε" Molecular and Cellular Biology, 20(13):4888-4899 (2000).

* cited by examiner

6-CYCLOAMINO-3-(PYRID-4-YL)IMIDAZO[1,2-B]PYRIDAZINE DERIVATIVES, PREPARATION THEREOF AND THERAPEUTIC USE THEREOF

This application is a divisional application of application U.S. patent application Ser. No. 12/647,059, filed Dec. 24, 2009, which is a continuation of International application No. PCT/FR2008/000,902, filed Jun. 26, 2008, which claims the benefit of U.S. Provisional Application No. 60/946,785, filed Jun. 28, 2007, and the benefit of priority of French patent application Ser. No. 07/04,661, filed Jun. 28, 2007. The contents of each of the aforementioned applications are incorporated by reference.

The present invention relates to 6-cycloamino-3-(pyrid-4-yl)imidazo[1,2-b]pyridazine derivatives, to a process for preparing them and to their therapeutic use, in the treatment or prevention of diseases involving casein kinase 1 epsilon and/or casein kinase 1 delta.

One subject of the present invention is compounds corresponding to the general formula (I)

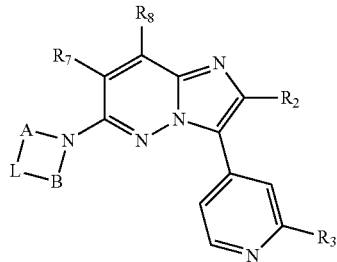

in which
R$_2$ represents an aryl group optionally substituted with one or more substituents chosen from halogen atoms and the groups C$_{1-6}$ alkyl, C$_{1-6}$ alkyloxy, C$_{1-6}$ alkylthio, C$_{1-6}$ fluoroalkyl, C$_{1-6}$-fluoroalkyloxy and —CN;
R$_3$ represents a hydrogen atom or a group C$_{1-3}$ alkyl, —NR$_4$R$_6$, hydroxyl or C$_{1-4}$ alkyloxy;
A represents a group C$_{1-7}$-alkylene optionally substituted with one or two groups R$_a$;
B represents a group C$_{1-7}$-alkylene optionally substituted with a group R$_b$;
L represents either a nitrogen atom optionally substituted with a group R$_c$ or R$_d$, or a carbon atom substituted with a group R$_{e1}$ and a group R$_d$ or two groups R$_{e2}$;
the carbon atoms of A and B being optionally substituted with one or more groups R$_f$, which may be identical to or different than each other;
R$_a$, R$_b$ and R$_c$ are defined such that:
two groups R$_a$ may together form a group C$_{1-6}$-alkylene;
R$_a$ and R$_b$ may together form a bond or a group C$_{1-6}$-alkylene;
R$_a$ and R$_c$ may together form a bond or a group C$_{1-6}$-alkylene;
R$_b$ and R$_c$ may together form a bond or a group C$_{1-6}$-alkylene;
R$_d$ represents a group chosen from a hydrogen atom and the groups C$_{1-6}$-alkyl, C$_{3-7}$-cycloalkyl, C$_{3-7}$-cycloalkyl-C$_{1-6}$-alkyl, C$_{1-6}$-alkylthio-C$_{1-6}$-alkyl, C$_{1-6}$-alkyloxy-C$_{1-6}$-alkyl, C$_{1-6}$-fluoroalkyl, benzyl, C$_{1-6}$-acyl and hydroxy-C$_{1-6}$-alkyl;
R$_{e1}$ represents a group —NR$_4$R$_5$ or a cyclic monoamine optionally comprising an oxygen atom, the cyclic monoamine being optionally substituted with one or more substituents chosen from a fluorine atom and the groups C$_{1-6}$-alkyl, C$_{1-6}$-alkyloxy and hydroxyl;
two groups R$_{e2}$ form, with the carbon atom that bears them, a cyclic monoamine optionally comprising an oxygen atom, this cyclic monoamine being optionally substituted with one or more groups R$_f$, which may be identical to or different than each other;
R$_f$ represents a group C$_{1-6}$-alkyl, C$_{3-7}$-cycloalkyl, C$_{1-6}$-alkyloxy-C$_{1-6}$-alkyl, hydroxy-C$_{1-6}$-alkyl, C$_{1-6}$-fluoroalkyl or benzyl;
R$_4$ and R$_5$ represent, independently of each other, a hydrogen atom or a group C$_{1-4}$ alkyl, C$_{3-7}$-cycloalkyl or C$_{3-7}$-cycloalkyl-C$_{1-6}$-alkyl;
R$_7$ and R$_8$ represent, independently of each other, a hydrogen atom or a group C$_{1-6}$-alkyl.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may also exist in the form of hydrates or solvates, i.e. in the form of associations or combinations with one or more water molecules or with a solvent. Such hydrates and solvates also form part of the invention.

In the context of the invention, the following definitions apply:
C$_{t-z}$ in which t and z may take values from 1 to 7: a carbon-based chain possibly containing from t to z carbon atoms, for example C$_{1-7}$ is a carbon-based chain that may contain from 1 to 7 carbon atoms;
alkyl: a linear or branched, saturated aliphatic group; for example a group C$_{1-6}$-alkyl represents a linear or branched carbon-based chain of 1 to 6 carbon atoms, for example a methyl, ethyl, propyl, isopropyl, butyl, isobutyl, tert-butyl, pentyl or hexyl;
alkylene: a linear or branched, saturated divalent alkyl group, for example a group C$_{1-6}$-alkylene represents a linear or branched divalent carbon-based chain of 1 to 6 carbon atoms, for example a methylene, ethylene, 1-methylethylene or propylene;
cycloalkyl: a cyclic alkyl group, for example a group C$_{3-7}$-cycloalkyl represents a cyclic carbon-based group of 3 to 7 carbon atoms, for example a cyclopropyl, cyclobutyl, cyclopentyl, cyclohexyl or cycloheptyl;
acyl: a group alkyl-C(O)—;
hydroxyl: a group —OH;
cyclic monoamine: a saturated cyclic carbon-based chain comprising 1 nitrogen atom;
hydroxyalkyl: an alkyl group in which a hydrogen atom has been replaced with a hydroxyl group;
alkyloxy: a group —O-alkyl;
alkylthio: a group —S-alkyl;
fluoroalkyl: an alkyl group in which one or more hydrogen atoms have been replaced with a fluorine atom;
fluoroalkyloxy: an alkyloxy group in which one or more hydrogen atoms have been replaced with a fluorine atom;
a halogen atom: a fluorine, chlorine, bromine or iodine atom;
aryl: a monocyclic or bicyclic aromatic group containing between 6 and 10 carbon atoms. Examples of aryl groups that may be mentioned include phenyl and naphthyl groups.

As nonlimiting examples of cyclic amines or diamines formed by N, A, L and B, mention may be made especially of aziridine, azetidine, pyrrolidine, piperidine, azepine, morpholine, thiomorpholine, homopiperidine, decahydroquinoline, decahydroisoquinoline, azabicycloheptane, azabicyclooctane, azabicyclononane, azaoxobicycloheptane, azathiabicycloheptane, azaoxobicyclooctane, azathiabicyclooctane; piperazine, homopiperazine, diazacyclooctane, diazacyclononane, diazacyclodecane, diazacycloundecane, octahydropyrrolopyrazine, octahydropyrrolodiazepine, octahydropyrrolopyrrole, octahydropyrrolopyridine, decahydronaphthyridine, diazabicycloheptane, diazabicyclooctane, diazabicyclononane, diazaspiroheptane, diazaspirooctane, diazaspirononane, diazaspirodecane, diazaspiroundecane and oxadiazaspiroundecane.

Among the compounds of general formula (I) that are subjects of the invention, a first group of compounds is constituted by the compounds for which $R_2$ represents a phenyl group optionally substituted with one or more substituents chosen from halogen atoms and the groups $C_{1-6}$ alkyl, $C_{1-6}$ alkyloxy and $C_{1-6}$ fluoroalkyl;

$R_3$, A, L, B, $R_7$ and $R_8$ being as defined above.

Among the compounds of general formula (I) that are subjects of the invention, a second group of compounds is constituted by the compounds for which $R_2$ represents a phenyl group optionally substituted with one or more substituents chosen from fluorine and chlorine atoms and methyl, methoxy and trifluoromethyl groups;

$R_3$, A, L, B, $R_7$ and $R_8$ being as defined above.

Among the compounds of general formula (I) that are subjects of the invention, a third group of compounds is constituted by the compounds for which $R_3$ represents a group chosen from a hydrogen atom and a group $C_{1-3}$ alkyl, $C_{1-4}$ alkyloxy or —$NR_4R_5$; $R_4$ and $R_5$ represent a hydrogen atom or a group $C_{1-4}$-alkyl;

$R_2$, A, L, B, $R_7$ and $R_8$ being as defined above.

Among the compounds of general formula (I) that are subjects of the invention, a fourth group of compounds is constituted by the compounds for which $R_3$ represents a group chosen from a hydrogen atom and a methyl or methoxy group;

$R_2$, A, L, B, $R_7$ and $R_8$ being as defined above.

Among the compounds of general formula (I) that are subjects of the invention, a fifth group of compounds is constituted by the compounds for which $R_3$ represents a group chosen from —$NH_2$, methylamino and dimethylamino;

$R_2$, A, L, B, $R_7$ and $R_8$ being as defined above.

Among the compounds of general formula (I) that are subjects of the invention, a sixth group of compounds is constituted by the compounds for which $R_3$ represents a group chosen from —$NH_2$ and dimethylamino;

$R_2$, A, L, B, $R_7$ and $R_8$ being as defined above.

Among the compounds of general formula (I) that are subjects of the invention, a seventh group of compounds is constituted by the compounds for which $R_7$ and $R_8$ represent, independently of each other, a hydrogen atom or a methyl group;

$R_2$, $R_3$, A, L, B, being as defined above.

Among the compounds of general formula (I) that are subjects of the invention, an eighth group of compounds is constituted by the compounds for which:

A represents a group $C_{1-7}$-alkylene;
B represents a group $C_{1-7}$-alkylene;
L represents a carbon atom substituted with a group $R_{e1}$ and a group $R_d$;
$R_d$ represents a hydrogen atom;
$R_{e1}$ represents a group $NR_4R_5$, in which $R_4$ and $R_5$ independently represent a group $C_{1-4}$-alkyl; or alternatively $R_{e1}$ represents a cyclic monoamine optionally comprising an oxygen atom, the monoamine being optionally substituted with one or more groups chosen from a fluorine atom and the groups hydroxyl and $C_{1-6}$-alkyl;

$R_2$, $R_3$, $R_7$ and $R_8$ being as defined above.

Among the compounds of general formula (I) that are subjects of the invention, a ninth group of compounds is constituted by the compounds for which:

A represents a group —$C_2H_4$—;
B represents a group —$C_2H_4$— or —$CH_2$—;
L represents a carbon atom substituted with a group $R_{e1}$ and a group $R_d$;
$R_d$ represents a hydrogen atom;
$R_{e1}$ represents a group chosen from the groups dimethylamino, pyrrolidinyl, morpholinyl, dimethylmorpholinyl, fluoropyrrolidinyl, hydroxypyrrolidinyl;

$R_2$, $R_3$, $R_7$ and $R_8$ being as defined above.

Among the compounds of general formula (I) that are subjects of the invention, a tenth group of compounds is constituted by the compounds for which:

the cyclic amine formed by —N-A-L-B— represents a (±)-3-dimethylaminopyrrolidin-1-yl, 4-(pyrrolidin-1-yl)piperid-1-yl, 4-(morpholin-4-yl)piperid-1-yl, 4-(2,6-dimethylmorpholin-4-yl)piperid-1-yl, 4-dimethylaminopiperid-1-yl, 4-((R)-3-fluoropyrrolidin-1-yl)piperid-1-yl or 4-(3-hydroxypyrrolidin-1-yl)piperid-1-yl;

$R_2$, $R_3$, $R_7$ and $R_8$ being as defined above.

Among the compounds of general formula (I) that are subjects of the invention, an eleventh group of compounds is constituted by the compounds for which:

A represents a group $C_{1-7}$-alkylene;
B represents a group $C_{1-7}$-alkylene;
L represents a carbon atom substituted with a group $R_{e1}$ and a group $R_d$;
$R_d$ represents a hydrogen atom;
$R_{e1}$ represents a group $NR_4R_5$, in which $R_4$ and $R_5$ represent, independently of each other, a group $C_{1-4}$-alkyl; or alternatively $R_{e1}$ represents a cyclic monoamine optionally comprising an oxygen atom, the monoamine being optionally substituted with one or more groups chosen from the groups hydroxyl and $C_{1-6}$-alkyl;

$R_2$, $R_3$, $R_7$ and $R_8$ being as defined above.

Among the compounds of general formula (I) that are subjects of the invention, a twelfth group of compounds is constituted by the compounds for which:

A represents a group —$C_2H_4$—;
B represents a group —$C_2H_4$— or —$CH_2$—;
L represents a carbon atom substituted with a group $R_{e1}$ and a group $R_d$;
$R_d$ represents a hydrogen atom;
$R_{e1}$ represents a group chosen from dimethylamino, pyrrolidinyl, morpholinyl, dimethylmorpholinyl and hydroxypyrrolidinyl groups;

$R_2$, $R_3$, $R_7$ and $R_8$ being as defined above.

Among the compounds of general formula (I) that are subjects of the invention, a thirteenth group of compounds is constituted by the compounds for which:

the cyclic amine formed by —N-A-L-B— represents a (±)-3-dimethylaminopyrrolidin-1-yl, (pyrrolidin-1-yl)piperid-1-yl, 4-(morpholin-4-yl)piperid-1-yl, 4-(2,6-dimethylmorpholin-4-yl)-piperid-1-yl, 4-dimethylaminopiperid-1-yl or 4-(3-hydroxypyrrolidin-1-yl)piperid-1-yl;

$R_2$, $R_3$, $R_7$ and $R_8$ being as defined above.

Among the compounds of general formula (I) that are subjects of the invention, a fourteenth group of compounds is constituted by the compounds for which:

A represents a group $C_{1-7}$-alkylene optionally substituted with one or two groups $R_a$;

B represents a group $C_{1-7}$-alkylene optionally substituted with a group $R_b$;

L represents a nitrogen atom optionally substituted with a group $R_c$ or $R_d$; the carbon atoms of A and B being optionally substituted with one or more groups $R_f$, which may be identical to or different than each other;

two groups $R_a$ may together form a group $C_{1-6}$-alkylene;

$R_a$ and $R_b$ may together form a bond or a group $C_{1-6}$-alkylene;

$R_a$ and $R_c$ may together form a bond or a group $C_{1-6}$-alkylene;

$R_b$ and $R_c$ may together form a bond or a group $C_{1-6}$-alkylene;

$R_d$ represents a substituent chosen from a group $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkyl, $C_{1-6}$-fluoroalkyl, benzyl or $C_{1-6}$-acyl;

$R_f$ represents a group $C_{1-6}$-alkyl; hydroxy-$C_{1-6}$-alkyl or fluoro-$C_{1-6}$-alkyl $R_2$, $R_3$, $R_7$ and $R_8$ being as defined above.

Among the compounds of general formula (I) that are subjects of the invention, a fifteenth group of compounds is constituted by the compounds for which:

the cyclic amine formed by —N-A-L-B— represents a piperazinyl, a diazepanyl, hexahydropyrrolopyrazinyl, diazabicycloheptyl, octahydropyrrolodiazepinyl, diazabicyclononyl, hexahydropyrrolopyrrolyl, octahydropyrrolopyridinyl, decahydronaphthyridinyl or diazaspirodecyl, optionally substituted with one or more groups chosen from methyl, ethyl, isopropyl, butyl, cyclopropyl, cyclohexyl, hydroxymethyl, hydroxyethyl, (hydroxymethyl)propyl, (hydroxymethyl)butyl, methoxyethyl, fluoromethyl, fluoroethyl, trifluoroethyl, acetyl, isobutyryl and benzyl groups;

$R_2$, $R_3$, $R_7$ and $R_8$ being as defined above.

Among the compounds of general formula (I) that are subjects of the invention, a sixteenth group of compounds is constituted by the compounds for which:

the cyclic amine formed by —N-A-L-B— represents a piperazin-1-yl, 3-methylpiperazin-1-yl, 4-methylpiperazin-1-yl, 3,3-dimethylpiperazin-1-yl, 3,4-dimethylpiperazin-1-yl, cis-3,5-dimethylpiperazin-1-yl, 4-(2-hydroxyethyl)piperazin-1-yl, 4-(2-methoxyethyl)piperazin-1-yl, 4-(2-fluoroethyl)piperazin-1-yl, 4-(2,2,2-trifluoroethyl)piperazin-1-yl, 4-cyclopropylpiperazin-1-yl, 4-isopropylpiperazin-1-yl, 4-(2-hydroxy-2-methylpropyl)piperazin-1-yl, 4-n-butylpiperazin-1-yl, 4-(3-hydroxy-3-methylbutyl)piperazin-1-yl, cyclohexylpiperazin-1-yl, 4-acetylpiperazin-1-yl, 4-isobutyrylpiperazin-1-yl, (±)-hexahydropyrrolo[1,2-a]pyrazin-2-yl, (S)-hexahydropyrrolo[1,2-a]pyrazin-2-yl, (1S,4S)-2,5-diazabicyclo[2.2.1]hept-2-yl, 1(S,4S)-5-benzyl-2,5-diazabicyclo[2.2.1]hept-2-yl, (1S,4S)-5-(2-hydroxyethyl)-2,5-diazabicyclo[2.2.1]hept-2-yl, 5-isopropyl-2,5-diaza[2.2.1]hept-2-yl, 4-methyl-[1,4]diazepan-1-yl, (±)-octahydropyrrolo[1,2-d][1,4]diazepin-3-yl, 1,4-diazabicyclo[3.3.2]non-4-yl, (±)-3,6-diazabicyclo[3.2.0]hept-3-yl, hexahydropyrrolo[3,4-b]pyrrol-5(1H)-yl, hexahydropyrrolo[3,4-c]pyrrol-2(1H)-yl, 5-benzylhexahydropyrrolo[3,4-c]pyrrol-2(1H)-yl, 5-cyclopropylhexahydropyrrolo[3,4-c]pyrrol-2(1H)-yl, 5-isopropylhexahydropyrrolo[3,4-c]pyrrol-2(1H)-yl, octahydro-6H-pyrrolo[3,4-b]pyrid-6-yl, (±)-(cis)-decahydro[2,6]-naphthyridin-2-yl, 3-ethylpiperazin-1-yl, 3,3-diethylpiperazin-1-yl, 3-fluoromethylpiperazin-1-yl, 4-(3-hydroxymethyl)piperazin-1-yl, 3-(1-hydroxy-1-methylethyl)piperazin-1-yl, 3-isopropylpiperazin-1-yl, (1R,5R)-3,6-diazabicyclo[3.2.0]hept-2-yl, 5-methyl-2,5-diazabicyclo[2.2.1]hept-2-yl, 1-((1S,4S)-(2,5-diazabicyclo[2.2.1]hept-2-yl)-2-methylpropan-2-ol, 3,6-diazabicyclo[3.1.1]hept-3-yl, 5-methylhexahydropyrrolo[3,4-c]pyrrol-2(1H)-yl, (±)-hexahydropyrrolo[3,4-b]pyrrol-5(1H)-yl, (+)-hexahydropyrrolo[3,4-b]pyrrol-5(1H)-yl, (−)-hexahydropyrrolo[3,4-b]pyrrol-5(1H)-yl, (4aS,7aS)-octahydropyrrolo[3,4-b]pyrid-6-yl or 6,9-diazaspiro[4.5]dec-9-yl;

$R_2$, $R_3$, $R_7$ and $R_8$ being as defined above.

Among the compounds of general formula (I) that are subjects of the invention, a seventeenth group of compounds is constituted by the compounds for which:

A represents a group $C_{1-7}$-alkylene optionally substituted with one or two groups $R_a$;

B represents a group $C_{1-7}$-alkylene optionally substituted with a group $R_b$;

L represents a nitrogen atom optionally substituted with a group $R_c$ or $R_d$; the carbon atoms of A and B being optionally substituted with one or more identical or different groups $R_f$;

$R_a$ and $R_b$ may together form a bond or a group $C_{1-6}$-alkylene;

$R_a$ and $R_c$ may together form a bond or a group $C_{1-6}$-alkylene;

$R_b$ and $R_c$ may together form a bond or a group $C_{1-6}$-alkylene;

$R_d$ represents a substituent chosen from the groups $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkyl, $C_{1-6}$-fluoroalkyl, benzyl and $C_{1-6}$-acyl;

$R_f$ represents a group $C_{1-6}$-alkyl;

$R_2$, $R_3$, $R_7$ and $R_8$ being as defined above.

Among the compounds of general formula (I) that are subjects of the invention, an eighteenth group of compounds is constituted by the compounds for which:

the cyclic amine formed by —N-A-L-B— represents a piperazinyl, a diazepanyl, hexahydropyrrolopyrazinyl, diazabicycloheptyl, octahydropyrrolodiazepinyl, diazabicyclononyl, hexahydropyrrolopyrrolyl, octahydropyrrolopyridinyl or decahydronaphthyridinyl, optionally substituted with one or more groups chosen from methyl, ethyl, isopropyl, butyl, cyclopropyl, cyclohexyl, hydroxyethyl, (hydroxymethyl)propyl, (hydroxymethyl)butyl, methoxyethyl, fluoroethyl, trifluoroethyl, acetyl, isobutyryl and benzyl groups;

$R_2$, $R_3$, $R_7$ and $R_8$ being as defined above.

Among the compounds of general formula (I) that are subjects of the invention, a nineteenth group of compounds is constituted by the compounds for which:

the cyclic amine formed by —N-A-L-B— represents a piperazin-1-yl, 3-methylpiperazin-1-yl, 4-methylpiperazin-1-yl, 3,3-dimethylpiperazin1-yl, 3,4-dimethylpiperazin-1-yl, cis-3,5-dimethylpiperazin-1-yl, 4-(2-hydroxyethyl)piperazin-1-yl, 4-(2-methoxyethyl)piperazin-1-yl, 4-(2-fluoroethyl)piperazin-1-yl, 4-(2,2,2-trifluoroethyl)piperazin-1-yl, 4-cyclopropylpiperazin-1-yl, 4-isopropylpiperazin-1-yl, 4-(2-hydroxy-2-methylpropyl)piperazin-1-yl, 4-n-butylpiperazin-1-yl, 4-(3-hydroxy-3-methylbutyl)piperazin-1-yl, cyclohexylpiperazin-1-yl, 4-acetylpiperazin-1-yl, 4-isobutyrylpiperazin-1-yl, (±)-hexahydropyrrolo[1,2-a]pyrazin-2-yl, (S)-hexahydropyrrolo[1,3-a]pyrazin-2-yl, (1S,4S)-2,5-diazabicyclo[2.2.1]hept-2-yl, 1(S,4S)-5-benzyl-2,5-diazabicyclo-[2.2.1]hept-2-yl, (1S,4S)-5-(2-hydroxyethyl)-2,5-diazabicyclo[2.2.1]hept-2-yl, 5-isopropyl-2,5-diaza[2.2.1]hept-2-yl, 4-methyl[1,4]diazepan-1-yl, (±)-octahydropyrrolo[1,2-d][1,4]diazepin-3-yl, 1,4-diazabicyclo[3.3.2]non-4-yl, (±)-3,6-diazabicyclo[3.2.0]hept-3-yl, hexahydropyrrolo[3,4-b]pyrrol-5(1H)-yl, hexahydropyrrolo[3,4-c]pyrrol-2(1H)-yl, 5-benzylhexahydropyrrolo[3,4-c]-pyrrol-2(1H)-yl, 5-cyclopropylhexahydropyrrolo[3,4-c]pyrrol-2(1H)-yl, 5-isopropylhexahydropyrrolo[3,4-c]pyrrol-2(1H)-yl, octahydro-6H-pyrrolo[3,4-b]pyrid-6-yl or (±)-(cis)-decahydro-[2,6]naphthyridin-2-yl;

$R_2$, $R_3$, $R_7$ and $R_8$ being as defined above.

Among the compounds of general formula (I) that are subjects of the invention, a twentieth group of compounds is constituted by the compounds for which:

A represents a group $C_{1-7}$-alkylene;
B represents a group $C_{1-7}$-alkylene;
L represents a carbon atom substituted with two groups $R_{e2}$;
the carbon atoms of A and B being optionally substituted with one or more groups $R_f$, which may be identical to or different than each other;
  two groups $R_{e2}$ form, with the carbon atom that bears them, a pyrrolidine, piperidine or morpholine group;
$R_f$ represents a group $C_{1-6}$-alkyl;
$R_2$, $R_3$, $R_7$ and $R_8$ being as defined above.

Among the compounds of general formula (I) that are subjects of the invention, a twenty-first group of compounds is constituted by the compounds for which:
the cyclic amine formed by —N-A-L-B— represents a diazaspirononyl, diazaspirodecyl, diazaspiroundecyl or oxadiazaspiroundecyl;
$R_2$, $R_3$, $R_7$ and $R_8$ being as defined above.

Among the compounds of general formula (I) that are subjects of the invention, a twenty-second group of compounds is constituted by the compounds for which:
the cyclic amine formed by —N-A-L-B— represents a (±)-2,7-diazaspiro[4.4]non-2-yl, (±)-2,8-diazaspiro[4.5]dec-2-yl, (±)-2,7-diazaspiro[4.5]dec-2-yl, (±)-2,8-diazaspiro[4.5]dec-8-yl, (±)-2,7-diazaspiro[4.5]dec-7-yl, 3,9-diazaspiro[5.5]undec-3-yl, 2,9-diazaspiro[5.5]undec-9-yl, (±)-2,8-diazaspiro[5.5]undec-2-yl or 1-oxa-4,9-diazaspiro[5.5]undec-9-yl;
$R_2$, $R_3$, $R_7$ and $R_8$ being as defined above.

Among the compounds of general formula (I) that are subjects of the invention, a twenty-third group of compounds is constituted by the compounds for which:
$R_2$ represents a phenyl group optionally substituted with one or more substituents chosen from fluorine and chlorine atoms and a methyl group;
$R_3$ represents a hydrogen atom;
the cyclic amine formed by —N-A-L-B— represents a (±)-3-dimethylaminopyrrolidin-1-yl, 4-(pyrrolidin-1-yl)piperid-1-yl, 4-(morpholin-4-yl)piperid-1-yl, 4-(2,6-dimethylmorpholin-4-yl)piperid-1-yl, 4-dimethylaminopiperid-1-yl, 4-(3-hydroxypyrrolidin-1-yl)piperid-1-yl or 4-(3-fluoropyrrolidin-1-yl)piperid-1-yl;
$R_7$ and $R_8$ represent a hydrogen atom.

Among the compounds of general formula (I) that are subjects of the invention, a twenty-fourth group of compounds is constituted by the compounds for which:

$R_2$ represents a phenyl group optionally substituted with one or more substituents chosen from fluorine and chlorine atoms and methyl, methoxy and trifluoromethyl groups;
$R_3$ represents a hydrogen atom or a methyl, methoxy, —NH$_2$, methylamino, or dimethylamino group;
the cyclic amine formed by —N-A-L-B— represents a piperazin-1-yl, 3-methylpiperazin-1-yl, 4-methylpiperazin-1-yl, 3,3-dimethylpiperazin1-yl, 3,4-dimethylpiperazin-1-yl, cis-3,5-dimethylpiperazin-1-yl, 4-(2-hydroxyethyl)piperazin-1-yl, 4-(2-methoxyethyl)piperazin-1-yl, 4-(2-fluoroethyl)piperazin-1-yl, 4-(2,2,2-trifluoroethyl)piperazin-1-yl, 4-cyclopropylpiperazin-1-yl, 4-isopropylpiperazin-1-yl, 4-(2-hydroxy-2-methylpropyl)piperazin-1-yl, 4-n-butylpiperazin-1-yl, 4-(3-hydroxy-3-methylbutyl)piperazin-1-yl, cyclohexylpiperazin-1-yl, 4-acetylpiperazin-1-yl, 4-isobutyrylpiperazin-1-yl, (±)-hexahydropyrrolo[1,2-a]pyrazin-2-yl, (S)-hexahydropyrrolo[1,2-a]pyrazin-2-yl, (1S,4S)-2,5-diazabicyclo[2.2.1]hept-2-yl, 1(S,4S)-5-benzyl-2,5-diazabicyclo[2.2.1]hept-2-yl, (1S,4S)-5-(2-hydroxyethyl)-2,5-diazabicyclo[2.2.1]hept-2-yl, 5-isopropyl-2,5-diaza[2.2.1]hept-2-yl, 4-methyl-[1,4]diazepan-1-yl, (±)-octahydropyrrolo[1,2-d][1,4]diazepin-3-yl, 1,4-diazabicyclo[3.3.2]non-4-yl, (±)-3,6-diazabicyclo[3.2.0]hept-3-yl, hexahydropyrrolo[3,4-b]pyrrol-5(1H)-yl, hexahydropyrrolo[3,4-c]pyrrol-2(1H)-yl, 5-benzylhexahydropyrrolo[3,4-c]pyrrol-2(1H)-yl, 5-cyclopropylhexahydropyrrolo[3,4-c]pyrrol-2(1H)-yl, 5-isopropylhexahydropyrrolo[3,4-c]pyrrol-2(1H)-yl, octahydro-6H-pyrrolo[3,4-b]pyrid-6-yl, (±)-(cis)-decahydro[2,6]-naphthyridin-2-yl, 3-ethylpiperazin-1-yl, 3,3-diethylpiperazin-1-yl, 3-fluoromethylpiperazin-1-yl, 4-(3-hydroxymethyl)piperazin-1-yl, 3-(1-hydroxy-1-methylethyl)piperazin-1-yl, 3-isopropylpiperazin-1-yl, (1R,5R)-3,6-diazabicyclo[3.2.0]hept-2-yl, 5-methyl-2,5-diazabicyclo[2.2.1]hept-2-yl, 1-((1S,4S)-(2,5-diazabicyclo[2.2.1]hept-2-yl)-2-methylpropan-2-ol, 3,6-diazabicyclo[3.1.1]hept-3-yl, 5-methylhexahydropyrrolo[3,4-c]pyrrol-2(1H)-yl, (±)-hexahydropyrrolo[3,4-b]pyrrol-5(1H)-yl, (+)-hexahydropyrrolo[3,4-b]pyrrol-5(1H)-yl, (−)-hexahydropyrrolo[3,4-b]pyrrol-5(1H)-yl, (4aS,7aS)-octahydropyrrolo[3,4-b]pyrid-6-yl or 6,9-diazaspiro[4.5]dec-9-yl;

$R_7$ and $R_8$ independently represent a hydrogen atom or a methyl group.

Among the compounds of general formula (I) that are subjects of the invention, a twenty-fifth group of compounds is constituted by the compounds for which:
$R_2$ represents a phenyl group optionally substituted with one or more substituents chosen from fluorine and chlorine atoms;
$R_3$ represents a hydrogen atom;
the cyclic amine formed by —N-A-L-B— represents a (±)-3-dimethylaminopyrrolidin-1-yl, 4-(pyrrolidin-1-yl)piperid-1-yl, 4-(morpholin-4-yl)piperid-1-yl, 4-(2,6-dimethylmorpholin-4-yl)piperid-1-yl, 4-dimethylaminopiperid-1-yl or 4-(3-hydroxypyrrolidin-1-yl)piperid-1-yl;
$R_7$ and $R_8$ represent a hydrogen atom.

Among the compounds of general formula (I) that are subjects of the invention, a twenty-sixth group of compounds is constituted by the compounds for which:

R₂ represents a phenyl group optionally substituted with one or more substituents chosen from fluorine and chlorine atoms and methyl, methoxy and trifluoromethyl groups;

R₃ represents a hydrogen atom or a methyl, methoxy, —NH₂ or dimethylamino group;

the cyclic amine formed by —N-A-L-B— represents a piperazin-1-yl, 3-methylpiperazin-1-yl, 4-methylpiperazin-1-yl, 3,3-dimethylpiperazin1-yl, 3,4-dimethylpiperazin-1-yl, cis-3,5-dimethylpiperazin-1-yl, 4-(2-hydroxyethyl)piperazin-1-yl, 4-(2-methoxyethyl)piperazin-1-yl, 4-(2-fluoroethyl)piperazin-1-yl, 4-(2,2,2-trifluoroethyl)piperazin-1-yl, 4-cyclopropylpiperazin-1-yl, 4-isopropylpiperazin-1-yl, 4-(2-hydroxy-2-methylpropyl)piperazin-1-yl, 4-n-butylpiperazin-1-yl, 4-(3-hydroxy-3-methylbutyl)piperazin-1-yl, 4-cyclohexylpiperazin-1-yl, 4-acetylpiperazin-1-yl, 4-isobutyrylpiperazin-1-yl, (±)-3,6-diazabicyclo[3.2.0]hept-3-yl, (±)-hexahydropyrrolo[1,2-a]pyrazin-2-yl, (S)-hexahydropyrrolo[1,2-a]pyrazin-2-yl, (1S,4S)-2,5-diazabicyclo[2.2.1]hept-2-yl, (1S,4S)-5-benzyl-2,5-diazabicyclo[2.2.1]hept-2-yl, 5-isopropyl-2,5-diaza[2.2.1]hept-2-yl, 4-methyl[1,4]diazepan-1-yl, (±)-octahydropyrrolo[1,2-d][1,4]diazepin-2-yl, 1,4-diazabicyclo-[3.3.2]non-4-yl, hexahydropyrrolo[3,4-b]pyrrol-5(1H)-yl, hexahydropyrrolo[3,4-c]pyrrol-2(1H-yl, 5-benzylhexahydropyrrolo[3,4-c]pyrrol-2(1H)-yl, 5-cyclopropylhexahydropyrrolo[3,4-c]-pyrrol-2(1H)-yl, 5-isopropylhexahydropyrrolo[3,4-c]pyrrol-2(1H)-yl, octahydro-6H-pyrrolo[3,4-b]pyrid-6-yl or (±)-(cis)-decahydro[2,6]naphthyridin-2-yl;

R₇ and R₈ represent, independently of each other, a hydrogen atom or a methyl group.

Among the compounds of general formula (I) that are subjects of the invention, a twenty-seventh group of compounds is constituted by the compounds for which:

R₂ represents a phenyl group optionally substituted with one or more substituents chosen from fluorine and chlorine atoms;

R₃ represents a hydrogen atom or a methyl, methoxy or —NH₂ group;

the cyclic amine formed by —N-A-L-B— represents (±)-2,7-diazaspiro[4.4]non-2-yl, (±)-2,8-diazaspiro[4.5]dec-2-yl, (±)-2,7-diazaspiro[4.5]dec-2-yl, (±)-2,8-diazaspiro[4.5]dec-8-yl, (±)-2,7-diazaspiro[4.5]dec-7-yl, 3,9-diazaspiro[5.5]undec-3-yl, 2,9-diazaspiro[5.5]undec-9-yl, (±)-2,8-diazaspiro[4.5]undec-2-yl or 1-oxa-4,9-diazaspiro[5.5]undec-9-yl;

R₇ and R₈ represent a hydrogen atom.

Among the compounds of general formula (I) that are subjects of the invention, mention may be made especially of the following compounds:

2-Phenyl-6-piperazin-1-yl-3-pyrid-4-ylimidazo[1,2-b]pyridazine;

2-(4-Fluorophenyl)-6-piperazin-1-yl-3-pyrid-4-ylimidazo[1,2-b]pyridazine;

2-(4-Fluorophenyl)-7,8-dimethyl-6-piperazin-1-yl-3-pyrid-4-ylimidazo[1,2-b]pyridazine;

4-[2-(4-Fluorophenyl)-6-piperazin-1-ylimidazo[1,2-b]pyridazin-3-yl]pyrid-2-ylamine;

2-(4-Fluorophenyl)-3-(2-methoxypyrid-4-yl)-6-piperazin-1-ylimidazo[1,2-b]pyridazine;

2-(4-Chlorophenyl)-6-piperazin-1-yl-3-pyrid-4-ylimidazo[1,2-b]pyridazine;

2-(4-Chlorophenyl)-7-methyl-6-piperazin-1-yl-3-pyrid-4-ylimidazo[1,2-b]pyridazine;

2-(4-Chlorophenyl)-8-methyl-6-piperazin-1-yl-3-pyrid-4-ylimidazo[1,2-b]pyridazine;

2-(3,5-Dimethylphenyl)-6-piperazin-1-yl-3-pyrid-4-ylimidazo[1,2-b]pyridazine;

2-(3,5-Difluorophenyl)-6-piperazin-1-yl-3-pyrid-4-ylimidazo[1,2-b]pyridazine;

2-(3,5-Difluorophenyl)-3-(2-methylpyrid-4-yl)-6-piperazin-1-ylimidazo[1,2-b]pyridazine;

2-(3,4-Difluorophenyl)-6-piperazin-1-yl-3-pyrid-4-ylimidazo[1,2-b]pyridazine;

2-(3,5-Dichlorophenyl)-6-piperazin-1-yl-3-pyrid-4-ylimidazo[1,2-b]pyridazine;

2-(3,5-Dichlorophenyl)-3-(2-methylpyrid-4-yl)-6-piperazin-1-ylimidazo[1,2-b]pyridazine;

(±)-6-(3-Methylpiperazin-1-yl)-2-phenyl-3-pyrid-4-ylimidazo[1,2-b]pyridazine;

6-((R)-3-Methylpiperazin-1-yl)-2-phenyl-3-pyrid-4-ylimidazo[1,2-b]pyridazine;

6-((R)-3-Methylpiperazin-1-yl)-3-(2-methylpyrid-4-yl)-2-phenylimidazo[1,2-b]pyridazine;

6-((S)-3-Methylpiperazin-1-yl)-2-phenyl-3-pyrid-4-ylimidazo[1,2-b]pyridazine;

2-(3-Fluorophenyl)-6-(R)-3-methylpiperazin-1-yl)-3-pyrid-4-ylimidazo[1,2-b]pyridazine;

2-(4-Fluorophenyl)-6-(3-methylpiperazin-1-yl)-3-pyrid-4-ylimidazo[1,2-b]pyridazine;

2-(4-Fluorophenyl)-6-(R)-3-methylpiperazin-1-yl)-3-pyrid-4-ylimidazo[1,2-b]pyridazine;

2-(4-Fluorophenyl)-6-(S)-3-methylpiperazin-1-yl)-3-pyrid-4-ylimidazo[1,2-b]pyridazine;

2-(4-Fluorophenyl)-3-(2-methoxypyrid-4-yl)-6-(R)-3-methylpiperazin-1-yl)imidazo[1,2-b]pyridazine;

2-(3,4-Difluorophenyl)-6-((R)-3-methylpiperazin-1-yl)-3-pyrid-4-ylimidazo[1,2-b]pyridazine;

6-(3,3-Dimethylpiperazin-1-yl)-2-phenyl-3-pyrid-4-ylimidazo[1,2-b]pyridazine;

6-(3,3-Dimethylpiperazin-1-yl)-2-(4-fluorophenyl)-3-pyrid-4-ylimidazo[1,2-b]pyridazine;

6-(3,3-Dimethylpiperazin-1-yl)-2-(4-fluorophenyl)-3-(2-methoxypyrid-4-yl)imidazo[1,2-b]pyridazine;

2-(3,5-Dimethylphenyl)-6-(3,3-dimethylpiperazin-1-yl)-3-pyrid-4-ylimidazo[1,2-b]pyridazine;

2-(3,5-Dimethylphenyl)-6-(3,3-dimethylpiperazin-1-yl)-3-(2-methylpyrid-4-yl)imidazo[1,2-b]pyridazine;

4-[2-(3,5-Dimethylphenyl)-6-(3,3-dimethylpiperazin-1-yl)imidazo[1,2-b]pyridazin-3-yl]pyrid-2-ylamine;

2-(3,5-Difluorophenyl)-6-(3,3-dimethylpiperazin-1-yl)-3-pyrid-4-ylimidazo[1,2-b]pyridazine;

2-(3,5-Difluorophenyl)-6-(3,3-dimethylpiperazin-1-yl)-3-(2-methylpyrid-4-yl)imidazo[1,2-b]pyridazine;

4-[2-(3,5-Difluorophenyl)-6-(3,3-dimethylpiperazin-1-yl)imidazo[1,2-b]pyridazin-3-yl]pyrid-2-ylamine;

2-(3,5-Dichlorophenyl)-6-(3,3-dimethylpiperazin-1-yl)-3-pyrid-4-ylimidazo[1,2-b]pyridazine;

2-(3,5-Dichlorophenyl)-6-(3,3-dimethylpiperazin-1-yl)-3-(2-methylpyrid-4-yl)imidazo[1,2-b]pyridazine;

(±)-6-(3,4-Dimethylpiperazin-1-yl)-2-(4-fluorophenyl)-3-pyrid-4-ylimidazo[1,2-b]pyridazine;

6-((cis)-3,5-Dimethylpiperazin-1-yl)-2-phenyl-3-pyrid-4-ylimidazo[1,2-b]pyridazine;

6-((cis)-3,5-Dimethylpiperazin-1-yl)-3-(2-methylpyrid-4-yl)-2-phenylimidazo[1,2-b]pyridazine;

6-((cis)-3,5-Dimethylpiperazin-1-yl)-2-(3-fluorophenyl)-3-pyrid-4-ylimidazo[1,2-b]pyridazine;

6-((cis)3,5-Dimethylpiperazin-1-yl)-2-(4-fluorophenyl)-3-pyrid-4-ylimidazo[1,2-b]pyridazine;

6-((cis)-3,5-Dimethylpiperazin-1-yl)-2-(4-fluorophenyl)-3-(2-methoxypyrid-4-yl)imidazo[1,2-b]pyridazine;
2-(3,5-Dimethylphenyl)-6-((cis)-3,5-dimethylpiperazin-1-yl)-3-pyrid-4-ylimidazo[1,2-b]pyridazine;
2-(3,4-Difluorophenyl)-6-((cis)-3,5-dimethylpiperazin-1-yl)-3-pyrid-4-ylimidazo[1,2-b]pyridazine;
2-(4-Chlorophenyl)-6-((cis)-3,5-dimethylpiperazin-1-yl)-7-methyl-3-pyrid-4-ylimidazo[1,2-b]pyridazine;
6-((cis)-3,5-Dimethylpiperazin-1-yl)-2-(4-fluorophenyl)-8-methyl-3-pyrid-4-ylimidazo[1,2-b]pyridazine;
2-(2-Chlorophenyl)-6-(4-methylpiperazin-1-yl)-3-pyrid-4-ylimidazo[1,2-b]pyridazine;
2-(3-Chlorophenyl)-6-(4-methylpiperazin-1-yl)-3-pyrid-4-ylimidazo[1,2-b]pyridazine;
2-(4-Chlorophenyl)-6-(4-methylpiperazin-1-yl)-3-pyrid-4-ylimidazo[1,2-b]pyridazine;
2-(3-Fluorophenyl)-6-(4-methylpiperazin-1-yl)-3-pyrid-4-ylimidazo[1,2-b]pyridazine;
2-(4-Fluorophenyl)-6-(4-methylpiperazin-1-yl)-3-pyrid-4-ylimidazo[1,2-b]pyridazine;
2-(3,4-Difluorophenyl)-6-(4-methylpiperazin-1-yl)-3-pyrid-4-ylimidazo[1,2-b]pyridazine;
2-(3-Methoxyphenyl)-6-(4-methylpiperazin-1-yl)-3-pyrid-4-ylimidazo[1,2-b]pyridazine;
2-(4-Methoxyphenyl)-6-(4-methylpiperazin-1-yl)-3-pyrid-4-ylimidazo[1,2-b]pyridazine;
6-(4-Methylpiperazin-1-yl)-3-pyrid-4-yl-2-p-tolylimidazo[1,2-b]pyridazine;
6-(4-Methylpiperazin-1-yl)-3-pyrid-4-yl-2-(4-trifluoromethylphenyl)imidazo[1,2-b]pyridazine;
2-(4-Fluorophenyl)-6-(4-methylpiperazin-1-yl)-3-(2-methylpyrid-4-yl)imidazo[1,2-b]pyridazine;
4-[2-(4-Fluorophenyl)-6-(4-methylpiperazin-1-yl)imidazo[1,2-b]pyridazin-3-yl]pyrid-2-ylamine;
{4-[2-(4-Fluorophenyl)-6-(4-methylpiperazin-1-ypimidazo[1,2-b]pyridazin-3-yl]pyrid-2-yl}-dimethylamine;
2-(4-Fluorophenyl)-3-(2-methoxypyrid-4-yl)-6-(4-methylpiperazin-1-yl)imidazo[1,2-b]pyridazine;
6-(4-Ethylpiperazin-1-yl)-2-(4-fluorophenyl)-3-pyrid-4-ylimidazo[1,2-b]pyridazine;
2-(3,5-Dimethylphenyl)-6-(4-ethylpiperazin-1-yl)-3-pyrid-4-ylimidazo[1,2-b]pyridazine;
2-[4-(2-Phenyl-3-pyrid-4-ylimidazo[1,2-b]pyridazin-6-yl)piperazin-1-yl]ethanol;
2-{4-[2-(3-Fluorophenyl)-3-pyrid-4-ylimidazo[1,2-b]pyridazin-6-yl]piperazin-1-yl}ethanol;
2-{4-[2-(4-Fluorophenyl)-3-pyrid-4-ylimidazo[1,2-b]pyridazin-6-yl]piperazin-1-yl}ethanol;
2-{4-[2-(4-Fluorophenyl)-3-(2-methoxypyrid-4-yl)imidazo[1,2-b]pyridazin-6-yl]piperazin-1-yl}ethanol;
2-{4-[2-(3,4-Difluorophenyl)-3-pyrid-4-ylimidazo[1,2-b]pyridazin-6-yl]piperazin-1-yl}ethanol;
2-{4-[2-(4-Chlorophenyl)-3-pyrid-4-ylimidazo[1,2-b]pyridazin-6-yl]piperazin-1-yl}ethanol;
2-{4-[3-(2-Aminopyrid-4-yl)-2-(4-chlorophenyl)imidazo[1,2-b]pyridazin-6-yl]piperazin-1-yl}ethanol;
2-(4-Chlorophenyl)-6-[4-(2-methoxyethyl)piperazin-1-yl]-3-pyrid-4-ylimidazo[1,2-b]pyridazine;
6-[4-(2-Fluoroethyl)piperazin-1-yl]-2-(4-fluorophenyl)-3-pyrid-4-ylimidazo[1,2-b]pyridazine;
6-[4-(2-Fluoroethyl)piperazin-1-yl]-2-(4-fluorophenyl)-3-(2-methoxypyrid-4-yl)imidazo[1,2-b]pyridazine;
2-Phenyl-3-pyrid-4-yl-6-[4-(2,2,2-trifluoroethyl)piperazin-1-yl]imidazo[1,2-b]pyridazine;
2-(4-Fluorophenyl)-3-pyrid-4-yl-6-[4-(2,2,2-trifluoroethyl)piperazin-1-yl]imidazo[1,2-b]pyridazine;
6-(4-Cyclopropylpiperazin-1-yl)-2-(4-fluorophenyl)-3-pyrid-4-ylimidazo[1,2-b]pyridazine;
6-(4-Cyclopropylpiperazin-1-yl)-2-(4-fluorophenyl)-3-(2-methoxypyrid-4-yl)imidazo[1,2-b]pyridazine;
6-(4-Isopropylpiperazin-1-yl)-3-(2-methoxpyrid-4-yl)-2-phenylimidazo[1,2-b]pyridazine;
2-(3-Fluorophenyl)-6-(4-isopropylpiperazin-1-yl)-3-pyrid-4-ylimidazo[1,2-b]pyridazine;
2-(4-Fluorophenyl)-6-(4-isopropylpiperazin-1-yl)-3-pyrid-4-ylimidazo[1,2-b]pyridazine;
2-(4-Fluorophenyl)-6-(4-isopropylpiperazin-1-yl)-3-(2-methoxypyrid-4-yl)imidazo[1,2-b]pyridazine;
2-(3,4-Difluorophenyl)-6-(4-isopropylpiperazin-1-yl)-3-pyrid-4-ylimidazo[1,2-b]pyridazine;
4-[2-(4-Chlorophenyl)-6-(4-isopropylpiperazin-1-yl)imidazo[1,2-b]pyridazin-3-yl]pyrid-2-ylamine;
2-Methyl-1-[4-(2-phenyl-3-pyrid-4-ylimidazo[1,2-b]pyridazin-6-yl)piperazin-1-yl]propan-2-ol;
1-{4-[2-(3-Fluorophenyl)-3-pyrid-4-ylimidazo[1,2-b]pyridazin-6-yl]piperazin-1-yl}-2-methylpropan-2-ol;
1-{4-[2-(4-Fluorophenyl)-3-(2-methoxypyrid-4-yl)imidazo[1,2-b]pyridazin-6-yl]piperazin-1-yl}-2-methylpropan-2-ol;
6-(4-Butylpiperazin-1-yl)-2-(4-chlorophenyl)-3-pyrid-4-ylimidazo[1,2-b]pyridazine;
4-{4-[2-(4-Fluorophenyl)-3-(2-methoxypyrid-4-yl)imidazo[1,2-b]pyridazin-6-yl]piperazin-1-yl}-2-methylbutan-2-ol;
6-(4-Cyclohexylpiperazin-1-yl)-2-(4-fluorophenyl)-3-pyrid-4-ylimidazo[1,2-b]pyridazine;
1-{-4-[2-(4-Fluorophenyl)-3-pyrid-4-ylimidazo[1,2-b]pyridazin-6-yl]piperazin-1-yl}ethanone;
1-{4-[2-(4-Fluorophenyl)-3-pyrid-4-ylimidazo[1,2-b]pyridazin-6-yl]piperazin-1-yl}-2-methylpropan-1-one;
(±)-2-(4-Fluorophenyl)-6-(hexahydropyrrolo[1,2-a]pyrazin-2-yl)-3-pyrid-4-ylimidazo[1,2-b]pyridazine;
2-(4-Fluorophenyl)-6-(S)-hexahydropyrrolo[1,2-a]pyrazin-2-yl-3-(2-methoxypyrid-4-yl)-imidazo[1,2-b]pyridazine;
6-((1S,4S)-2,5-Diazabicyclo[2.2.1]hept-2-yl)-2-phenyl-3-pyrid-4-ylimidazo[1,2-b]pyridazine;
6-((1S,4S)-5-Benzyl-2,5-diazabicyclo[2.2.1]hept-2-yl)-2-(3-fluorophenyl)-3-pyrid-4-ylimidazo[1,2-b]pyridazine;
6-((1S,4S)-2,5-Diazabicyclo[2.2.1]hept-2-yl)-2-(4-fluorophenyl)-3-pyrid-4-ylimidazo[1,2-b]pyridazine;
6-((1S,4S)-5-Benzyl-2,5-diazabicyclo[2.2.1]hept-2-yl)-2-(4-fluorophenyl)-3-pyrid-4-ylimidazo[1,2-b]pyridazine;
6-((1S,4S)-2,5-Diazabicyclo[2.2.1]hept-2-yl)-2-(4-fluorophenyl)-3-(2-methoxypyrid-4-yl)imidazo[1,2-b]pyridazine;
2-{(1S,4S)-5-[2-(4-Fluorophenyl)-3-(2-methoxypyrid-4-yl)imidazo[1,2-b]pyridazin-6-yl]-2,5-diazabicyclo[2.2.1]hept-2-yl}ethanol;
2-(4-Fluorophenyl)-6-(5-isopropyl-2,5-diazabicyclo[2.2.1]hept-2-yl)-3-(2-methoxypyrid-4-yl)imidazo[1,2-b]pyridazine;
2-(4-Fluorophenyl)-6-(4-methyl[1,4]diazepan-1-yl)-3-pyrid-4-ylimidazo[1,2-b]pyridazine;
(±)-3-[2-(4-Fluorophenyl)-3-pyrid-4-ylimidazo[1,2-b]pyridazin-6-yl]octahydro(1H)pyrrolo[1,2-d][1,4]diazepine;
(±)-4-[2-(4-Fluorophenyl)-3-pyrid-4-ylimidazo[1,2-b]pyridazin-6-yl]-1,4-diazabicyclo[3.2.2]nonane;
(±)-4-[2-(3,5-Dimethylphenyl)-3-pyrid-4-ylimidazo[1,2-b]pyridazin-6-yl]-1,4-diazabicyclo[3.2.2]nonane;
(±)-3,6-diazabicyclo[3.2.0]hept-3-yl-2-phenyl-3-pyrid-4-ylimidazo[1,2-b]pyridazine;
(±)-6-(Hexahydropyrrolo[3,4-b]pyrrol-5(1H)-yl)-2-phenyl-3-pyrid-4-ylimidazo[1,2-b]pyridazine;

(±)-6-(Hexahydropyrrolo[3,4-b]pyrrol-5(1H)-yl)-3-(2-methylpyrid-4-yl)-2-phenylimidazo[1,2-b]pyridazine;
6-Hexahydropyrrolo[3,4-c]pyrrol-2(1H)-yl-2-phenyl-3-pyrid-4-ylimidazo[1,2-b]pyridazine;
6-Hexahydropyrrolo[3,4-c]pyrrol-2(1H)-yl-3-(2-methylpyrid-4-yl)-2-phenylimidazo[1,2-b]pyridazine;
2-(3-Fluorophenyl)-6-hexahydropyrrolo[3,4-c]pyrrol-2(1H)-yl-3-(2-methylpyrid-4-yl)imidazo[1,2-b]pyridazine;
2-(4-Fluorophenyl)-6-hexahydropyrrolo[3,4-c]pyrrol-2(1H)-yl-3-pyrid-4-ylimidazo[1,2-b]pyridazine;
2-(4-Fluorophenyl)-6-hexahydropyrrolo[3,4-c]pyrrol-2(1H)-yl-3-(2-methylpyrid-4-yl)imidazo[1,2-b]pyridazine;
4-[2-(4-Chlorophenyl)-6-(hexahydropyrrolo[3,4-c]pyrrol-2(1H)-yl)imidazo[1,2-b]pyridazin-3-yl]pyrid-2-ylamine;
2-(4-Fluorophenyl)-6-(hexahydropyrrolo[3,4-c]pyrrol-2(1H)-yl)-3-(2-methoxypyrid-4-yl)-imidazo[1,2-b]pyridazine;
4-[6-(5-Benzylhexahydropyrrolo[3,4-c]pyrrol-2(1H)-yl)-7,8-dimethyl-2-(4-fluorophenyl)imidazo[1,2-b]pyridazin-3-yl]pyrid-2-ylamine;
4-[2-(4-Fluorophenyl)-6-hexahydropyrrolo[3,4-c]pyrrol-2(1H)-yl-7,8-dimethylimidazo[1,2-b]pyridazin-3-yl]pyrid-2-ylamine;
6-(5-Cyclopropylhexahydropyrrolo[3,4-c]pyrrol-2(1H)-yl)-2-(4-fluorophenyl)-3-pyrid-4-ylimidazo[1,2-b]pyridazine;
2-(4-Fluorophenyl)-6-(5-isopropylhexahydropyrrolo[3,4-c]pyrrol-2(1H)-yl)-3-pyrid-4-ylimidazo[1,2-b]pyridazine;
2-(4-Fluorophenyl)-6-(5-isopropylhexahydropyrrolo[3,4-c]pyrrol-2-(1H)-yl)-3-(2-methylpyrid-4-yl)imidazo[1,2-b]pyridazine;
2-(4-Fluorophenyl)-6-(5-isopropylhexahydropyrrolo[3,4-c]pyrrol-2(1H)-yl)-3-(2-methoxpyrid-4-yl)imidazo[1,2-b]pyridazine
(±)-6-(Octahydro-6H-pyrrolo[3,4-b]pyrid-6-yl)-2-phenyl-3-pyrid-4-ylimidazo[1,2-b]pyridazine;
(±)-3-(2-Methylpyrid-4-yl)-6-(octahydro-6H-pyrrolo[3,4-b]pyrid-6-yl)-2-phenylimidazo[1,2-b]pyridazine;
(±)-(cis)-2-[2-(4-Fluorophenyl)-3-pyrid-4-ylimidazo[1,2-b]pyridazin-6-yl]decahydro[2,6]-naphthyridine;
(±)-6-(2,7-Diazaspiro[4.4]non-2-yl)-2-(3-fluorophenyl)-3-pyrid-4-ylimidazo[1,2-b]pyridazine;
(±)-6-(2,7-Diazaspiro[4.4]non-2-yl)-2-(4-fluorophenyl)-3-pyrid-4-ylimidazo[1,2-b]pyridazine;
(±)-6-(2,8-Diazaspiro[4.5]dec-2-yl)-2-(4-fluorophenyl)-3-pyrid-4-ylimidazo[1,2-b]pyridazine;
(±)-6-(2,7-Diazaspiro[4.5]dec-2-yl)-2-(4-fluorophenyl)-3-pyrid-4-ylimidazo[1,2-b]pyridazine;
(±)-6-(2,8-Diazaspiro[4.5]dec-8-yl)-2-(4-fluorophenyl)-3-pyrid-4-ylimidazo[1,2-b]pyridazine;
(±)-6-(2,7-Diazaspiro[4.5]dec-7-yl)-2-(4-fluorophenyl)-3-pyrid-4-ylimidazo[1,2-b]pyridazine;
3-[2-(4-Fluorophenyl)-3-pyrid-4-ylimidazo[1,2-b]pyridazin-6-yl]-3,9-diazaspiro[5.5]undecane;
9-(2-Phenyl-3-pyrid-4-ylimidazo[1,2-b]pyridazin-6-yl)-2,9-diazaspiro[5.5]undecane;
9-[3-(2-Methylpyrid-4-yl)-2-phenylimidazo[1,2-b]pyridazin-6-yl]-2,9-diazaspiro[5.5]undecane;
9-[2-(3-Fluorophenyl)-3-(2-methylpyrid-4-yl)imidazo[1,2-b]pyridazin-6-yl]-2,9-diazaspiro[5.5]-undecane;
9-[2-(4-Fluorophenyl)-3-pyrid-4-ylimidazo[1,2-b]pyridazin-6-yl]-2,9-diazaspiro[5.5]undecane;
9-[2-(4-Fluorophenyl)-3-(2-methylpyrid-4-yl)imidazo[1,2-b]pyridazin-6-yl]-2,9-diazaspiro[5.5]-undecane;
4-[2-(4-Chlorophenyl)-6-(2,9-diazaspiro[5.5]undec-9-yl)imidazo[1,2-b]pyridazin-3-yl]pyrid-2-ylamine;
9-[2-(4-Fluorophenyl)-3-(2-methoxypyrid-4-yl)imidazo[1,2-b]pyridazin-6-yl]-2,9-diazaspiro-[5.5]undecane;
2-[2-(4-Fluorophenyl)-3-(pyrid-4-yl)imidazo[1,2-b]pyridazin-6-yl]-2,9-diazaspiro[5.5]undecane
2-[2-(4-Fluorophenyl)-3-(pyrid-4-yl)imidazo[1,2-b]pyridazin-6-yl]-2,8-diazaspiro[5.5]undecane
9-[2-(phenyl)-3-(pyrid-4-yl)imidazo[1,2-b]pyridazin-6-0]-1-oxa-4,9-diazaspiro[5.5]undecane;
9-[2-(4-Fluorophenyl)-3-(pyrid-4-yl)imidazo[1,2-b]pyridazin-6-yl]-1-oxa-4,9-diazaspiro[5.5]-undecane;
9-[2-(4-Fluorophenyl)-3-(2-methoxypyrid-4-yl)imidazo[1,2-b]pyridazin-6-yl]-1-oxa-4,9-diazaspiro[5.5]undecane;
4-{[2-(4-Chlorophenyl)-3-(2-methoxypyrid-4-yl)imidazo[1,2-b]pyridazin-6-yl]-1-oxa-4,9-diazaspiro[5.5]undec-9-yl}-2-ylamine;
(±)-{1-[2-(4-Fluorophenyl)-3-pyrid-4-ylimidazo[1,2-b]pyridazin-6-yl]pyrrolidin-3-yl}dimethylamine;
2-(3,5-Dimethylphenyl)-3-pyrid-4-yl-6-(4-pyrrolidin-1-ylpiperid-1-yl)imidazo[1,2-b]pyridazine;
6-(4-Morpholin-4-ylpiperid-1-yl)-2-phenyl-3-pyrid-4-ylimidazo[1,2-b]pyridazine;
6-[4-(2,6-Dimethylmorpholin-4-yl)piperid-1-yl]-2-phenyl-3-pyrid-4-ylimidazo[1,2-b]pyridazine;
{1-[2-(4-Fluorophenyl)-3-pyrid-4-ylimidazo[1,2-b]pyridazin-6-yl]piperid-4-yl}dimethylamine;
2-Phenyl-3-pyrid-4-yl-6-(4-pyrrolidin-1-ylpiperid-1-yl)imidazo[1,2-b]pyridazine;
2-(4-Fluorophenyl)-3-pyrid-4-yl-6-(4-pyrrolidin-1-ylpiperid-1-yl)imidazo[1,2-b]pyridazine;
2-(4-Fluorophenyl)-3-(2-methoxypyrid-4-yl)-6-(4-pyrrolidin-1-ylpiperid-1-yl)imidazo[1,2-b]pyridazine;
(R)-1-{1-[2-(4-Fluorophenyl)-3-pyrid-4-ylimidazo[1,2-b]pyridazin-6-yl]piperid-4-yl}pyrrolidin-3-ol;
6-(4-Morpholin-4-ylpiperid-1-yl)-2-phenyl-3-pyrid-4-ylimidazo[1,2-b]pyridazine;
2-(3-Fluoro-5-methylphenyl)-6-((R)-3-methylpiperazin-1-yl)-3-pyrid-4-ylimidazo[1,2-b]pyridazine;
{-4-[2-(4-Fluorophenyl)-6-((R)-3-methylpiperazin-1-yl)imidazo[1,2-b]pyridazin-3-yl]pyrid-2-yl}methylamine;
6-(3,3-Dimethylpiperazin-1-yl)-2-(4-fluorophenyl)-7-methyl-3-pyrid-4-ylimidazo[1,2-b]pyridazine;
6-(3,3-Dimethylpiperazin-1-yl)-2-(4-fluorophenyl)-8-methyl-3-pyrid-4-ylimidazo[1,2-b]pyridazine;
6-(3,3-Dimethylpiperazin-1-yl)-2-(3-fluoro-5-methylphenyl)-3-pyrid-4-ylimidazo[1,2-b]pyridazine;
{4-[6-(3,3-Dimethylpiperazin-1-yl)-2-(4-fluorophenyl)imidazo[1,2-b]pyridazin-3-yl]pyrid-2-yl}methylamine;
6-((R)-3-Ethylpiperazin-1-yl)-2-(4-fluorophenyl)-3-pyrid-4-ylimidazo[1,2-b]pyridazine;
6-(3,3-Diethylpiperazin-1-yl)-2-(4-fluorophenyl)-3-pyrid-4-ylimidazo[1,2-b]pyridazine;
(±)-6-(3-Fluoromethylpiperazin-1-yl)-2-(4-fluorophenyl)-3-pyrid-4-ylimidazo[1,2-b]pyridazine;
(±)-{4-[2-(4-Fluorophenyl)-3-pyrid-4-ylimidazo[1,2-b]pyridazin-6-yl]piperazin-2-yl}methanol;
2-{4-[2-(3-Fluoro-5-methylphenyl)-3-pyrid-4-ylimidazo[1,2-b]pyridazin-6-yl]piperazin-1-yl}ethanol;
2-{4-[2-(4-Fluorophenyl)-3-(2-methylaminopyrid-4-yl)imidazo[1,2-b]pyridazin-6-yl]piperazin-1-yl}ethanol;
1-{4-[2-(4-Fluorophenyl)-3-pyrid-4-ylimidazo[1,2-b]pyridazin-6-yl]piperazin-1-yl}-2-methylpropan-2-ol;
1-{4-[2-(4-Fluorophenyl)-8-methyl-3-pyrid-4-ylimidazo[1,2-b]pyridazin-6-yl]piperazin-1-yl}-2-methylpropan-2-ol;
1-{4-[2-(4-Fluorophenyl)-7-methyl-3-pyrid-4-ylimidazo[1,2-b]pyridazin-6-yl]piperazin-1-yl}-2-methylpropan-2-ol;

1-{4-[2-(4-Fluorophenyl)-3-(2-methylaminopyrid-4-yl)imidazo[1,2-b]pyridazin-6-yl]piperazin-1-yl}-2-methylpropan-2-ol;
2-{(R)-4-[2-(4-Fluorophenyl)-3-pyrid-4-ylimidazo[1,2-b]pyridazin-6-yl]piperazin-2-yl}propan-2-ol;
2-(4-Fluorophenyl)-6-((R)-3-isopropylpiperazin-1-yl)-3-pyrid-4-ylimidazo[1,2-b]pyridazine;
{4-[2-(4-Fluorophenyl)-6-((R)-3-isopropylpiperazin-1-yl)imidazo[1,2-b]pyridazin-3-yl]pyrid-2-yl}methylamine;
2-(3-Fluorophenyl)-6-(4-isopropylpiperazin-1-yl)-3-(2-methoxypyrid-4-yl)imidazo[1,2-b]pyridazine;
2-(4-Fluorophenyl)-6-(4-isopropylpiperazin-1-yl)-7-methyl-3-pyrid-4-ylimidazo[1,2-b]pyridazine;
2-(4-Fluorophenyl)-6-(4-isopropylpiperazin-1-yl)-8-methyl-3-pyrid-4-ylimidazo[1,2-b]pyridazine;
{4-[2-(4-Fluorophenyl)-6-(4-isopropylpiperazin-1-yl)imidazo[1,2-b]pyridazin-3-yl]pyrid-2-yl}methylamine;
2-(3,4-Difluorophenyl)-6-(4-isopropylpiperazin-1-yl)-3-(2-methoxypyrid-4-yl)imidazo[1,2-b]pyridazine;
2-(3-Fluoro-5-methylphenyl)-6-(4-isopropylpiperazin-1-yl)-3-pyrid-4-ylimidazo[1,2-b]pyridazine;
(±)-6-(3,6-Diazabicyclo[3.2.0]hept-3-yl)-2-phenyl-3-pyrid-4-ylimidazo[1,2-b]pyridazine;
6-(1S,4S)-2,5-Diazabicyclo[2.2.1]hept-2-yl-2-phenyl-3-pyrid-4-ylimidazo[1,2-b]pyridazine;
{4-[(1S,4S)-6-2,5-Diazabicyclo[2.2.1]hept-2-yl-2-(4-fluorophenyl)imidazo[1,2-b]pyridazin-3-yl]pyrid-2-yl}methylamine;
2-(4-Fluorophenyl)-6-((1S,4S)-5-methyl-2,5-diazabicyclo[2.2.1]hept-2-yl)-3-pyrid-4-ylimidazo[1,2-b]pyridazine;
2-(4-Fluorophenyl)-7-methyl-6-((1S,4S)-5-methyl-2,5-diazabicyclo[2.2.1]hept-2-yl)-3-pyrid-4-ylimidazo[1,2-b]pyridazine;
2-(4-Fluorophenyl)-8-methyl-6-((1S,4S)-5-methyl-2,5-diazabicyclo[2.2.1]hept-2-yl)-3-pyrid-4-ylimidazo[1,2-b]pyridazine;
2-(4-Fluorophenyl)-6-((1S,4S)-5-methyl-2,5-diazabicyclo[2.2.1]hept-2-yl)-3-(2-methylpyrid-4-yl)imidazo[1,2-b]pyridazine;
2-Methyl-1-[(1S,4S)-5-(2-phenyl-3-pyrid-4-ylimidazo[1,2-b]pyridazin-6-yl)-2,5-diazabicyclo[2.2.1]hept-2-yl]propan-2-ol;
6-(3,6-Diazabicyclo[3.1.1]hept-3-yl)-2-(4-fluorophenyl)-3-pyrid-4-ylimidazo[1,2-b]pyridazine;
2-(4-Fluorophenyl)-6-(5-methylhexahydropyrrolo[3,4-c]pyrrol-2(1H)-yl)-3-pyrid-4-ylimidazo[1,2-b]pyridazine;
2-(4-Fluorophenyl)-7-methyl-6-(5-methylhexahydropyrrolo[3,4-c]pyrrol-2(1H)-yl)-3-pyrid-4-ylimidazo[1,2-b]pyridazine;
2-(4-Fluorophenyl)-8-methyl-6-(5-methylhexahydropyrrolo[3,4-c]pyrrol-2(1H)-yl)-3-pyrid-4-ylimidazo[1,2-b]pyridazine;
2-(4-Fluorophenyl)-8-methyl-6-(-5-methylhexahydropyrrolo[3,4-c]pyrrol-2(1H)-yl)-3-(2-methylpyrid-4-yl)imidazo[1,2-b]pyridazine;
{4-[2-(4-Fluorophenyl)-6-(5-methylhexahydropyrrolo[3,4-c]pyrrol-2(1H)-yl)imidazo[1,2-b]pyridazin-3-yl]pyrid-2-yl}methylamine;
2-(4-Fluorophenyl)-3-(2-methoxypyrid-4-yl)-6-(5-methylhexahydropyrrolo[3,4-c]pyrrol-2(1H)-yl)imidazo[1,2-b]pyridazine;
2-(4-Fluorophenyl)-6-(5-methylhexahydropyrrolo[3,4-c]pyrrol-2(1H)-yl)-3-(2-methylpyrid-4-yl)imidazo[1,2-b]pyridazine;
{4-[2-(4-Fluorophenyl)-8-methyl-6-((3aR,6aS)-5-methylhexahydropyrrolo[3,4-c]pyrrol-2(1H)-yl)imidazo[1,2-b]pyridazin-3-yl]pyrid-2-yl}methylamine;
{4-[2-(4-Fluorophenyl)-7-methyl-6-(5-methylhexahydropyrrolo[3,4-c]pyrrol-2(1H)-yl)-imidazo[1,2-b]pyridazin-3-yl]pyrid-2-yl}methylamine;
(±)-2-(4-Fluorophenyl)-6-(hexahydropyrrolo[3,4-b]pyrrol-5(1H)-yl)-3-pyrid-4-ylimidazo[1,2-b]pyridazine;
(+)-2-(4-Fluorophenyl)-6-hexahydropyrrolo[3,4-b]pyrrol-5(1H)-yl-3-pyrid-4-ylimidazo[1,2-b]pyridazine;
(−)-2-(4-Fluorophenyl)-6-hexahydropyrrolo[3,4-b]pyrrol-5(1H)-yl-3-pyrid-4-ylimidazo[1,2-b]pyridazine;
(±)-{4-[2-(4-Fluorophenyl)-6-(hexahydropyrrolo[3,4-b]pyrrol-5(1H)-yl)imidazo[1,2-b]pyridazin-3-yl]pyrid-2-yl}methylamine;
6-(4aS,7aS)-octahydropyrrolo[3,4-b]pyrid-6-yl-2-phenyl-3-pyrid-4-ylimidazo[1,2-b]pyridazine;
3-(2-Methylpyrid-4-yl)-6-(4aS,7aS)-octahydropyrrolo[3,4-b]pyrid-6-yl-2-phenylimidazo[1,2-b]pyridazine;
3-(2-Methylpyrid-4-yl)-6-(4aR,7aR)-octahydropyrrolo[3,4-b]pyrid-6-yl-2-phenylimidazo[1,2-b]pyridazine;
2-(4-Fluorophenyl)-8-methyl-6-(4aS,7aS)-octahydropyrrolo[3,4-b]pyrid-6-yl-3-pyrid-4-ylimidazo[1,2-b]pyridazine;
2-(4-Fluorophenyl)-7-methyl-6-(4aS,7aS)-octahydropyrrolo[3,4-b]pyrid-6-yl-3-pyrid-4-ylimidazo[1,2-b]pyridazine;
2-(4-Fluorophenyl)-7-methyl-6-(4aR,7aR)-octahydropyrrolo[3,4-b]pyrid-6-yl-3-pyrid-4-ylimidazo[1,2-b]pyridazine;
2-(4-Fluorophenyl)-6-(4aS,7aS)-octahydropyrrolo[3,4-b]pyrid-6-yl-3-pyrid-4-ylimidazo[1,2-b]pyridazine;
2-(4-Fluorophenyl)-3-(2-methylpyrid-4-yl)-6-(4aS,7aS)-octahydropyrrolo[3,4-b]pyrid-6-ylimidazo[1,2-b]pyridazine;
{4-[2-(4-Fluorophenyl)-6-(octahydropyrrolo[3,4-b]pyrid-6-yl)imidazo[1,2-b]pyridazin-3-yl]pyrid-2-yl}methylamine;
6-(4aR,7aR)-Octahydropyrrolo[3,4-b]pyrid-6-yl-2-phenyl-3-pyrid-4-ylimidazo[1,2-b]pyridazine;
2-(4-Fluorophenyl)-6-(4aR,7aR)-octahydropyrrolo[3,4-b]pyrid-6-yl-3-pyrid-4-ylimidazo[1,2-b]pyridazine;
2-(4-Fluorophenyl)-3-(2-methylpyrid-4-yl)-6-(4aR,7aR)-octahydropyrrolo[3,4-b]pyrrolo[3,4-b]pyrid-6-ylimidazo[1,2-b]pyridazine;
2-(4-Fluorophenyl)-8-methyl-6-(4aR,7aR)-octahydropyrrolo[3,4-b]pyrid-6-yl-3-pyrid-4-ylimidazo[1,2-b]pyridazine;
6-(2,7-Diazaspiro[4.4]non-2-yl)-2-(4-fluorophenyl)-8-methyl-3-pyrid-4-ylimidazo[1,2-b]pyridazine;
6-(6,9-Diazaspiro[4.5]dec-9-yl)-2-(4-fluorophenyl)-3-pyrid-4-ylimidazo[1,2-b]pyridazine;
(±)-2-[2-(4-Fluorophenyl)-8-methyl-3-pyrid-4-ylimidazo[1,2-b]pyridazin-6-yl]-2,8-diazaspiro[5.5]undecane;
9-[2-(4-Fluorophenyl)-8-methyl-3-pyrid-4-ylimidazo[1,2-b]pyridazin-6-yl]-2,9-diazaspiro[5.5]undecane;
{4-[6-(2,9-Diazaspiro[5.5]undec-9-yl)-2-(4-fluorophenyl)imidazo[1,2-b]pyridazin-3-yl]pyrid-2-yl}methylamine;
9-[2-(3,4-Difluorophenyl)-3-pyrid-4-ylimidazo[1,2-b]pyridazin-6-yl]-2,9-diazaspiro[5.5]undecane;
9-[2-(3-Fluoro-5-methylphenyl)-3-pyrid-4-ylimidazo[1,2-b]pyridazin-6-yl]-2,9-diazaspiro[5.5]undecane;
2-(3-Fluorophenyl)-3-pyrid-4-yl-6-(4-pyrrolidin-1-ylpiperid-1-yl)imidazo[1,2-b]pyridazine;
{4-[2-(4-Fluorophenyl)-6-(4-pyrrolidin-1-ylpiperid-1-yl)imidazo[1,2-b]pyridazin-3-yl]pyrid-2-yl}methylamine;
2-(4-Fluorophenyl)-6-[4-((R)-3-fluoropyrrolidin-1-yl)piperid-1-yl]-3-pyrid-4-ylimidazo[1,2-b]pyridazine;
(R)-1-[1-(2-Phenyl-3-pyrid-4-ylimidazo[1,2-b]pyridazin-6-yl)piperid-4-yl]pyrrolidin-3-ol;
(R)-1-{1-[2-(3-Fluoro-5-methylphenyl)-3-pyrid-4-ylimidazo[1,2-b]pyridazin-6-yl]piperid-4-yl}-pyrrolidin-3-ol.

Table 1 below illustrates the chemical structures and the physical properties of a number of compounds according to the invention.

In this table:
- the "m.p. ° C." column gives the melting points of the products in degrees Celsius. "N.D" means that the melting point is not determined,
- in the "m.p. ° C." column, "HCl" or "CF$_3$COOH" represents a compound in hydrochloride or trifluoroacetate form and the ratio in parentheses is the (acid:base) ratio,
- the "LC-MS or (MS)" column gives the results of analysis of the products by LC-MS (liquid chromatography coupled to mass spectroscopy) performed on an Agilent LC-MSD Trap machine in positive ESI mode or by MS (mass spectroscopy) on an Autospec M machine (EBE) using the DCI-NH$_3$ technique.

"decomp" means that the compound undergoes decomposition;
"Me-amino" means methylamino;
"Me" means methyl;
"MeO" means methoxy;

TABLE 1

| N° | —N—A—L—B— | R$_7$ | R$_8$ | R$_2$ | R$_3$ | m.p. ° C. | M + H |
|---|---|---|---|---|---|---|---|
| 1 | Piperazin-1-yl | H | H | Phenyl | H | N.D | 357 |
| 2 | Piperazin-1-yl | H | H | 4-Fluorophenyl | H | 240-242 | 375 |
| 3 | Piperazin-1-yl | Me | Me | 4-Fluorophenyl | H | 233-235 | 403 |
| 4 | Piperazin-1-yl | H | H | 4-Fluorophenyl | Amino | 255 decomp. | 390 |
| 5 | Piperazin-1-yl | H | H | 4-Fluorophenyl | MeO | 227-229 | 405 |
| 6 | Piperazin-1-yl | H | H | 4-Chlorophenyl | H | 238-240 | 391 |
| 7 | Piperazin-1-yl | Me | H | 4-Chlorophenyl | H | 180-182 | 405 |
| 8 | Piperazin-1-yl | H | Me | 4-Chlorophenyl | H | 216-218 | 405 |
| 9 | Piperazin-1-yl | H | H | 3,5-Dimethylphenyl | H | N.D. | 385 |
| 10 | Piperazin-1-yl | H | H | 3,5-Difluorophenyl | H | N.D | 393 |
| 11 | Piperazin-1-yl | H | H | 3,5-Difluorophenyl | Me | N.D | 407 |
| 12 | Piperazin-1-yl | H | H | 3,4-Difluorophenyl | H | 183-185 | 393 |
| 13 | Piperazin-1-yl | H | H | 3,5-Dichlorophenyl | H | N.D | 425 |
| 14 | Piperazin-1-yl | H | H | 3,5-Dichlorophenyl | Me | N.D | 439 |
| 15 | (±)-3-Methylpiperazin-1-yl | H | H | Phenyl | H | N.D | 371 |
| 16 | (R)-3-Methylpiperazin-1-yl | H | H | Phenyl | H | N.D | 371 |
| 17 | (R)-3-Methylpiperazin-1-yl | H | H | Phenyl | Me | N.D | 385 |
| 18 | (S)-3-Methylpiperazin-1-yl | H | H | Phenyl | H | N.D | 371 |
| 19 | (R)-3-Methylpiperazin-1-yl | H | H | 3-Fluorophenyl | H | N.D | 389 |
| 20 | (±)-3-Methylpiperazin-1-yl | H | H | 4-Fluorophenyl | H | 197-199 | 389 |
| 21 | (R)-3-Methylpiperazin-1-yl | H | H | 4-Fluorophenyl | H | N.D | 389 |
| 22 | (S)-3-Methylpiperazin-1-yl | H | H | 4-Fluorophenyl | H | N.D | 389 |
| 23 | (R)-3-Methylpiperazin-1-yl | H | H | 4-Fluorophenyl | MeO | 215-218 | 419 |
| 24 | (R)-3-Methylpiperazin-1-yl | H | H | 3,4-Difluorophenyl | H | N.D | 407 |
| 25 | 3,3-Dimethylpiperazin-1-yl | H | H | Phenyl | H | N.D | 385 |
| 26 | 3,3-Dimethylpiperazin-1-yl | H | H | 4-Fluorophenyl | H | 232-235 HCl (3:1) | 403 |
| 27 | 3,3-Dimethylpiperazin-1-yl | H | H | 4-Fluorophenyl | MeO | 167-170 | 433 |
| 28 | 3,3-Dimethylpiperazin-1-yl | H | H | 3,5-Dimethylphenyl | H | N.D | 413 |
| 29 | 3,3-Dimethylpiperazin-1-yl | H | H | 3,5-Dimethylphenyl | Me | N.D | 427 |
| 30 | 3,3-Dimethylpiperazin-1-yl | H | H | 3,5-Dimethylphenyl | Amino | N.D | 428 |
| 31 | 3,3-Dimethylpiperazin-1-yl | H | H | 3,5-Difluorophenyl | H | N.D | 421 |
| 32 | 3,3-Dimethylpiperazin-1-yl | H | H | 3,5-Difluorophenyl | Me | N.D | 435 |
| 33 | 3,3-Dimethylpiperazin-1-yl | H | H | 3,5-Difluorophenyl | Amino | N.D | 436 |
| 34 | 3,3-Dimethylpiperazin-1-yl | H | H | 3,5-Dichlorophenyl | H | N.D | 453 |
| 35 | 3,3-Dimethylpiperazin-1-yl | H | H | 3,5-Dichlorophenyl | Me | N.D | 467 |
| 36 | (±)-3,4-Dimethylpiperazin-1-yl | H | H | 4-Fluorophenyl | H | 254-256 | 403 |
| 37 | cis-3,5-Dimethylpiperazin-1-yl | H | H | Phenyl | H | N.D | 385 |
| 38 | cis-3,5-Dimethylpiperazin-1-yl | H | H | Phenyl | Me | N.D | 399 |
| 39 | cis-3,5-Dimethylpiperazin-1-yl | H | H | 3-Fluorophenyl | H | N.D | 403 |
| 40 | cis-3,5-Dimethylpiperazin-1-yl | H | H | 4-Fluorophenyl | H | 231-233 | 403 |
| 41 | cis-3,5-Dimethylpiperazin-1-yl | H | H | 4-Fluorophenyl | MeO | 173-175 | 433 |
| 42 | cis-3,5-Dimethylpiperazin-1-yl | H | H | 3,5-Dimethylphenyl | H | N.D | 413 |
| 43 | cis-3,5-Dimethylpiperazin-1-yl | H | H | 3,4-Difluorophenyl | H | N.D | 421 |
| 44 | cis-3,5-Dimethylpiperazin-1-yl | Me | H | 4-Chlorophenyl | H | 230-232 | 433 |
| 45 | cis-3,5-Dimethylpiperazin-1-yl | H | Me | 4-Fluorophenyl | H | 235-237 | 417 |
| 46 | 4-Methylpiperazin-1-yl | H | H | 2-Chlorophenyl | H | 198-200 | 405 |
| 47 | 4-Methylpiperazin-1-yl | H | H | 3-Chlorophenyl | H | 195-197 | 405 |
| 48 | 4-Methylpiperazin-1-yl | H | H | 4-Chlorophenyl | H | 260-262 | 405 |
| 49 | 4-Methylpiperazin-1-yl | H | H | 3-Fluorophenyl | H | 205-206 | 389 |
| 50 | 4-Methylpiperazin-1-yl | H | H | 4-Fluorophenyl | H | 294-296 248-250 | 389 |
| 51 | 4-Methylpiperazin-1-yl | H | H | 3,4-Difluorophenyl | H | 210 | 407 |
| 52 | 4-Methylpiperazin-1-yl | H | H | 3-Methoxyphenyl | H | 131 | 401 |
| 53 | 4-Methylpiperazin-1-yl | H | H | 4-Methoxyphenyl | H | 183-185 | 401 |
| 54 | 4-Methylpiperazin-1-yl | H | H | 4-Methylphenyl | H | 205-206 | 385 |
| 55 | 4-Methylpiperazin-1-yl | H | H | 4-Trifluoromethyl-phenyl | H | 201-203 | 439 |
| 56 | 4-Methylpiperazin-1-yl | H | H | 4-Fluorophenyl | Me | 258-260 | 403 |
| 57 | 4-Methylpiperazin-1-yl | H | H | 4-Fluorophenyl | Amino | 235-238 | 404 |
| 58 | 4-Methylpiperazin-1-yl | H | H | 4-Fluorophenyl | Di-Me-amino | 180-183 | 432 |
| 59 | 4-Methylpiperazin-1-yl | H | H | 4-Fluorophenyl | MeO | 189-194 | 419 |
| 60 | 4-Ethylpiperazin-1-yl | H | H | 4-Fluorophenyl | H | 208-210 | 403 |
| 61 | 4-Ethylpiperazin-1-yl | H | H | 3,5-Dimethylphenyl | H | N.D | 413 |
| 62 | 4-(2-hydroxyethyl)piperazin-1-yl | H | H | Phenyl | H | N.D | 401 |

TABLE 1-continued

| N° | —N—A—L—B— | R7 | R8 | R2 | R3 | m.p. °C | M + H |
|---|---|---|---|---|---|---|---|
| 63 | 4-(2-hydroxyethyl)piperazin-1-yl | H | H | 3-Fluorophenyl | H | N.D | 419 |
| 64 | 4-(2-hydroxyethyl)piperazin-1-yl | H | H | 4-Fluorophenyl | H | 203-206 | 419 |
| 65 | 4-(2-hydroxyethyl)piperazin-1-yl | H | H | 4-Fluorophenyl | MeO | 176-179 | 449 |
| 66 | 4-(2-hydroxyethyl)piperazin-1-yl | H | H | 3,4-Difluorophenyl | H | N.D | 437 |
| 67 | 4-(2-hydroxyethyl)piperazin-1-yl | H | H | 4-Chlorophenyl | H | N.D | 435 |
| 68 | 4-(2-hydroxyethyl)piperazin-1-yl | H | H | 4-Chlorophenyl | amino | 191-193 | 450 |
| 69 | 4-(2-Methoxyethyl)piperazin-1-yl | H | H | 4-Chlorophenyl | H | N.D | 449 |
| 70 | 4-(2-Fluoroethyl)piperazin-1-yl | H | H | 4-Fluorophenyl | H | 183-185 | 421 |
| 71 | 4-(2-Fluoroethyl)piperazin-1-yl | H | H | 4-Fluorophenyl | MeO | 149-151 | 451 |
| 72 | 4-(2,2,2-Trifluoroethyl)piperazin-1-yl | H | H | Phenyl | H | 188-190 | 439 |
| 73 | 4-(2,2,2-Trifluoroethyl)piperazin-1-yl | H | H | 4-Fluorophenyl | H | 188-191 184-186 | 457 |
| 74 | 4-Cyclopropylpiperazin-1-yl | H | H | 4-Fluorophenyl | H | 205-208 | 415 |
| 75 | 4-Cyclopropylpiperazin-1-yl | H | H | 4-Fluorophenyl | MeO | 194-196 | 445 |
| 76 | 4-Isopropylpiperazin-1-yl | H | H | Phenyl | MeO | 157-159 | 429 |
| 77 | 4-Isopropylpiperazin-1-yl | H | H | 3-Fluorophenyl | H | N.D | 417 |
| 78 | 4-Isopropylpiperazin-1-yl | H | H | 4-Fluorophenyl | H | 185-187 | 417 |
| 79 | 4-Isopropylpiperazin-1-yl | H | H | 4-Fluorophenyl | MeO | 153-156 | 447 |
| 80 | 4-Isopropylpiperazin-1-yl | H | H | 3,4-Difluorophenyl | H | N.D | 435 |
| 81 | 4-Isopropylpiperazin-1-yl | H | H | 4-Chlorophenyl | amino | 236-239 | 448 |
| 82 | 4-(2-Hydroxy-2-methylpropyl)piperazin-1-yl | H | H | Phenyl | H | N.D | 429 |
| 83 | 4-(2-Hydroxy-2-methylpropyl)piperazin-1-yl | H | H | 3-Fluorophenyl | H | N.D | 447 |
| 84 | 4-(2-Hydroxy-2-methylpropyl)piperazin-1-yl | H | H | 4-Fluorophenyl | MeO | 176-178 | 477 |
| 85 | 4-n-Butylpiperazin-1-yl | H | H | 4-Chlorophenyl | H | N.D | 447 |
| 86 | 4-(3-Hydroxy-3-methylbutyl)piperazin-1-yl | H | H | 4-Fluorophenyl | MeO | 151-154 | 491 |
| 87 | 4-Cyclohexylpiperazin-1-yl | H | H | 4-Fluorophenyl | H | 197-199 | 457 |
| 88 | 4-Acetylpiperazin-1-yl | H | H | 4-Fluorophenyl | H | 231-233 | 417 |
| 89 | 4-Isobutyrylpiperazin-1-yl | H | H | 4-Fluorophenyl | H | 197-200 | 445 |
| 90 | (±)-Hexahydropyrrolo[1,2-a]pyrazin-2-yl | H | H | 4-Fluorophenyl | H | 223-225 | 415 |

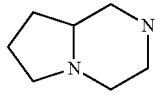

| 91 | (S)-Hexahydropyrrolo[1,2-a]pyrazin-2-yl | H | H | 4-Fluorophenyl | MeO | 187-189 | 445 |

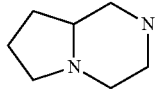

| 92 | (1S,4S)-2,5-diazabicyclo[2.2.1]hept-2-yl | H | H | Phenyl | H | N.D | 369 |

| 93 | (1S,4S)-5-Benzyl-2,5-diazabicyclo[2.2.1]hept-2-yl | H | H | 3-Fluorophenyl | H | N.D | 477 |
| 94 | (1S,4S)-2,5-diazabicyclo[2.2.1]hept-2-yl | H | H | 4-Fluorophenyl | H | 192-196 | 387 |
| 95 | (1S,4S)-5-Benzyl-2,5-diazabicyclo[2.2.1]hept-2-yl | H | H | 4-Fluorophenyl | H | 182-184 | 477 |
| 96 | (1S,4S)-2,5-diazabicyclo[2.2.1]hept-2-yl | H | H | 4-Fluorophenyl | MeO | 164-167 | 417 |
| 97 | (1S,4S)-5-(2-Hydroxyethyl)-2,5-diaza-bicyclo[2.2.1]hept-2-yl | H | H | 4-Fluorophenyl | MeO | 154-156 | 461 |
| 98 | 5-Isopropyl-2,5-diazabicyclo[2.2.1]-hept-2-yl | H | H | 4-Fluorophenyl | MeO | 204-206 | 459 |
| 99 | 4-Methyl[1,4]diazepan-1-yl | H | H | 4-Fluorophenyl | H | 138-140 | 403 |
| 100 | (±)-Octahydro-1H-pyrrolo[1,2-d][1,4]-diazepin-3-yl | H | H | 4-Fluorophenyl | H | 166-168 | 429 |

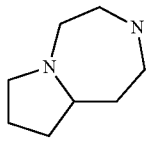

| 101 | (±)-1,4-Diazabicyclo[3.2.2]non-4-yl | H | H | 4-Fluorophenyl | H | 286-288 | 415 |

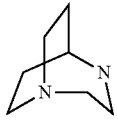

| 102 | (±)-1,4-Diazabicyclo[3.2.2]non-4-yl | H | H | 3,5-Dimethyl-phenyl | H | N.D | 425 |

TABLE 1-continued

| N° | —N—A—L—B— | R₇ | R₈ | R₂ | R₃ | m.p. ° C. | M + H |
|---|---|---|---|---|---|---|---|
| 103 | (±)-3,6-diazabicyclo[3.2.0]hept-3-yl | H | H | Phenyl | H | 212-218 | 370 |
| 104 | (±)-Hexahydropyrrolo[3,4-b]pyrrol-5(1H)-yl | H | H | Phenyl | H | 181-183 | 383 |
| 105 | Hexahydropyrrolo[3,4-b]pyrrol-5(1H)-yl | H | H | Phenyl | Me | 170-172 | 397 |
| 106 | Hexahydropyrrolo[3,4-c]pyrrol-2(1H)-yl | H | H | Phenyl | H | 199-201 | 383 |
| 107 | Hexahydropyrrolo[3,4-c]pyrrol-2(1H)-yl | H | H | Phenyl | Me | 214-217 | 397 |
| 108 | Hexahydropyrrolo[3,4-c]pyrrol-2(1H)-yl | H | H | 3-Fluorophenyl | Me | 217-219 | 415 |
| 109 | Hexahydropyrrolo[3,4-c]pyrrol-2(1H)-yl | H | H | 4-Fluorophenyl | H | 246-250 195-198 | 401 |
| 110 | Hexahydropyrrolo[3,4-c]pyrrol-2(1H)-yl | H | H | 4-Fluorophenyl | Me | 200-202 | 415 |
| 111 | Hexahydropyrrolo[3,4-c]pyrrol-2(1H)-yl | H | H | 4-Chlorophenyl | Amino | 267-270 | 432 |
| 112 | Hexahydropyrrolo[3,4-c]pyrrol-2(1H)-yl | H | H | 4-Fluorophenyl | MeO | 126-129 | 431 |
| 113 | 5-Benzylhexahydropyrrolo[3,4-c]pyrrol-2(1H)-yl | Me | Me | 4-Fluorophenyl | Amino | 113 | |
| 114 | Hexahydropyrrolo[3,4-c]pyrrol-2(1H)-yl | Me | Me | 4-Fluorophenyl | Amino | 254-256 | 444 |
| 115 | 5-Cyclopropylhexahydropyrrolo[3,4-c]pyrrol-2(1H)-yl | H | H | 4-Fluorophenyl | H | 204-206 | 441 |
| 116 | 5-Isopropylhexahydropyrrolo[3,4-c]pyrrol-2(1H)-yl | H | H | 4-Fluorophenyl | H | 200-202 | 443 |
| 117 | 5-Isopropylhexahydropyrrolo[3,4-c]pyrrol-2(1H)-yl | H | H | 4-Fluorophenyl | Me | 197-199 | 457 |
| 118 | 5-Isopropylhexahydropyrrolo[3,4-c]pyrrol-2(1H)-yl | H | H | 4-Fluorophenyl | MeO | 208-211 | 473 |
| 119 | (±)-(cis)-Octahydro-6H-pyrrolo[3,4-b]pyrid-6-yl | H | H | Phenyl | H | 212-215 | 397 |
| 120 | (±)-(cis)-Octahydro-6H-pyrrolo[3,4-b]pyrid-6-yl | H | H | Phenyl | Me | 208-210 | 411 |
| 121 | (±)-(cis)-Decahydro[2,6]naphthyridin-2-yl | H | H | 4-Fluorophenyl | H | 231-234 (3HCl) | 429 |
| 122 | (±)-2,7-Diazaspiro[4.4]non-2-yl | H | H | 3-Fluorophenyl | H | N.D | 415 |
| 123 | (±)-2,7-Diazaspiro[4.4]non-2-yl | H | H | 4-Fluorophenyl | H | 204-206 | 415 |
| 124 | (±)-2,8-Diazaspiro[4.5]dec-2-yl | H | H | 4-Fluorophenyl | H | 198-200 | 429 |
| 125 | (±)-2,7-Diazaspiro[4.5]dec-2-yl | H | H | 4-Fluorophenyl | H | 228-230 | 429 |

TABLE 1-continued

| N° | —N—A—L—B— | R₇ | R₈ | R₂ | R₃ | m.p. °C. | M + H |
|---|---|---|---|---|---|---|---|
| 126 | (±)-2,8-Diazaspiro[4.5]dec-8-yl | H | H | 4-Fluorophenyl | H | 223-225 | 429 |
| 127 | (±)-2,7-Diazaspiro[4.5]dec-7-yl | H | H | 4-Fluorophenyl | H | 162-165 | 429 |
| 128 | 3,9-Diazaspiro[5.5]dec-3-yl | H | H | 4-Fluorophenyl | H | 230-232 | 443 |
| 129 | 2,9-Diazaspiro[5.5]undec-9-yl | H | H | Phenyl | H | 173-176 | 425 |
| 130 | 2,9-Diazaspiro[5.5]undec-9-yl | H | H | Phenyl | Me | 175-179 | 439 |
| 131 | 2,9-Diazaspiro[5.5]undec-9-yl | H | H | 3-Fluorophenyl | Me | 189-191 | 457 |
| 132 | 2,9-Diazaspiro[5.5]undec-9-yl | H | H | 4-Fluorophenyl | H | 253-255 | 443 |
| 133 | 2,9-Diazaspiro[5.5]undec-9-yl | H | H | 4-Fluorophenyl | Me | 228-230 | 457 |
| 134 | 2,9-Diazaspiro[5.5]undec-9-yl | H | H | 4-Chlorophenyl | Amino | 255-258 240-243 | 474 |
| 135 | 2,9-Diazaspiro[5.5]undec-9-yl | H | H | 4-Fluorophenyl | MeO | 191-194 | 473 |
| 136 | 2,9-Diazaspiro[5.5]undec-9-yl | H | H | 4-Fluorophenyl | H | 248-250 | 443 |
| 137 | (±)-2,8-Diazaspiro[5.5]undec-9-yl | H | H | 4-Fluorophenyl | H | 218-220 | 443 |
| 138 | 1-Oxa-4,9-diazaspiro[5.5]undec-9-yl | H | H | Phenyl | H | N.D. | 427 |

TABLE 1-continued

| N° | —N—A—L—B— | $R_7$ | $R_8$ | $R_2$ | $R_3$ | m.p. °C. | M + H |
|---|---|---|---|---|---|---|---|
| 139 | 1-Oxa-4,9-diazaspiro[5.5]undec-9-yl | H | H | 4-Fluorophenyl | H | 219-221 | 445 |
| 140 | 1-Oxa-4,9-diazaspiro[5.5]undec-9-yl | H | H | 4-Fluorophenyl | MeO | 198-200 | 475 |
| 141 | 1-Oxa-4,9-diazaspiro[5.5]undec-9-yl | H | H | 4-Chlorophenyl | amino | 241-244 | 476 |
| 142 | (±)-3-Dimethylaminopyrrolidin-1-yl | H | H | 4-Fluorophenyl | H | 184-186 | 403 |
| 143 | 4-(Pyrrolidin-1-yl)piperid-1-yl | H | H | 3,5-Dimethyl-phenyl | H | N.D. | 453 |
| 144 | 4-(Morpholin-4-yl)piperid-1-yl | H | H | Phenyl | H | N.D. | 441 |
| 145 | 4-(2,6-Dimethylmorpholin-4-yl)-piperid-1-yl | H | H | Phenyl | H | N.D. | 469 |
| 146 | 4-Dimethylaminopiperid-1-yl | H | H | 4-Fluorophenyl | H | 193-195 | 417 |
| 147 | 4-Pyrrolidin-1-ylpiperid-1-yl | H | H | Phenyl | H | 165.0-165.5 | 425 |
| 148 | 4-Pyrrolidin-1-ylpiperid-1-yl | H | H | 4-Fluorophenyl | H | 210-212 | 443 |
| 149 | 4-Pyrrolidin-1-ylpiperid-1-yl | H | H | 4-Fluorophenyl | MeO | 161-164 | 473 |
| 150 | 4-((R)-3-Hydroxypyrrolidin-1-yl)-piperid-1-yl | H | H | 4-Fluorophenyl | H | 203-205 | 459 |
| 151 | 4-Morpholin-4-ylpiperid-1-yl | H | H | Phenyl | H | N.D. | 441 |
| 152 | (R)-3-Methyl-piperazin-1-yl | H | H | 3-Fluoro-5-methyl-phenyl | H | 216-219 | 403 |
| 153 | (R)-3-Methyl-piperazin-1-yl | H | H | 4-Fluoro-phenyl | Me-amino | 232-234 | 418 |
| 154 | 3,3-Dimethyl-piperazin-1-yl | Me | H | 4-Fluoro-phenyl | H | 224-226 | 417 |
| 155 | 3,3-Dimethyl-piperazin-1-yl | H | Me | 4-Fluoro-phenyl | H | 224-226 222-224 | 417 |
| 156 | 3,3-Dimethyl-piperazin-1-yl | H | H | 3-Fluoro-5-methyl-phenyl | H | 218-221 | 417 |
| 157 | 3,3-Dimethyl-piperazin-1-yl | H | H | 4-Fluoro-phenyl | Me-amino | 235-237 | 432 |
| 158 | (R)-3-Ethyl-piperazin-1-yl | H | H | 4-Fluoro-phenyl | H | 186-188 | 403 |
| 159 | 3,3-Diethyl-piperazin-1-yl | H | H | 4-Fluoro-phenyl | H | 82-184 | 431 |
| 160 | (±)-3-Fluoromethyl-piperazin-1-yl | H | H | 4-Fluoro-phenyl | H | 198-200 | 407 |
| 161 | (±)--(3-Hydroxymethyl)-piperazin-1-yl | H | H | 4-Fluoro-phenyl | H | 215-219 | 405 |
| 162 | 4-(2-hydroxyethyl)piperazin-1-yl | H | H | 3-Fluoro-5-methyl-phenyl | H | 187-189 | 433 |
| 163 | 4-(2-hydroxyethyl)piperazin-1-yl | H | H | 4-Fluoro-phenyl | Me-amino | 207-209 | 448 |
| 164 | 4-(2-Hydroxy-2-methyl-propyl)piperazin-1-yl | H | H | 4-Fluoro-phenyl | H | 212-214 | 447 |
| 165 | 4-(2-Hydroxy-2-methyl-propyl)piperazin-1-yl | H | Me | 4-Fluoro-phenyl | H | 205-207 | 461 |
| 166 | 4-(2-Hydroxy-2-methyl-propyl)piperazin-1-yl | Me | H | 4-Fluoro-phenyl | H | 219-221 | 461 |
| 167 | 4-(2-hydroxy-2-methyl-propyl)piperazin-1-yl | H | H | 4-Fluoro-phenyl | Me-amino | 182-184 | 476 |
| 168 | 3-(1-hydroxy-1-methyl-ethyl)-piperazin-1-yl | H | H | 4-Fluoro-phenyl | H | 184-186 | 433 |
| 169 | (R)-3-Isopropylpiperazin-1-yl | H | H | 4-Fluorophenyl | H | 179-181 | 417 |
| 170 | (R)-3-Isopropyl-piperazin-1-yl | H | H | 4-Fluoro-phenyl | Me-amino | 172-174 | 446 |
| 171 | 4-Isopropyl-piperazin-1-yl | H | H | 3-Fluoro-phenyl | MeO | 124-126 | 447 |
| 172 | 4-Isopropyl-piperazin-1-yl | Me | H | 4-Fluoro-phenyl | H | 210-212 | 431 |
| 173 | 4-Isopropyl-piperazin-1-yl | H | Me | 4-Fluoro-phenyl | H | 195-197 | 431 |
| 174 | 4-Isopropyl-piperazin-1-yl | H | H | 4-Fluoro-phenyl | Me-amino | 207-209 | 446 |
| 175 | 4-Isopropylpiperazin-1-yl | H | H | 3,4-Difluorophenyl | MeO | 136-138 | 465 |
| 176 | 4-Isopropyl-piperazin-1-yl | H | H | 3-Fluoro-5-methyl-phenyl | H | 161-163 | 431 |
| 177 | (±)-3,6-diaza-bicyclo[3.2.0]hept-2-yl | H | H | Phenyl | H | 212-128 | 369 |
| 178 | (1S,4S)-2,5-Diaza-bicyclo[2.2.1]hept-2-yl | H | H | Phenyl | H | N.D. | 369 |
| 179 | (1S,4S)-6-2,5-Diaza-bicyclo[2.2.1]hept-2-yl | H | H | 4-Fluoro-phenyl | Me-amino | 191-193 | 416 |
| 180 | (1S,4S)-5-methyl-2,5-diaza-bicyclo[2.2.1]hept-2-yl | H | H | 4-Fluoro-phenyl | H | 178-180 181-189 | 401 |
| 181 | (1S,4S)-5-methyl-2,5-diaza-bicyclo[2.2.1]hept-2-yl | Me | H | 4-Fluoro-phenyl | H | 185-187 | 415 |
| 182 | (1S,4S)-5-methyl-2,5-diaza-bicyclo[2.2.1]hept-2-yl | H | Me | 4-Fluoro-phenyl | H | 212-214 | 415 |
| 183 | (1S,4S)-5-methyl-2,5-diaza-bicyclo[2.2.1]hept-2-yl | H | H | 4-Fluoro-phenyl | Me | 156-158 | 415 |
| 184 | 1-(1S,4S)-(2,5-Diaza-bicyclo[2.2.1]hept-2-yl)-2-methyl-propan-2-ol | H | H | Phenyl | H | ND CF$_3$COOH (3:1) | 441 |

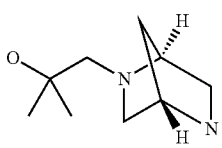

| 185 | 3,6-Diaza-bicyclo[3.1.1]hept-3-yl | H | H | 4-Fluoro-phenyl | H | 244-246 | 387 |
| 186 | 5-methyl-hexahydro-pyrrolo[3,4-c]pyrrol-2(1H)-yle | H | H | 4-Fluoro-phenyl | H | 166-169 | 415 |
| 187 | 5-methyl-hexahydro-pyrrolo[3,4-c]pyrrol-2(1H)-yle | Me | H | 4-Fluoro-phenyl | H | 164-166 | 429 |
| 188 | 5-methyl-hexahydro-pyrrolo[3,4-c]pyrrol-2(1H)-yle | H | Me | 4-Fluoro-phenyl | H | 235-238 | 429 |
| 189 | 5-methyl-hexahydro-pyrrolo[3,4-c]pyrrol-2(1H)-yle | H | Me | 4-Fluoro-phenyl | Me | 219-221 | 443 |
| 190 | 5-methyl-hexahydro-pyrrolo[3,4-c]pyrrol-2(1H)-yle | H | H | 4-Fluoro-phenyl | Me-amino | 211-213 | 444 |
| 191 | 5-methyl-hexahydro-pyrrolo[3,4-c]pyrrol-2(1H)-yle | H | H | 4-Fluoro-phenyl | MeO | 205-207 | 445 |

TABLE 1-continued

| N° | —N—A—L—B— | R7 | R8 | R2 | R3 | m.p. °C. | M + H |
|---|---|---|---|---|---|---|---|
| 192 | 5-methyl-hexahydro-pyrrolo[3,4-c]pyrrol-2(1H)-yle | H | H | 4-Fluoro-phenyl | Me | 173-178 | 429 |
| 193 | 5-methyl-hexahydro-pyrrolo[3,4-c]pyrrol-2(1H)-yle | H | Me | 4-Fluoro-phenyl | Me-amino | 190-192 | 458 |
| 194 | 5-methyl-hexahydro-pyrrolo[3,4-c]pyrrol-2(1H)-yle | Me | H | 4-Fluoro-phenyl | Me-amino | 211-213 | 458 |
| 195 | (±)-Hexahydro-pyrrolo[3,4-b]-ylpyrrol-5(1H)-yl | H | H | 4-Fluoro-phenyl | H | 237-239 | 401 |
| 196 | (±)-Hexahydro-pyrrolo[3,4-b]pyrrol-5(1H)-yl | H | H | 4-Fluoro-phenyl | H | 244-246 | 401 |
| 197 | (−)-Hexahydro-pyrrolo[3,4-b]pyrrol-5(1H)-yl | H | H | 4-Fluoro-phenyl | H | 246-248 | 401 |
| 198 | (±)-Hexahydro-pyrrolo[3,4-b]pyrrol-5(1H)-yl | H | H | 4-Fluoro-phenyl | Me-amino | 189-191 | 430 |
| 199 | (4aS,7aS)-Octahydro-pyrrolo[3,4-b]pyridin-6-yl | H | H | Phenyl | H | 237-239 | 397 |
| 200 | (4aS,7aS)-Octahydro-pyrrolo[3,4-b]pyridin-6-yl | H | H | Phenyl | Me | 203-206 | 411 |
| 201 | (4aR,7aR)-Octahydro-pyrrolo[3,4-b]pyridin-6-yl | H | H | Phenyl | Me | 199-201 | 411 |
| 202 | (4aS,7aS)-octahydro-pyrrolo[3,4-b]pyridin-6-yl | H | Me | 4-Fluoro-phenyl | H | 217-219 | 429 |
| 203 | (4aS,7aS)-octahydro-pyrrolo[3,4-b]pyridin-6-yl | Me | H | 4-Fluoro-phenyl | H | 234-236 | 429 |
| 204 | (4aR,7aR)-octahydro-pyrrolo[3,4-b]pyridin-6-yl | Me | H | 4-Fluoro-phenyl | H | 229-231 | 429 |
| 205 | (4aS,7aS)-octahydro-pyrrolo[3,4-b]pyridin-6-yl | H | H | 4-Fluoro-phenyl | H | 238-240 | 415 |
| 206 | (4aS,7aS)-octahydro-pyrrolo[3,4-b]pyridin-6-yl | H | H | 4-Fluoro-phenyl | Me | 219-221 | 429 |
| 207 | Octahydro-pyrrolo[3,4-b]pyridin-6-yl | H | H | 4-Fluoro-phenyl | Me-amino | 244-246 | 444 |
| 208 | (4aR,7aR)-Octahydro-pyrrolo[3,4-b]pyridin-6-yl | H | H | Phenyl | H | 234-236 | 297 |
| 209 | (4aR,7aR)-Octahydro-pyrrolo[3,4-b]pyridin-6-yl | H | H | 4-Fluoro-phenyl | H | 222-224 | 415 |
| 210 | (4aR,7aR)-octahydro-pyrrolo[3,4-b]pyridin-6-yl | H | H | 4-Fluoro-phenyl | Me | 220-222 | 429 |
| 211 | (4aR,7aR)-octahydro-pyrrolo[3,4-b]pyridin-6-yl | H | Me | 4-Fluoro-phenyl | H | 219-221 | 429 |
| 212 | (±)-2,7-Diaza-spiro[4.4]non-2-yl | H | Me | 4-Fluoro-phenyl | H | 219-222 | 429 |
| 213 | 6,9-Diaza-spiro[4.5]dec-9-yl | H | H | 4-Fluoro-phenyl | H | 209-211 | 429 |
| 214 | (±)-2,8-Diaza-spiro[5.5]dec-2-yl | H | Me | 4-Fluoro-phenyl | H | 215-218 | 457 |
| 215 | 2,9-Diaza-spiro[5.5]undec-9-yl | H | Me | 4-Fluoro-phenyl | H | 242-245 | 457 |
| 216 | 2,9-Diaza-spiro[5.5]undec-9-yl | H | H | 4-Fluoro-phenyl | Me-amino | 238-241 | 472 |
| 217 | 2,9-Diaza-spiro[5.5]undec-9-yl | H | H | 3,4-Difluorophenyl | H | 227-229 | 461 |
| 218 | 2,9-Diaza-spiro[5.5]undec-9-yl | H | H | 3-Fluoro-5-methyl-phenyl | H | 172-175 | 457 |
| 219 | 4-Pyrrolidin-1-yl-piperidin-1-yl | H | H | 3-Fluoro-phenyl | H | N.D. | 443 |
| 220 | 4-pyrrolidin-1-yl-piperidin-1-yl | H | H | 4-Fluoro-phenyl | Me-amino | 217-219 | 472 |
| 221 | 4-((R)-3-fluoro-pyrrolidin-1-yl)-piperidin-1-yl | H | H | 4-Fluorophenyl | H | 208-210 | 461 |
| 222 | 4-((R)-3-Hydroxy-pyrrolidin-1-yl)-piperidin-1-yl | H | H | Phenyl | H | 154-158 | 441 |
| 223 | 4-((R)-3-Hydroxy-pyrrolidin-1-yl)-piperidin-1-yl | H | H | 3-Fluoro-5-methyl-phenyl | H | 178-183 | 473 |

A subject the invention is also a process for preparing the compounds of the invention of formula (I).

In accordance with the invention, the compounds of general formula (I) may be prepared according to the general process described in Scheme 1 below.

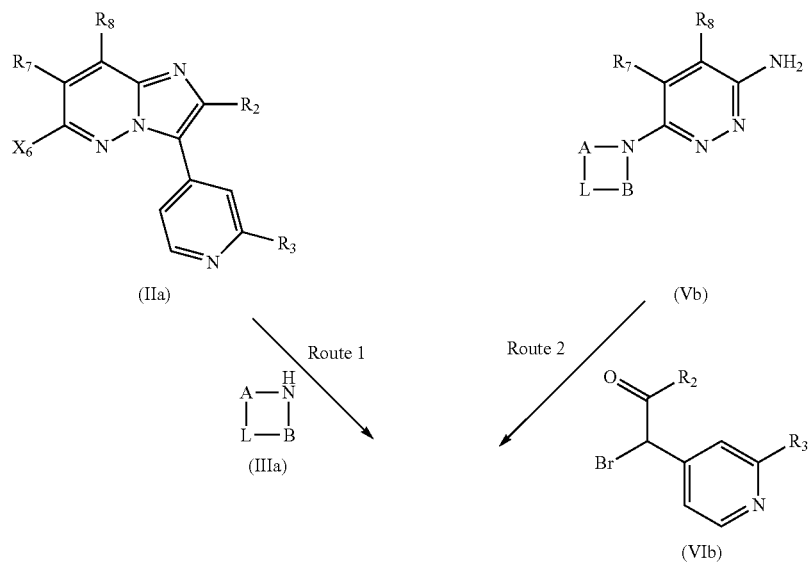

SCHEME 1

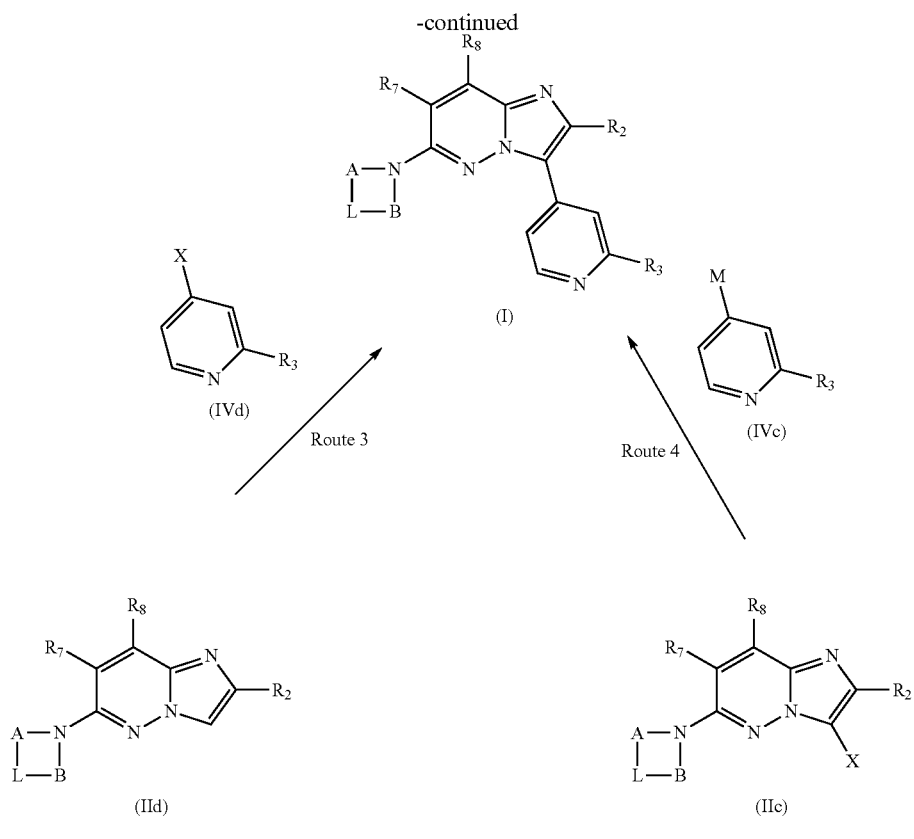

In the text hereinbelow, the term "leaving group" means a group that can be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a mesyl, tosyl, triflate, acetyl, etc. Examples of leaving groups and references for preparing them are given in "Advances in Organic Chemistry", J. March, $3^{rd}$ Edition, Wiley Interscience, pp. 310-316.

Scheme 1, Route 1: Introduction of the Amine

In general, and as illustrated in Scheme 1, the 6-amino-3-pyrid-4-ylimidazo[1,2-b]pyridazine derivatives of general formula (I) in which $R_2$, $R_3$, A, L, B, $R_7$ and $R_8$ are as defined above may be prepared from a 3-pyrid-4-ylimidazo[1,2-b]pyridazine derivative of general formula (IIa), in which $R_2$, $R_3$, $R_7$ and $R_8$ are as defined above and $X_6$ represents a leaving group such as a halogen, by treatment with an amine of general formula (IIIa) in which A, L and B are as defined above. This reaction may be performed by heating the reagents in a polar solvent such as dimethyl sulfoxide or aliphatic alcohols, for example pentanol.

Scheme 1, Route 2: Construction of the Heterocycle

The 6-amino-3-pyrid-4-ylimidazo[1,2-b]pyridazine derivatives of general formula (I) in which $R_2$, $R_3$, A, L, B, $R_7$ and $R_8$ are as defined above may also be prepared by condensation between a pyridazin-3-ylamine derivative of general formula (Vb) in which A, L, B, $R_7$ and $R_8$ are as defined above and a 2-bromo-2-(pyrid-4-yl)ethan-1-one derivative of general formula (VIb) in which $R_2$ and $R_3$ are as defined above.

The reaction may be performed by heating the reagents in a polar solvent such as aliphatic alcohols, for example ethanol or butanol.

Scheme 1, Route 3: Introduction of Pyridine—Metal-Catalyzed C—H Arylation

The 6-amino-3-pyrid-4-ylimidazo[1,2-b]pyridazine derivatives of general formula (I) in which $R_2$, $R_3$, A, L, B, $R_7$ and $R_8$ are as defined above may also be prepared from a 6-aminoimidazo[1,2-b]pyridazine derivative of general formula (IId) in which $R_2$, A, L, B, $R_7$ and $R_8$ are as defined above, by metal-catalyzed C—H arylation with a 4-iodopyridine of general formula (IVd) in which $R_3$ is as defined above and X represents an iodine atom. This coupling may be performed in the presence of a catalyst such as palladium acetate and of a mineral base such as potassium carbonate, and in a polar aprotic solvent such as dimethylformamide.

Scheme 1, route 4: Introduction of Pyridine—Coupling of "Stille" or "Suzuki" Type The 6-amino-3-pyrid-4-ylimidazo[1,2-b]pyridazine derivatives of general formula (I) in which $R_2$, $R_3$, A, L, B, $R_7$ and $R_8$ are as defined above may also be prepared from a 6-amino-3-iodo- or 3-bromo-imidazo[1,2-b]pyridazine derivative of general formula (IIc), in which $R_2$, A, L, B, $R_7$ and $R_8$ are as defined above and X represents a bromine or iodine atom, via coupling under Stille or Suzuki conditions with a stannane or a pyridine boronate of general formula (IVc) in which $R_3$ is as defined above and M represents a trialkylstannyl group, usually a tributylstannyl group or a dihydroxyboryl or dialkyloxyboryl group, usually a 4,4,5,5-tetramethyl-1,3,3,2-dioxaborolan-2-yl group.

The couplings according to the Stille method are performed, for example, by heating in the presence of a catalyst such as tetrakis(triphenylphosphine)palladium or copper iodide in a solvent such as N,N-dimethylacetamide.

The couplings according to the Suzuki method are performed, for example, by heating in the presence of a catalyst such as [1,1'-bis(diphenylphosphino)ferrocene]dichloropalladium and of a mineral base such as cesium carbonate in a solvent mixture such as tetrahydrofuran and water.

Particular Synthetic Strategies
1. Synthetic Strategy when R$_3$=H, alkyl

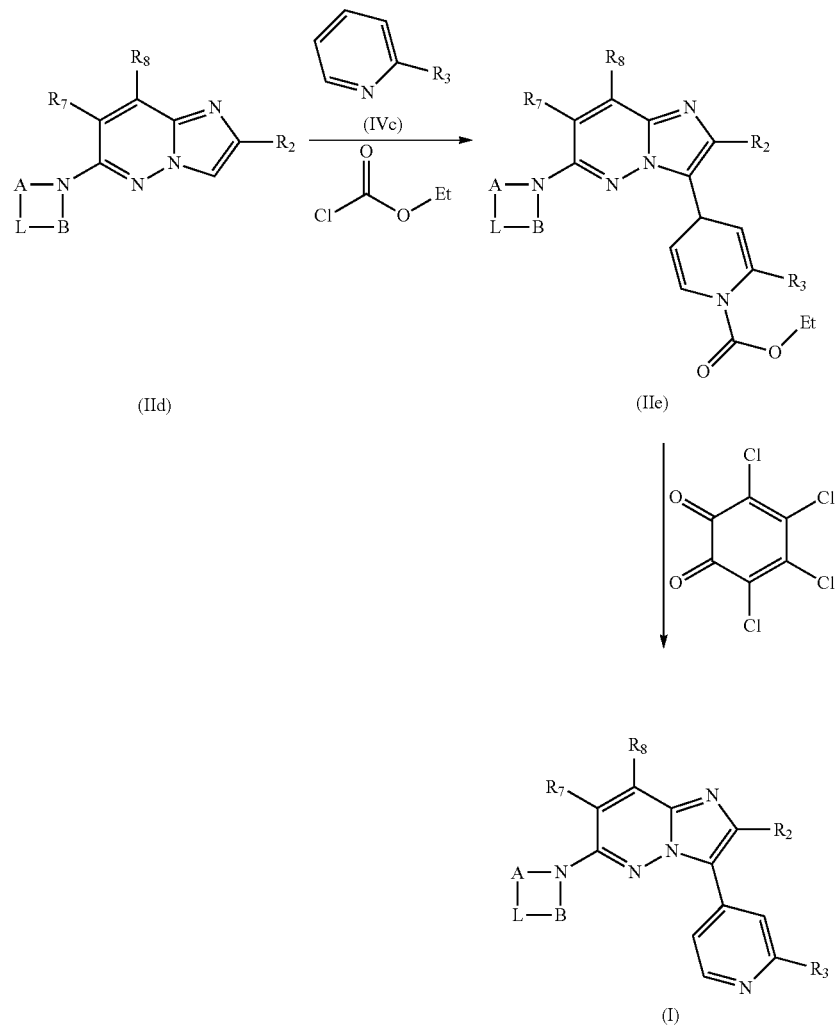

Specifically, according to Scheme 2, the 6-amino-3-pyrid-4-ylimidazo[1,2-b]pyridazine derivatives of general formula (I) in which R$_2$, A, L, B, R$_7$ and R$_8$ are as defined above, and in which R$_3$ represents a hydrogen atom or a group C$_{1-3}$-alkyl, may be prepared in two steps from a 6-aminoimidazo[1,2-b]pyridazine derivative of general formula (IId) as defined above. Thus, the reaction of a 6-aminoimidazo[1,2-b]pyridazine derivative of general formula (IId) with a mixture of a pyridine derivative of general formula (IVe) in which R$_3$ represents a hydrogen atom or a group C$_{1-3}$-alkyl, and of an alkyl chloroformate, for example ethyl chloroformate, leads to the derivative of general formula (IIe) in which R$_2$, A, L, B, R$_7$ and R$_8$ are as defined above and in which R$_3$ represents a hydrogen atom or a group C$_{1-3}$-alkyl. The derivative of general formula (IIe) is then oxidized using ortho-chloranil in a solvent such as toluene to give the 6-amino-3-pyrid-4-ylimidazo[1,2-b]pyridazine derivatives of general formula (I) in which R$_2$, A, L, B, R$_7$ and R$_8$ are as defined above and in which R$_3$ represents a hydrogen atom or a group C$_{1-3}$-alkyl.

2. Synthetic Strategies when R$_3$=NH$_2$, NH—C$_{1-3}$ alkyl, N(—C$_{1-3}$ alkyl)(C$_{1-3}$ alkyl), hydroxyl, C$_{1-3}$ alkyloxy.

Scheme 3

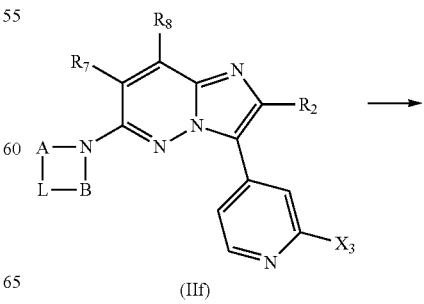

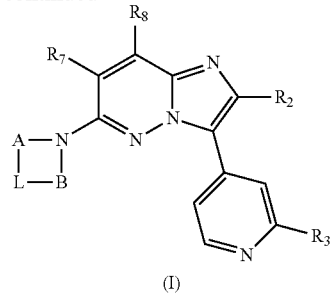

(I)

According to Scheme 3, the 6-amino-3-pyrid-4-ylimidazo[1,2-b]pyridazine derivatives of general formula (I) in which $R_2$, A, L, B, $R_7$ and $R_8$ are as defined above and in which $R_3$ represents an amino, $C_{1-3}$-monoalkylamine, or di-$C_{1-3}$ alkylamine, hydroxyl or $C_{1-3}$ alkyloxy group may be prepared from a 6-amino-3-pyrid-4-ylimidazo[1,2-b]pyridazine derivative of general formula (IIf) in which $R_2$, A, L, B, $R_7$ and $R_8$ are as defined above and in which $X_3$ represents a halogen atom or a leaving group.

When $R_3$ represents an amino, $C_{1-3}$ monoalkylamine or di-$C_{1-3}$ alkylamine group, the reaction may be performed by nucleophilic substitution using the corresponding primary or secondary amine in an aprotic solvent such as N-methylpyrrolidone.

When $R_3$ represents an amino group, the reaction may also be performed in two steps by coupling with benzhydrylideneamine in the presence of a catalyst such as tris(dibenzylideneacetone)dipalladium(0), a base such as sodium tert-butoxide and a phosphonic ligand such as (±)-2,2'-bis(diphenylphosphino)-1,1'-binaphthyl, followed by hydrolysis of the benzhydrylidene using an acid such as hydrochloric acid.

When $R_3$ represents a hydroxyl group, the reaction may be performed by heating in the presence of sodium hydroxide or potassium hydroxide in a solvent such as tert-butanol.

When $R_3$ represents a group $C_{1-3}$ alkoxy, the reaction may be performed by treatment using the corresponding sodium or potassium $C_{1-3}$ alkoxide in a solvent such as N-methylpyrrolidone.

Synthesis of the Precursors

Scheme 4

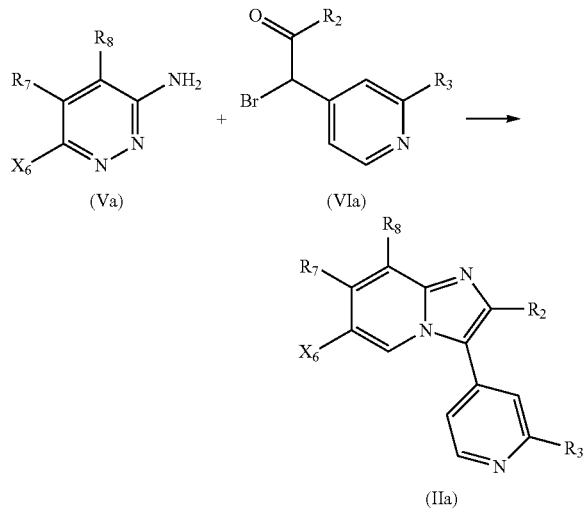

(Va) (VIa)

(IIa)

According to Scheme 4, the 3-pyrid-4-ylimidazo[1,2-b]pyridazine derivatives of general formula (IIa), in which $R_2$, $R_3$, $R_7$ and $R_8$ are as defined above and $X_6$ represents a leaving group such as a halogen, may be prepared by condensation between a pyridazin-3-ylamine derivative of general formula (Va) in which $R_7$ and $R_8$ are as defined above and $X_6$ represents a halogen or a leaving group and a 2-bromo-2-(pyrid-4-yl)ethan-1-one derivative of general formula (VIa) in which $R_2$ and $R_3$ are as defined above.

The reaction may be performed by heating the reagents in a polar solvent such as aliphatic alcohols, for example ethanol or butanol.

Scheme 5a

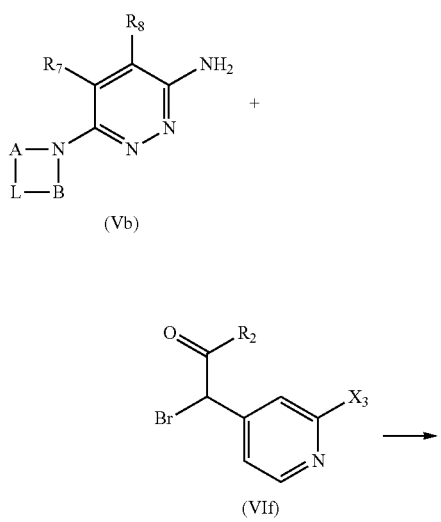

(Vb)

(VIf)

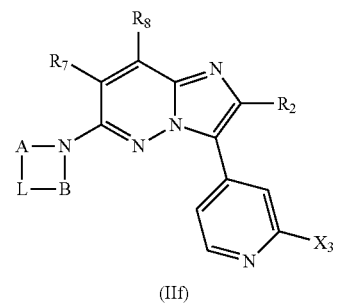

(IIf)

According to Scheme 5a, the 3-pyrid-4-ylimidazo[1,2-b]pyridazine derivatives of general formula (IIf), in which $R_2$, A, L, B, $R_7$ and $R_8$ are as defined above and $X_3$ represents a leaving group such as a halogen, may be prepared by condensation between a pyridazin-3-ylamine derivative of general formula (Vb) in which A, L, B, $R_7$ and $R_8$ are as defined above and a 2-bromo-2-(pyrid-4-yl)ethan-1-one derivative of general formula (VIf) in which $R_2$ is as defined above and $X_3$ represents a halogen or a leaving group.

This reaction may be performed by heating the reagents in a polar solvent such as aliphatic acids, for example ethanol or butanol.

Scheme 5b

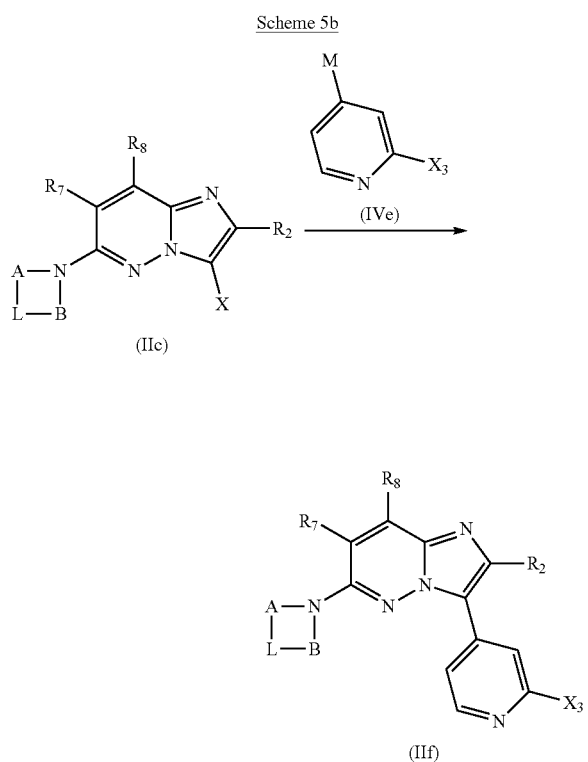

According to Scheme 5b, the 3-pyrid-4-ylimidazo[1,2-b]pyridazine derivatives of general formula (IIf) as defined above may also be obtained from a 6-amino-3-iodo- or 3-bromo-imidazo[1,2-b]pyridazine derivative of general formula (IIc), in which $R_2$, A, L, B, $R_7$ and $R_8$ are as defined above and X represents a bromine or iodine atom, by coupling under the Stille or Suzuki conditions with a stannane or a pyridine boronate of general formula (IVe) in which $X_3$ represents a halogen or a leaving group and M represents a trialkylstannyl group, usually a tributylstannyl group or a dihydroxyboryl or dialkyloxyboryl group, usually a 4,4,5,5-tetramethyl-1,3,3,2-dioxaborolan-2-yl group.

The couplings according to the Stille method are performed, for example, by heating in the presence of a catalyst such as tetrakis(triphenylphosphine)palladium or copper iodide in a solvent such as N,N-dimethylacetamide.

The couplings according to the Suzuki method are performed, for example, by heating in the presence of a catalyst such as [1,1'-bis(diphenylphosphino)ferrocene]dichloropalladium and of a mineral base such as cesium carbonate in a mixture of solvents such as tetrahydrofuran and water.

Scheme 6

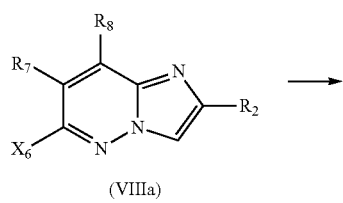

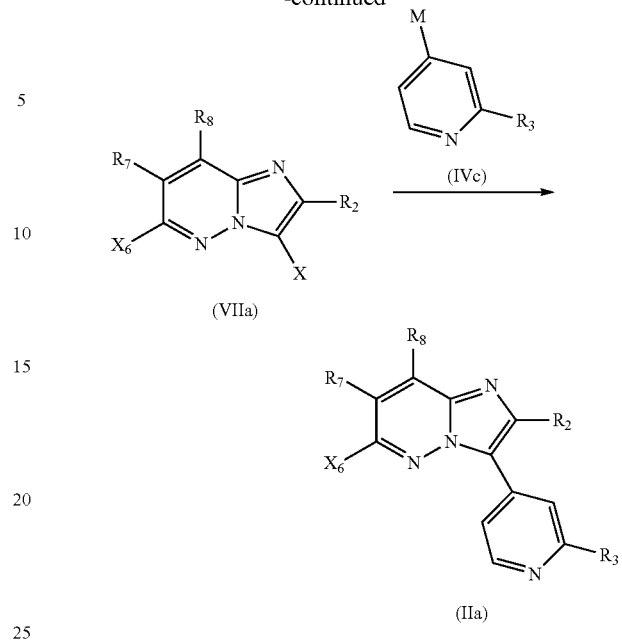

According to Scheme 6, the 3-pyrid-4-ylimidazo[1,2-b]pyridazine derivatives of general formula (IIa), in which $R_2$, $R_3$, $R_7$ and $R_8$ are as defined above and $X_6$ represents a leaving group such as a halogen may also be prepared in two steps from an imidazo[1,2-b]pyridazine derivative of general formula (VIIIa) in which $R_2$, $R_7$ and $R_8$ are as defined above and $X_6$ represents a leaving group.

The bromination or iodination of an imidazo[1,2-b]pyridazine derivative of general formula (VIIIa), in which $R_2$, $R_7$ and $R_8$ are as defined above and $X_6$ represents a halogen atom or a leaving group, leads to a 3-bromo- or iodoimidazo[1,2-b]pyridazine derivative of general formula (VIIa), in which $R_2$, $R_7$ and $R_8$ are as defined above and $X_6$ represents a halogen or a leaving group and X represents a bromine or iodine atom. This reaction may be performed using N-bromo- or iodosuccinimide or iodine monochloride in a polar solvent such as acetonitrile, tetrahydrofuran, methanol or chloroform.

The 3-bromo or iodoimidazo[1,2-b]pyridazine derivative of general formula (VIIa) obtained is then regioselectively coupled according to the Stille or Suzuki methods with a stannane or a pyridine boronate of general formula (IVc) in which $R_3$ is as defined above and M represents a trialkylstannyl group, usually a tributylstannyl group or a group dihydroxyboryl or dialkyloxyboryl group, usually a 4,4,5,5-tetramethyl-1,3,2-dioxaborolan-2-yl group.

The couplings according to the Stille method are performed, for example, by heating in the presence of a catalyst such as tetrakis(triphenylphosphine)palladium or copper iodide in a solvent such as dimethylacetamide.

The couplings according to the Suzuki method are performed, for example, by heating in the presence of a catalyst such as [1,1'-bis(diphenylphosphino)ferrocene]dichloropalladium and of a mineral base such as cesium carbonate in a mixture of solvents such as tetrahydrofuran and water.

The imidazo[1,2-b]pyridazine derivatives of general formula (VIIIa) in which $R_2$, $R_7$ and $R_8$ are as defined above and $X_6$ represents a leaving group are known or may be prepared by analogy with methods described in the literature (Abignente, Enrico; Caprariis, Paolo de; Patscot, Rosaria; Sacchi, Antonella; J. Heterocycl. Chem.; 23; 1986; 1031-1034; Barlin, Gordon B.; Davies, Les P.; Ireland, Stephen J.; Ngu, Maria M. L.; Zhang, Jiankuo; Aust. J. Chem.; EN; 45; 4; 1992; 731-749; Mourad, Alaa E.; Wise, Dean S.; Townsend, Leroy B.; J. Heterocycl. Chem.; 30; 5; 1993; 1365-1372; Pollak et al.; Tetrahedron; 24; 1968; 2623; Hervet, Maud; Galtier, Christophe; Enguehard, Cecile; Gueiffier, Alain; Debouzy, Jean-Claude; Journal of Heterocyclic Chemistry (2002), 39(4), 737-742).

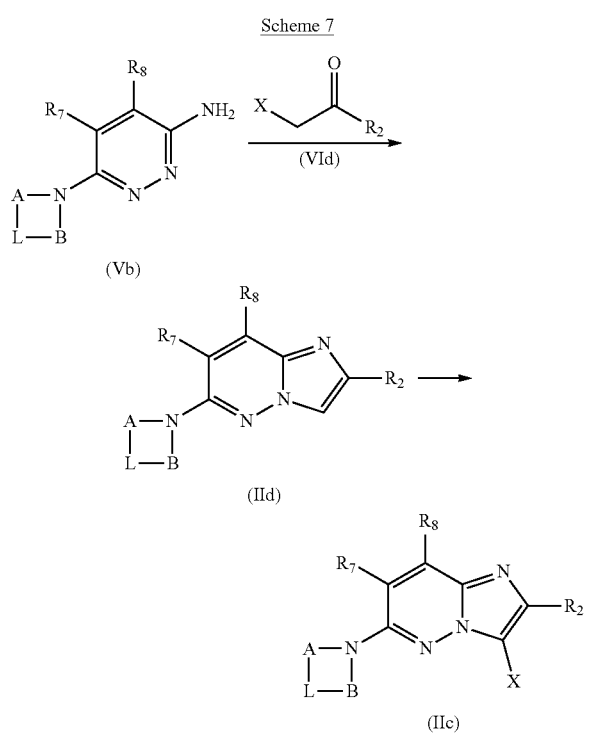

Scheme 7

According to Scheme 7, the 6-amino-3-pyrid-4-ylimidazo[1,2-b]pyridazine derivatives of general formula (IIc) in which $R_2$, A, L, B, $R_7$ and $R_8$ are as defined above and in which X represents a bromine or iodine atom are prepared by bromination or iodination of a 6-amino-3-pyrid-4-ylimidazo[1,2-b]pyridazine starting derivative of general formula (IId) in which $R_2$, A, L, B, $R_7$ and $R_8$ are as defined above.

This reaction may be performed using N-bromo- or iodosuccinimide or iodine monochloride in a polar aprotic solvent such as acetonitrile or tetrahydrofuran.

The 6-amino-3-pyrid-4-ylimidazo[1,2-b]pyridazine derivatives of general formula (IId) in which $R_2$, A, L, B, $R_7$ and $R_8$ are as defined above are known or may be prepared by analogy with methods described in the literature (for example Watanabe et al.; Synthesis; 1977; 761; Jurgee et al.; J. Heterocycl. Chem.; 12; 1975; 253.255; Werbel, L. M.; Zamora, M. L.; J. Heterocycl. Chem.; 2; 1965; 287-290; Yoneda et al.; Chem. Pharm. Bull.; 12; 1964; 1351.1353.1354; Tomoyasu; Iizawa, Yuji; Okonogi, Kenji; Miyake, Akio; J. Antibiot.; 53; 10; 2000; 1053-1070).

They are usually prepared by condensation between a pyridazin-3-ylamine derivative of general formula (Vb) in which A, L, B, $R_7$ and $R_8$ are as defined above and a 2-bromo, chloro- or iodoethan-1-one derivative of general formula (VId) in which $R_2$ is as defined above. The reaction may be performed by heating the reagents in a polar solvent such as ethanol or butanol.

In the preceding synthetic schemes, the starting compounds and the reagents, when their mode of preparation is not described, are commercially available or described in the literature, or alternatively may be prepared according to methods that are described therein or that are known to those skilled in the art.

Protecting Groups

For the compounds of general formula (I), (IIc), (IId), (IIe), (IIf), (IIIa) and (Vb) as defined above and when the group N-A-L-B comprises a primary or secondary amine function, this function may optionally be protected during the synthesis with protecting groups known to those skilled in the art, for example a benzyl or a t-butyloxycarbonyl.

For the compounds of general formula (I), (IIa), (IVc), (IVd), (VIa) and (VIb) as defined above and when the group $R_3$ comprises a primary or secondary amine function, this function may be optionally protected with protecting groups known to those skilled in the art, for example a benzyl or a t-butyloxycarbonyl.

The products of general structure (I) as defined above are obtained according to the processes described after a final additional step of deprotection of the protecting group according to the usual conditions known to those skilled in the art.

The examples that follow describe the preparation of certain compounds in accordance with the invention. These examples are not limiting and serve merely to illustrate the present invention. The numbers of the illustrated compounds refer to those given in the table below, which illustrates the chemical structures and physical properties of a number of compounds according to the invention.

EXAMPLE 1

(Compound 50): 2-(4-Fluorophenyl)-6-(4-methylpiperazin-1-yl)-3-pyrid-4-ylimidazo[1,2-b]pyridazine

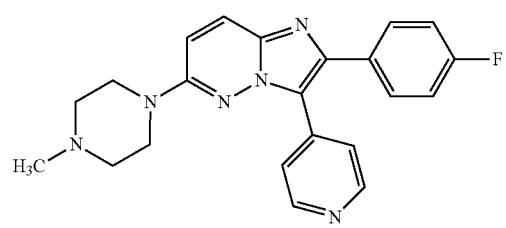 [SMILES: CN1CCN(c2ccc3nc(-c4ccc(F)cc4)c(-c4ccncc4)n3n2)CC1]

a) Synthesis According to the Process of Scheme 1, Route 4:

Step 1.1a. 2-(4-Fluorophenyl)-6-(4-methylpiperazin-1-yl)imidazo[1,2-b]pyridazine

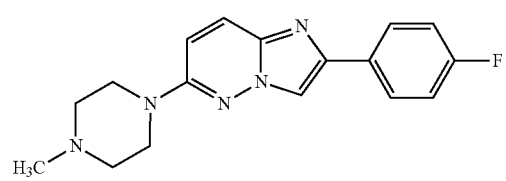 [SMILES: CN1CCN(c2ccc3nc(-c4ccc(F)cc4)cn3n2)CC1]

After heating a suspension of 32 g (97.4 mmol) of 6-chloro-2-(4-fluorophenyl)imidazo[1,2-b]pyridazine (CAS No.: 2069-47-8) in 200 ml of 1-methylpiperazine at 160° C. for 16 hours, the mixture is poured into 1.5 L of water. The yellowish precipitate formed is separated out by filtration and rinsed with cold isopropanol and then with diisopropyl ether. 30 g of a beige-colored powder are thus isolated after drying under vacuum.

m.p.: 190° C.

$^1$H NMR (CDCl$_3$) δ: 7.85 (s; 1H), 7.8 (m, 2H), 7.60 (d, 1H), 7.05 (pseudo t, 2H), 6.75 (d, 1H), 3.45 (m, 4H), 2.50 (m, 4H), 2.30 (s, 3H) ppm.

Step 1.2a. 2-(4-Fluorophenyl)-3-iodo-6-(4-methylpiperazin-1-yl)imidazo[1,2-b]pyridazine

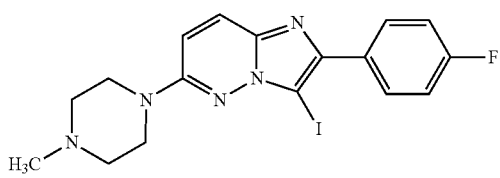 [SMILES: CN1CCN(c2ccc3nc(-c4ccc(F)cc4)c(I)n3n2)CC1]

To a solution, cooled to about 5° C., of 31.0 g (99.6 mmol) of 2-(4-fluorophenyl)-6-(4-methylpiperazin-1-yl)imidazo[1,2-b]pyridazine in chloroform is rapidly added dropwise a solution of 64.7 g (398 mmol) of iodine monochloride in 150 mL of methanol. Mild exothermicity and the formation of a precipitate during the addition are observed. After cooling to room temperature and stirring for 30 minutes, the mixture is poured into 2 L of aqueous 5% sodium thiosulfate solution saturated with sodium bicarbonate. After vigorous stirring until the mixture has decolorized, the product is extracted with chloroform. The organic phase is separated out, dried over sodium sulfate, filtered and concentrated under reduced pressure to give a brown solid. This solid is triturated in a mixture of 400 mL of diisopropyl ether and 50 mL of isopropanol at reflux. After cooling, 40 g of a beige-colored powder are isolated by filtration through a sinter funnel and drying under vacuum.

m.p.: 180° C.

$^1$H NMR (CDCl$_3$) δ: 8.05 (pseudo dd; 2H), 7.65 (d, 1H), 7.15 (pseudo t, 2H), 6.85 (d, 1H), 3.65 (m, 4H), 2.55 (m, 4H), 2.35 (s, 3H) ppm.

Step 1.3a. 2-(4-Fluorophenyl)-6-(4-methylpiperazin-1-yl)-3-pyrid-4-ylimidazo[1,2-b]pyridazine

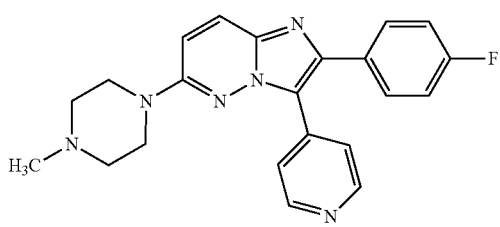 [SMILES: CN1CCN(c2ccc3nc(-c4ccc(F)cc4)c(-c4ccncc4)n3n2)CC1]

To a suspension of 2.80 g (6.40 mmol) of 2-(4-fluorophenyl)-3-iodo-6-(4-methylpiperazin-1-yl)imidazo[1,2-b]pyridazine in 200 mL of a mixture of dimethoxyethane and water (9:1), are added 1.36 g (12.8 mmol) of sodium bicarbonate and 0.95 g (7.7 mmol) of (pyrid-4-yl)boronic acid. After sparging with a stream of argon for a few moments, 0.21 g (0.26 mmol) of a complex of [1,1'-bis(diphenylphosphino) ferrocene]dichloropalladium(II) and dichloromethane (PdCl$_2$(dppf).CH$_2$Cl$_2$) is added and the reaction mixture is refluxed under argon for 18 hours. A further 0.95 g (7.7 mmol) of (pyrid-4-yl)boronic acid, 0.21 g (0.26 mmol) of [1,1'-bis (diphenylphosphino)ferrocene]dichloropalladium(II) dichloromethane and 10 mL of water are then added. Heating is continued for 24 hours. The solvent is then evaporated off under reduced pressure and the brown residue is triturated with aqueous 3N hydrochloric acid and then filtered on a Büchner funnel. The aqueous phase is washed twice with diethyl ether and then cautiously neutralized, using aqueous ammonia diluted with ice, to basic pH. The product is extracted with chloroform, the organic phase is dried over sodium sulfate and filtered, and the solvent is evaporated off to give 2.5 g of a yellowish powder.

The product is purified by chromatography on silica gel, eluting with a mixture of dichloromethane, methanol and aqueous ammonia (96/4/0.4) to give 2.3 g of a whitish powder. The product is recrystallized from a mixture of 130 mL of acetonitrile and 10 to 30 mL of isopropanol.

1.1 g of a whitish powder are isolated.

m.p.: 248-250° C.

$^1$H NMR (CDCl$_3$) δ: 8.65 (d; 2H), 7.85 (d, 1H), 7.5-7.7 (m, 4H), 7.05 (pseudo t, 2H), 6.95 (d, 1H), 3.55 (m, 4H), 2.55 (m, 4H), 2.40 (s, 3H) ppm.

b) Synthesis According to the Process of Scheme 2:

Step 1.1b. Ethyl 4-[2-(4-fluorophenyl)-6-(4-methylpiperazin-1-yl)imidazo[1,2-b]pyridazin-3-yl]-4H-pyridine-1-carboxylate

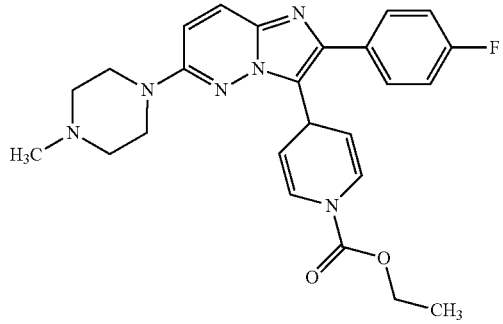 [SMILES: CCOC(=O)N1C=CC(c2c(-c3ccc(F)cc3)nc3ccc(N4CCN(C)CC4)nn23)C=C1]

To a suspension, cooled to about 0° C., of 3.24 g (10.4 mmol) of 2-(4-fluorophenyl)-6-(4-methylpiperazin-1-yl) imidazo[1,2-b]pyridazine in 7.5 mL of pyridine is added dropwise a solution of 5.0 mL (52 mmol) of ethyl chloroformate. After cooling to room temperature, 10 mL (104 mmol) of ethyl chloroformate and 15 mL of pyridine are added in two portions.

After 18 hours, the mixture is diluted with 50 mL of dichloromethane and 20 mL (208 mmol) of ethyl chloroformate are added in three portions over 5 hours. 350 mL of water are then added, and the organic phase is separated out and washed twice with water, dried over sodium sulfate and concentrated under reduced pressure to give 4.5 g of a brownish solid. This solid is triturated in diethyl ether to give 3.5 g of beige-colored crystals. The solid is dissolved in dichloromethane and purified by chromatography on a column of silica gel, eluting with a mixture of 10% methanol in dichloromethane, to give 2.95 g of pale yellow crystals after trituration in diethyl ether, filtering through a sinter funnel and drying under vacuum.

m.p.: 179.9° C.

$^1$H NMR (DMSO-d$_6$) δ: 7.80 (d; 2H), 7.65 (m, 2H), 7.2 (m, 3H), 6.95 (d, 1H), 4.8-5.0 (m, 3H), 4.25 (q, 2H), 3.40 (m, 4H), 2.40 (m, 4H), 2.20 (s, 3H), 1.30 (t, 3H) ppm.

Step 1.2b. 2-(4-Fluorophenyl)-6-(4-methylpiperazin-1-yl)-3-pyrid-4-ylimidazo[1,2-b]pyridazine

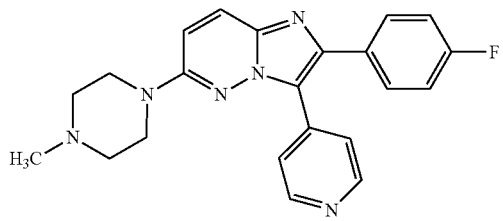 [SMILES: CN1CCN(c2ccc3nc(-c4ccc(F)cc4)c(-c4ccncc4)n3n2)CC1]

To a suspension of 1.00 g (2.16 mmol) of ethyl 4-[2-(4-fluorophenyl)-6-(4-methylpiperazin-1-yl)imidazo[1,2-b]pyridazin-3-yl]-4H-pyridine-1-carboxylate in 35 mL of toluene is added a solution of 0.65 g (2.6 mmol) of ortho-chloranil in 6 mL of toluene. After reaction for 6 hours, 60 mL of 1N sodium hydroxide are added and the product is extracted with ethyl acetate. The organic phase is washed with saturated aqueous sodium chloride solution and dried over sodium sulfate, and the solvent is evaporated off under reduced pressure. 1.2 g of solid are thus recovered, and are purified on a column of silica gel, eluting with a stepwise gradient of 3% to 15% methanol in dichloromethane. The product obtained is washed with diisopropyl ether and recrystallized from isopropyl alcohol to give 0.47 g of crystals after filtering off and drying under reduced pressure.

m.p.: 294-296° C.

$^1$H NMR (CDCl$_3$) δ: 8.65 (d; 2H), 7.85 (d, 1H), 7.5-7.7 (m, 4H), 7.05 (pseudo t, 2H), 6.95 (d, 1H), 3.55 (m, 4H), 2.55 (m, 4H), 2.40 (s, 3H) ppm.

c) Synthesis According to Scheme 1, Route 3:

Step 1.1c. 2-(4-Fluorophenyl)-6-(4-methylpiperazin-1-yl)-3-pyrid-4-ylimidazo[1,2-b]pyridazine

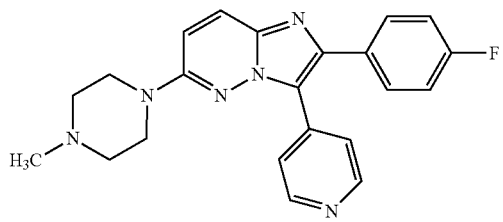 [SMILES: CN1CCN(c2ccc3nc(-c4ccc(F)cc4)c(-c4ccncc4)n3n2)CC1]

A mixture of 0.90 g (2.89 mmol) of 2-(4-fluorophenyl)-6-(4-methylpiperazin-1-yl)imidazo[1,2-b]pyridazine (Synthesis, 2001, 4, 595-600), 0.71 g (3.5 mmol) of 4-iodopyridine, 0.032 g (0.14 mmol) of palladium acetate and 0.48 g (3.5 mmol) of potassium carbonate in 18 mL of dimethylformamide is heated at 135° C. for 18 hours. After cooling, the reaction medium is poured into water and the product is extracted with ethyl acetate. The organic phase is washed with water and dried over sodium sulfate, and the solvent is evaporated off under reduced pressure. The residue is purified on a column of silica gel, eluting with a mixture of dichloromethane, methanol and aqueous ammonia (95/5/0.5) to give 0.5 g of crystals after recrystallization from acetonitrile, filtering off and drying under reduced pressure.

m.p.: 250° C.

$^1$H NMR (CDCl$_3$) δ: 8.65 (d, 2H), 7.85 (d, 1H), 7.5-7.7 (m, 4H), 7.05 (pseudo t, 2H), 6.95 (d, 1H), 3.55 (m, 4H), 2.55 (m, 4H), 2.40 (s, 3H) ppm.

EXAMPLE 2

(Compound 3): 2-(4-Fluorophenyl)-7,8-dimethyl-6-piperazin-1-yl-3-pyrid-4-ylimidazo[1,2-b]pyridazine

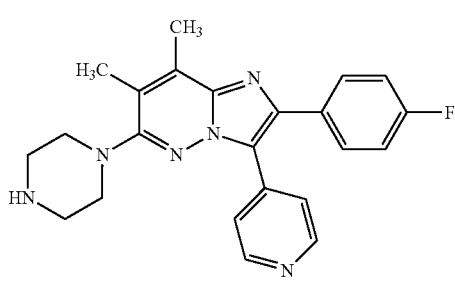 [SMILES: Cc1c(N2CCNCC2)nn2c(-c3ccncc3)c(-c3ccc(F)cc3)nc2c1C]

Synthesis According to Scheme 1, Route 4:

Step 2.1. 6-Chloro-2-(4-fluorophenyl)-7,8-dimethylimidazo[1,2-b]pyridazine

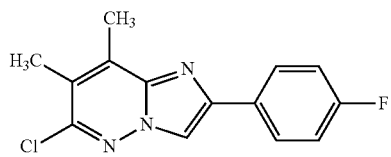 [SMILES: Cc1c(Cl)nn2cc(-c3ccc(F)cc3)nc2c1C]

A solution of 13 g (85 mmol) of 3-amino-6-chloro-4,5-dimethylpyridazine and 23 g (107 mmol) of 2-bromo-1-(4-fluorophenyl)ethanone in 130 mL of ethanol is refluxed for 16 hours. After cooling, the solvent is evaporated off under reduced pressure and the residue is taken up in chloroform. The organic phase is washed with diluted aqueous ammonia, dried over sodium sulfate and concentrated under reduced pressure to give a brown solid. This solid is triturated in acetone to give 19.2 g of a beige-colored powder.

Yield: 84% m.p.: 172-174° C.

$^1$H NMR (CDCl$_3$) δ: 8.10 (s, 1H), 7.95 (m, 2H), 7.15 (pseudo t, 2H), 2.70 (s, 3H), 2.45 (s, 3H) ppm.

Step 2.2. 2-(4-Fluorophenyl)-7,8-dimethyl-6-piperazin-1-ylimidazo[1,2-b]pyridazine

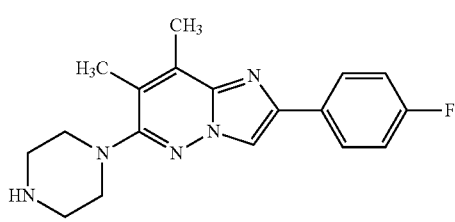 [SMILES: Cc1c(N2CCNCC2)nn2cc(-c3ccc(F)cc3)nc2c1C]

A mixture of 1.4 g (5.08 mmol) of 6-chloro-2-(4-fluorophenyl)-7,8-dimethylimidazo[1,2-b]pyridazine and 8.7 g (100 mmol) of piperazine is heated at 150° C. for 3 hours in a reactor. The medium is then poured into water and the precipitate formed is isolated by filtration. The product is then recrystallized from a mixture of diisopropyl ether and isopropanol to give 1.15 g of a white powder.

Yield: 70%.

¹H NMR (CDCl₃) δ: 8.00 (s; 1H), 7.95 (pseudo dd, 2H), 7.15 (pseudo t, 2H), 3.15 (m, 8H), 2.65 (s, 3H), 2.35 (s, 3H) ppm.

Step 2.3. 2-(4-Fluorophenyl)-3-iodo-7,8-dimethyl-6-piperazin-1-ylimidazo[1,2-b]pyridazine

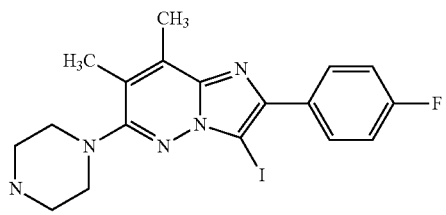 [SMILES: Cc1c(N2CCNCC2)nn2c(I)c(-c3ccc(F)cc3)nc2c1C]

To a solution, cooled to 0° C., of 1.15 g (3.53 mmol) of 2-(4-fluorophenyl)-7,8-dimethyl-6-piperazin-1-ylimidazo[1,2-b]pyridazine in 20 mL of dichloromethane, is added dropwise a solution of 2.29 g (14.1 mmol) of iodine monochloride in 5 mL of methanol and the medium is stirred for 30 minutes at room temperature. 5% sodium thiosulfate solution is then added and the medium is basified by addition of sodium hydrogen carbonate.

The product is extracted with dichloromethane, the organic phase is dried over sodium sulfate and filtered, and the solvent is evaporated off to give 0.82 g of a yellow powder after crystallization from diethyl ether and drying.

Yield: 51%.

¹H NMR (CDCl₃) δ: 8.15 (pseudo dd, 2H), 7.35 (pseudo t, 2H), 3.15 (m, 4H), 2.95 (m, 4H), 2.5 (s, 3H), 2.30 (s, 3H) ppm.

Step 2.4. tert-Butyl 4-[2-(4-fluorophenyl)-3-iodo-7,8-dimethylimidazo[1,2-b]pyridazin-6-yl]piperazine-1-carboxylate

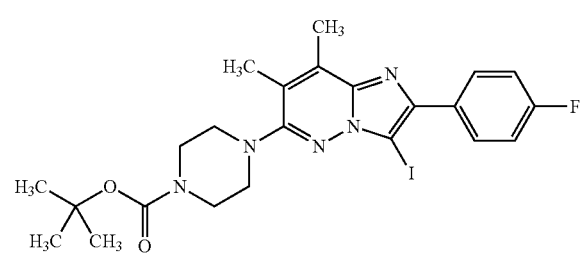 [SMILES: Cc1c(N2CCN(C(=O)OC(C)(C)C)CC2)nn2c(I)c(-c3ccc(F)cc3)nc2c1C]

A solution of 0.70 g (1.55 mmol) of 2-(4-fluorophenyl)-3-iodo-7,8-dimethyl-6-piperazin-1-ylimidazo[1,2-b]pyridazine and 19 mg (0.16 mmol) of dimethylaminopyridine in 10 mL of tetrahydrofuran is treated with 0.41 g (1.9 mmol) of di-tert-butyl carbonate for 1 hour. The solvent is then evaporated off and the solid obtained is recrystallized from acetonitrile. 0.67 g of product is thus isolated after drying.

Yield: 78%.

¹H NMR (CDCl₃) δ: 8.00 (pseudo dd, 2H), 7.10 (pseudo t, 2H), 3.60 (m, 4H), 3.15 (m, 4H), 2.55 (s, 3H), 2.25 (s, 3H), 1.40 (s, 9H) ppm.

Step 2.5. tert-Butyl 4-[2-(4-fluorophenyl)-7,8-dimethyl-3-pyrid-4-ylimidazo[1,2-b]pyridazin-6-yl]piperazine-1-carboxylate

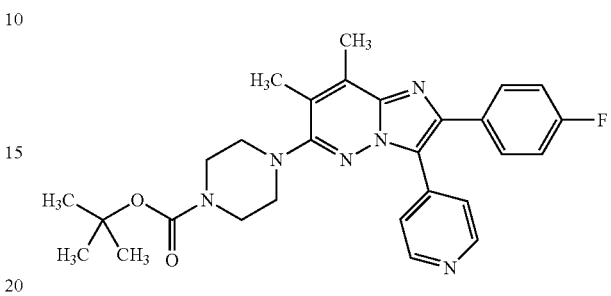

To a mixture of 0.66 g (1.2 mmol) of tert-butyl 4-[2-(4-fluorophenyl)-3-iodo-7,8-dimethylimidazo[1,2-b]pyridazin-6-yl]piperazine-1-carboxylate in 15 mL of a mixture of tetrahydrofuran and water (9:1), are added 1.17 g (3.6 mmol) of cesium carbonate and 0.31 g (1.4 mmol) of (pyrid-4-yl)boronic acid. After sparging with a stream of argon for a few moments, 88 mg (0.11 mmol) of a complex of [1,1'-bis(diphenylphosphino)ferrocene]dichloropalladium(II) and dichloromethane (PdCl₂(dppf).CH₂Cl₂) are added and the reaction mixture is refluxed under argon for 18 hours. The mixture is then poured into water and the product is extracted with dichloromethane, the organic phase is dried over sodium sulfate and filtered, and the solvent is evaporated off to give a brown solid. The product is purified by chromatography on silica gel, eluting with a mixture of ethyl acetate and cyclohexane (3/7) to give 0.44 g of a white powder.

Yield: 73%
m.p.: 231-233° C.

¹H NMR (CDCl₃) δ: 8.55 (pseudo d, 2H), 7.55-7.75 (m, 4H), 7.00 (pseudo t, 2H), 3.55 (m, 4H), 3.05 (m, 4H), 2.60 (s, 3H), 2.25 (s, 3H), 1.40 (s, 9H) ppm.

Step 2.6. 2-(4-Fluorophenyl)-7,8-dimethyl-6-piperazin-1-yl-3-pyrid-4-ylimidazo[1,2-b]pyridazine

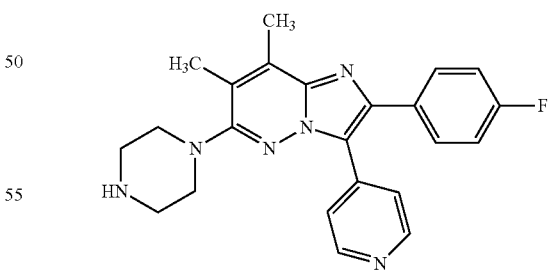

To a solution of 0.43 g (0.86 mmol) of tert-butyl 4-[2-(4-fluorophenyl)-7,8-dimethyl-3-pyrid-4-ylimidazo[1,2-b]pyridazin-6-yl]piperazine-1-carboxylate in 5 mL of dichloromethane at 0° C. is added dropwise 0.64 mL (8.6 mmol) of trifluoroacetic acid. After stirring for 4 hours at room temperature, a further 0.64 mL (8.6 mmol) of trifluoroacetic acid is added and the reaction mixture is left for 18 hours. The solvent is then removed under reduced pressure and the residue is taken up in water. The resulting aqueous phase is washed with ether and then basified by addition of aqueous sodium hydrogen carbonate solution. The product is extracted with dichloromethane, the organic phase is dried over sodium sulfate and filtered, and the solvent is evaporated off to give 0.285 g of a white powder.

Yield: 83% m.p.: 233-235° C.

$^1$H NMR (CDCl$_3$) δ: 8.60 (pseudo d, 2H), 7.55-7.75 (m, 4H), 7.05 (pseudo t, 2H), 3.00-3.2 (m, 4H), 2.65 (s, 3H), 2.35 (s, 3H) ppm.

EXAMPLE 3

(Compound 58): {4-[2-(4-Fluorophenyl)-6-(4-methylpiperazin-1-yl)imidazo[1,2-b]pyridazin-3-yl]pyrid-2-yl}dimethylamine

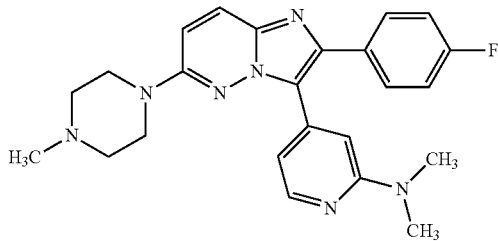 [SMILES: CN1CCN(c2ccc3nc(-c4ccc(F)cc4)c(-c4ccnc(N(C)C)c4)n3n2)CC1]

Synthesis According to Scheme 3:

Step 3.1.
6-(4-Benzylpiperazin-1-yl)pyridazin-3-ylamine

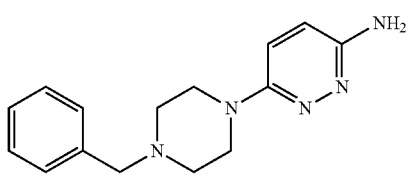 [SMILES: Nc1ccc(N2CCN(Cc3ccccc3)CC2)nn1]

48.9 g (278 mmol) of 1-benzylpiperazine and 12.0 g (92.6 mmol) of 3-amino-6-chloropyridazine are heated at 160° C. for 1 hour. The brown oil obtained is poured into 500 mL of aqueous sodium bicarbonate solution and the product is extracted with dichloromethane. The organic phase is dried and then concentrated under reduced pressure. The oil obtained is triturated in diethyl ether, and 20.5 g of a solid are isolated after filtering off and drying.

Yield: 82%.

$^1$H NMR (CDCl$_3$) δ: 7.45-7.65 (m, 6H), 7.20 (s, 1H), 5.5 (broad unresolved complex, 2H) 3.80 (s, 2H), 3.60-3.75 (m, 4H), 2.80-2.85 (m, 4H) ppm.

Step 3.2. 2-(4-Fluorophenyl)-3-(2-fluoropyrid-4-yl)-6-(4-methylpiperazin-1-yl)imidazo[1,2-b]pyridazine Synthesis According to Scheme 5a:

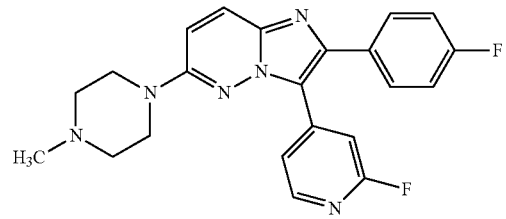 [SMILES: CN1CCN(c2ccc3nc(-c4ccc(F)cc4)c(-c4ccnc(F)c4)n3n2)CC1]

A mixture of 0.77 g (2.5 mmol) of 2-bromo-1-(4-fluorophenyl)-2-(2-fluoropyrid-4-yl)ethanone (CAS No.: 302839-10-7) and 0.57 g (3.0 mmol) of 6-(4-methylpiperazin-1-yl)pyridazin-3-ylamine (CAS No.: 66346-94-9) in 15 mL of ethanol is refluxed for 1 hour 30 minutes. After cooling, the medium is taken up in chloroform and washed with saturated aqueous sodium bicarbonate solution.

The organic phase is then dried over sodium sulfate and concentrated under reduced pressure to give an orange-colored solid.

The solid obtained is purified by chromatography on silica gel (7 g), eluting with a mixture of dichloromethane, methanol and aqueous ammonia (95/5/0.5). The product obtained is crystallized from refluxing acetonitrile to give 0.76 g of a white powder after filtering off and drying.

m.p.: 250-255° C.

$^1$H NMR (CDCl$_3$) δ: 8.20 (d, 1H), 7.80 (d, 1H), 7.60 (m, 2H), 7.4 (m, 2H), 7.10 (m, 2H), 6.95 (d, 1H), 3.60 (m, 4H), 2.60 (m, 4H), 2.40 (s, 3H) ppm.

Step 3.3. {4-[2-(4-Fluorophenyl)-6-(4-methylpiperazin-1-yl)imidazo[1,2-b]pyridazin-3-yl]pyrid-2-yl}dimethylamine

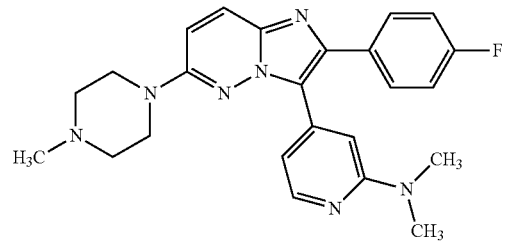 [SMILES: CN1CCN(c2ccc3nc(-c4ccc(F)cc4)c(-c4ccnc(N(C)C)c4)n3n2)CC1]

0.10 g (0.25 mmol) of 2-(4-fluorophenyl)-3-(2-fluoropyrid-4-yl)-6-(4-methylpiperazin-1-yl)imidazo[1,2-b]pyridazine and 10 mL of dimethylamine are introduced into an autoclave. The mixture is heated at 150° C. overnight and then cooled and poured into water. The product is extracted with chloroform, and the organic phase is dried over sodium sulfate and then concentrated under reduced pressure to give a solid. This solid is crystallized and recrystallized from acetonitrile to give 0.028 g of a white powder after cooling, filtering off and drying.

m.p.: 180-183° C.

$^1$H NMR (CDCl$_3$) δ: 8.15 (d, 1H), 7.70 (d, 1H), 7.70 (m, 2H), 6.95 (m, 2H), 6.80 (m, 2H), 6.70 (d, 1H), 3.50 (m, 4H), 3.00 (s, 6H), 2.50 (m, 4H), 2.30 (s, 3H) ppm.

EXAMPLE 4

(Compound 59): 2-(4-Fluorophenyl)-3-(2-methoxy-pyrid-4-yl)-6-(4-methylpiperazin-1-yl)imidazo[1,2-b]pyridazine

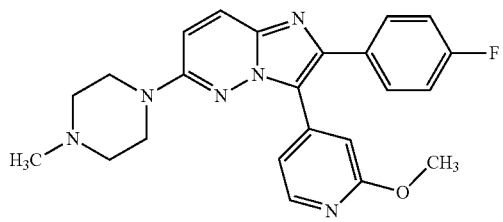 [SMILES: COc1cc(-c2c(-c3ccc(F)cc3)nc3ccc(N4CCN(C)CC4)nn23)ccn1]

Synthesis According to Scheme 3:

To a solution under argon of 0.10 g (0.25 mmol) of 2-(4-fluorophenyl)-3-(2-fluoropyrid-4-yl)-6-(4-methylpiperazin-1-yl)imidazo[1,2-b]pyridazine in N-methylpyrrolidone is added 0.65 mL (3.4 mmol) of sodium methoxide at 30% by weight in methanol. After stirring for 4 days at room temperature, the medium is poured into 200 mL of water and the product is extracted with ethyl acetate. The organic phase is dried over sodium sulfate and then concentrated under reduced pressure to give a pale yellow solid.

The solid obtained is purified by chromatography on silica gel (7 g), eluting with a mixture of dichloromethane, methanol and aqueous ammonia (95/05/0.5). The product obtained is crystallized from refluxing acetonitrile to give 0.04 g of a white powder after cooling, filtering off and drying.

m.p.: 189-194° C.

¹H NMR (CDCl₃) δ: 8.20 (d, 1H), 7.80 (d, 1H), 8.6 (m, 2H), 7.15-6.95 (m, 4H), 6.90 (d, 1H), 4.00 (s, 3H), 3.55 (m, 4H), 2.55 (m, 4H), 2.40 (s, 3H) ppm.

EXAMPLE 5

(Compound 4): 4-[2-(4-Fluorophenyl)-6-piperazin-1-ylimidazo[1,2-b]pyridazin-3-yl]pyrid-2-ylamine

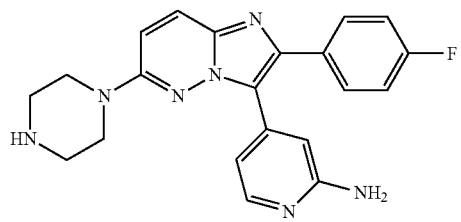 [SMILES: Nc1cc(-c2c(-c3ccc(F)cc3)nc3ccc(N4CCNCC4)nn23)ccn1]

Step 5.1. 2-(4-Fluorophenyl)-6-piperazin-1-ylimidazo[1,2-b]pyridazine

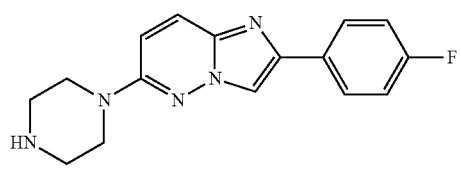 [SMILES: Fc1ccc(-c2cn3nc(N4CCNCC4)ccc3n2)cc1]

Into a reactor containing 94 g (823 mmol) of 98% 1-formylpiperazine at 135° C. are added 26.5 g (107 mmol) of 2-(4-fluorophenyl)-6-chloro-imidazo[1,2-b]pyridazine and the reactor is then closed and maintained at 135° C. for 2 hours 30 minutes.

The reactor is then cooled and the reaction medium is poured into 1.5 L of water. The yellowish solid is isolated by filtration and taken up in 700 mL of tetrahydrofuran. 800 mL of 4N sulfuric acid are then added and the solution is refluxed overnight.

The mixture is filtered while hot and the filtrate is partially concentrated under reduced pressure. This aqueous phase is washed twice with diethyl ether and then basified using cold aqueous ammonia solution. The precipitate formed is stirred for 30 minutes and isolated by filtration through a sinter funnel and washing with water. The solid is taken up in chloroform and the organic phase obtained is washed with water, dried over sodium sulfate and then concentrated under reduced pressure to give a brown-yellow solid. 21.5 g of a pale of yellow powder are isolated by clarification in a mixture of 200 mL of diisopropyl ether and 10 mL of isopropanol at reflux, followed by cold filtration and drying.

m.p.: 200-203° C.

Yield: 61%.

¹H NMR (CDCl₃) δ: 8.05 (s, 1H), 7.85 (m, 2H), 7.65 (d, 1H), 7.05 (m, 2H), 6.94 (d, 1H), 3.40 (s, 4H), 2.85 (s, 4H) ppm.

Step 5.2. tert-Butyl 4-[2-(4-fluorophenyl)imidazo[1,2-b]pyridazin-6-yl]piperazine-1-carboxylate

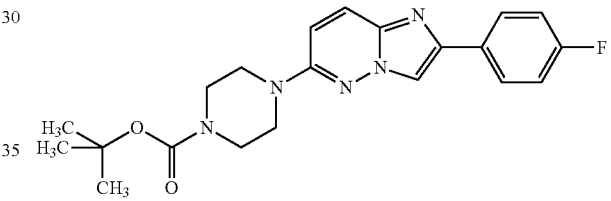

To a solution of 21.5 g (72.3 mmol) of 2-(4-fluorophenyl)-6-piperazin-1-ylimidazo[1,2-b]pyridazine and 0.44 g (3.6 mmol) of dimethylaminopyridine in 500 mL of chloroform is added dropwise a solution of tert-butyl anhydride dissolved in 100 mL of chloroform. After stirring for 30 minutes at room temperature, the medium is poured into saturated aqueous sodium hydrogen carbonate solution. The organic phase obtained is washed with water, dried over sodium sulfate and then concentrated under reduced pressure to give a brown solid. Finally, 28.0 g of a beige-colored powder are isolated after trituration in a mixture of 200 mL of diisopropyl ether and 10 mL of isopropanol at reflux, followed by cold filtration and drying.

Yield: 97%.

¹H NMR (CDCl₃) δ: 7.78-8.00 (m, 3H), 7.80 (d, 1H), 7.15 (pseudo t, 1H). 6.85 (d, 1H), 3.45-3.7 (m, 8H), 1.5 (s, 9H) ppm.

Step 5.3. tert-Butyl 4-[2-(4-fluorophenyl)-3-iodoimidazo[1,2-b]pyridazin-6-yl]piperazine-1-carboxylate

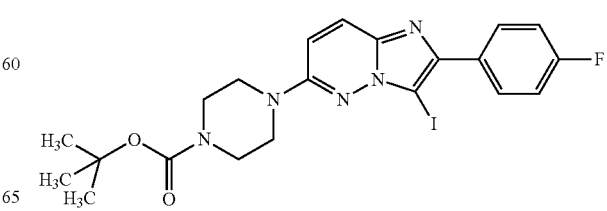

To a solution of 28.0 g (70.5 mmol) of tert-butyl 4-[2-(4-fluorophenyl)imidazo[1,2-b]pyridazin-6-yl]piperazine-1-carboxylate in 800 mL of tetrahydrofuran cooled to about 0° C. are added 17.4 g (77.5 mmol) of N-iodosuccinimide. After stirring for 18 hours at room temperature, the solvent is evaporated off under reduced pressure.

The orange-red solid obtained is triturated in 1.5 L of water and separated out by filtration. The solid is then taken up in chloroform and the organic phase obtained is washed with 1 L of 5% sodium thiosulfate solution, dried over sodium sulfate and then concentrated under reduced pressure to give a brown solid.

32.8 g of a pale of yellow powder are finally isolated by clarification in a mixture of 300 mL of diisopropyl ether and 50 mL of isopropanol at reflux, followed by cold filtration and drying.

Yield: 89%

$^1$H NMR (CDCl$_3$) δ: 7.85 (pseudo q, 2H), 7.60 (d, 1H), 7.05 (pseudo t, 1H). 6.75 (d, 1H), 3.5 (m, 8H), 1.4 (s, 9H) ppm.

Step 5.4. tert-Butyl 4-[3-(2-chloropyrid-4-yl)-2-(4-fluorophenyl)imidazo[1,2-b]pyridazin-6-yl]piperazine-1-carboxylate (according to Scheme 5b)

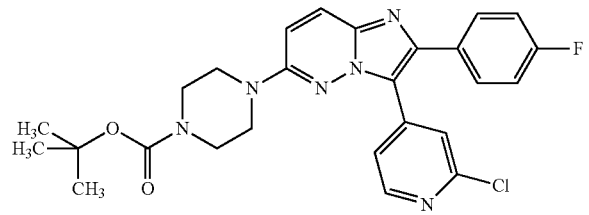 [SMILES: CC(C)(C)OC(=O)N1CCN(c2ccc3nc(-c4ccc(F)cc4)c(-c4ccnc(Cl)c4)n3n2)CC1]

To a suspension of 1.25 g (2.39 mmol) of tert-butyl 4-[2-(4-fluorophenyl)-3-iodoimidazo[1,2-b]pyridazin-6-yl]piperazine-1-carboxylate in a mixture of tetrahydrofuran and water are added 2.33 g (7.17 mmol) of cesium carbonate and 0.45 g (2.9 mmol) of 2-chloropyridine-4-boronic acid. After sparging with a stream of argon for a few moments, 0.18 g (0.21 mmol) of [1,1'-bis(diphenylphosphino)ferrocene] dichloro)palladium(II) (PdCl$_2$(dppf)) is added and the reaction mixture is refluxed under argon for 18 hours. The solvent is then stripped off under reduced pressure, the residue is taken up in chloroform, the organic phase obtained is washed with water, dried over sodium sulfate and filtered, and the filtrate is concentrated under reduced pressure. The brown solid obtained is purified by chromatography on silica gel (50 g), eluting with a mixture of dichloromethane, methanol and aqueous ammonia (95/5/0.5). The product obtained is crystallized from 20 ml of refluxing acetonitrile to give 0.95 g of a white powder after cooling, filtering off and drying.

Yield: 78%

$^1$H NMR (CDCl$_3$) δ: 8.25 (d, 1H), 7.70 (d, 1H), 7.60 (s, 1H), 7.45 (pseudo q, 2H), 7.25 (d, 1H), 6.95 (pseudo t, 2H), 6.80 (d, 1H), 3.25-3.50 (m, 8H), 1.35 (s, 9H) ppm.

Step 5.5. tert-Butyl 4-[3-[2-(benzhydrylideneamino)pyrid-4-yl]-2-(4-fluorophenyl)imidazo[1,2-b]pyridazin-6-yl]piperazine-1-carboxylate Synthesis According to Scheme 3:

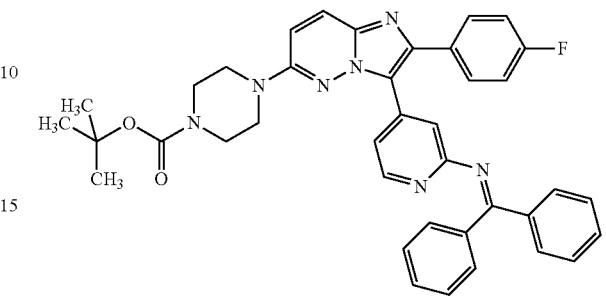

To a suspension of 0.95 g (1.9 mmol) of tert-butyl 4-[3-(2-chloropyrid-4-yl)-2-(4-fluorophenyl)imidazo[1,2-b]pyridazin-6-yl]piperazine-1-carboxylate and 0.41 g (2.2 mmol) of benzhydrylideneamine in 100 mL of anhydrous toluene are added under argon 0.25 g (2.6 mmol) of sodium tert-butoxide and 46 mg (0.075 mmol) of (±)-2,2'-bis(diphenylphosphino)-1,1'-binaphthyl.

After sparging with a stream of argon for a few moments, 34 mg (0.037 mmol) of tris(dibenzylideneacetone)dipalladium(0) are added and the reaction mixture is refluxed under argon for 18 hours. The medium is filtered while hot and the solvent is then stripped off under reduced pressure. The residue is taken up in chloroform, the organic phase obtained is washed with water, dried over sodium sulfate and filtered, and the filtrate is concentrated under reduced pressure. The brown solid obtained is purified by chromatography on silica gel (50 g), eluting with a mixture of dichloromethane, methanol and aqueous ammonia (95/2/0.2). The product obtained is crystallized from a mixture of 20 mL of acetonitrile and 5 mL of n-butanol at reflux to give 0.80 g of a white powder after cooling, filtering off and drying.

Yield: 65%

$^1$H NMR (CDCl$_3$) δ: 8.25 (d, 1H), 7.70 (m, 3H), 7.05-7.45 (m), 6.85-6.95 (m, 4H), 6.80 (d, 1H), 3.55-3.30 (m, 8H), 1.40 (s, 9H) ppm.

Step 5.6. 4-[2-(4-Fluorophenyl)-6-piperazin-1-ylimidazo[1,2-b]pyridazin-3-yl]pyrid-2-ylamine

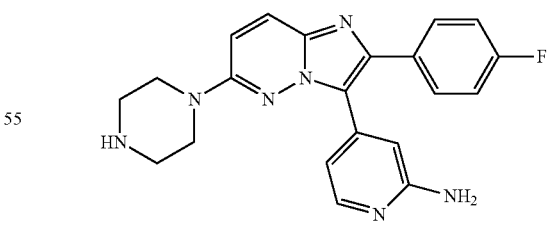

A suspension of 0.80 (1.22 mmol) of tert-butyl 4-[3-[2-(benzhydrylideneamino)pyrid-4-yl]-2-(4-fluorophenyl)imidazo[1,2-b]pyridazin-6-yl]piperazine-1-carboxylate in 70 mL of aqueous hydrochloric acid is maintained at 80° C. for about 1 hour 30 minutes. After cooling, the aqueous phase is washed twice with diethyl ether and then basified by addition of ice-cold aqueous ammonia. The product is extracted with chloroform and the organic phase obtained is washed with water, dried over sodium sulfate and filtered, and the filtrate is concentrated under reduced pressure. The brown solid obtained is purified by chromatography on silica gel (35 g), eluting with a mixture of dichloromethane, methanol and aqueous ammonia (90/10/1). The product obtained is crystallized from 20 mL of refluxing acetonitrile to give 0.38 g of a white powder after cooling, filtering off and drying m.p.: 255° C. (decomposition)
$^1$H NMR (CDCl$_3$) δ: 8.05 (d, 1H), 7.80 (d, 1H), 7.60-7.70 (m, 2H), 6.85-7.15 (m, 4H), 6.80 (s, 1H), 4.45 (broad unresolved complex, 2H), 3.40-3.60 (m, 4H), 2.95-3.10 (m, 4H) ppm.

EXAMPLE 6

(Compound 113): 4-[2-(4-Fluorophenyl)-6-[5-benzyl (hexahydropyrrolo[3,4-c]pyrrol-2(1H)-yl)]-7,8-dimethylimidazo[1,2-b]pyridazin-3-yl]pyrid-2-ylamine

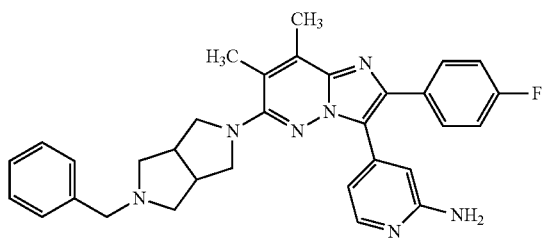 [SMILES: Cc1c(N2CC3CN(Cc4ccccc4)CC3C2)nn2c(-c3ccnc(N)c3)c(-c3ccc(F)cc3)nc2c1C]

Synthesis According to Scheme 1, Route 4:

Step 6.1. tert-Butyl[4-(4,4,5,5-tetramethyl-1,3,2-dioxaborolan-2-yl)pyrid-2-yl]carbamate

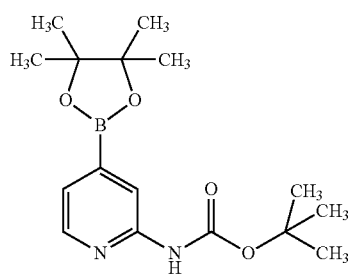 [SMILES: CC(C)(C)OC(=O)Nc1cc(B2OC(C)(C)C(C)(C)O2)ccn1]

To a solution of 6.76 (24.8 mmol) of tert-butyl (4-bromopyrid-2-yl)carbamate (Deady, Leslie W.; Korytsky, Olga L.; Rowe, Jeffrey E.; Aust. J. Chem.; 35; 10; 1982; 2025-2034) in 150 mL of dimethylformamide are added 8.0 g (81 mmol) of potassium acetate predried at 130° C. and 6.9 g (27 mmol) of bis(pinacolato)diboron. A stream of argon is then sparged through for a few moments, and 1.2 g (1.5 mmol) of [1,1'-bis(diphenylphosphino)ferrocene]dichloropalladium (II) are added. The mixture is stirred at 80° C. under argon for 2 hours and then poured into saturated aqueous ammonium chloride solution. The product is extracted with ethyl acetate, the organic phase is dried over sodium sulfate and the solvent is stripped off under reduced pressure. The residue is triturated in 300 mL of refluxing diisopropyl ether and the insoluble matter is separated out by filtration.

The filtrate is cooled and partially concentrated under reduced pressure. After adding 70 mL of hexane, the precipitate formed is isolated by filtration to give 4.2 g of an orange-colored solid after drying.

Yield: 53%
m.p.: 188-193° C.
$^1$H NMR (CDCl$_3$) δ: 8.15 (m, 2H), 7.65 (broad s, 1H), 7.15 (d, 1H), 1.40 (s, 9H), 1.20 (s, 12H) ppm.

Step 6.2. 6-(5-Benzylhexahydropyrrolo[3,4-c]pyrrol-2-yl)-2-(4-fluorophenyl)-7,8-dimethylimidazo[1,2-b]pyridazine

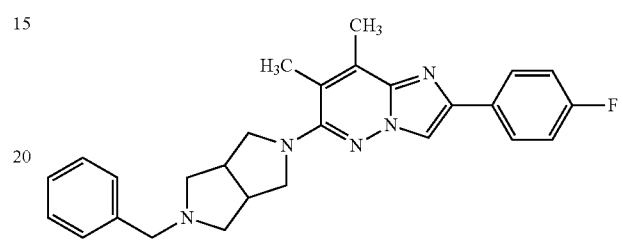

A mixture of 3.00 g (10.9 mmol) of 6-chloro-2-(4-fluorophenyl)-7,8-dimethylimidazo[1,2-b]pyridazine and 6.6 g (33 mmol) of 2-benzyloctahydropyrrolo[3,4-c]pyrrole in 20 mL of pentanol is heated at 150° C. for 2 days in a reactor. The medium is then poured into aqueous 1N hydrochloric acid solution. The aqueous phase is washed with ethyl acetate and then basified with sodium hydroxide.

The product is extracted with dichloromethane and the organic phase is dried over sodium sulfate and then concentrated under reduced pressure. The yellow oil obtained is chromatographed on silica gel, eluting with dichloromethane containing 3% methanol and 0.3% aqueous ammonia. The product is then crystallized from diisopropyl ether to give 3.2 g of a slightly yellow powder.

m.p.: 115-117° C.
$^1$H NMR (CDCl$_3$) δ: 7.85 (m; 3H), 7.30 (m, 5H), 7.05 (pseudo t, 2H), 3.60 (s, 2H), 3.30 (m, 2H), 3.10 (m, 2H), 2.80 (m, 4H), 2.55 (s, 3H), 2.35 (m, 2H), 2.25 (s, 3H) ppm.

Step 6.3. 6-(5-Benzylhexahydropyrrolo[3,4-c]pyrrol-2-yl)-2-(4-fluorophenyl)-3-iodo-7,8-dimethylimidazo[1,2-b]pyridazine

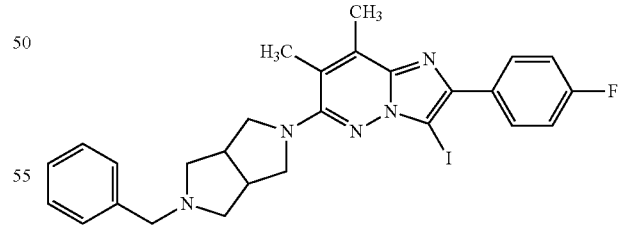

To a solution, cooled to 0° C., of 3.2 g (7.3 mmol) of 6-(5-benzylhexahydropyrrolo[3,4-c]pyrrol-2-yl)-2-(4-fluorophenyl)-7,8-dimethylimidazo[1,2-b]pyridazine in 20 mL of chloroform is added dropwise a solution of 1.8 g (11 mmol) of iodine monochloride in 3 mL of methanol and the medium is stirred for one hour at room temperature. The medium is then basified by addition of aqueous sodium hydrogen carbonate solution and 5% sodium thiosulfate solution is then added until the medium has decolorized.

The product is extracted with chloroform, the organic phase is dried over sodium sulfate and filtered, and the solvent is evaporated off to give 3.2 g of a yellow powder after crystallization from diethyl ether and drying.

¹H NMR (DMSO-d₆) δ: 8.35 (m; 2H), 7.65 (m, 7H), 3.80 (s, 2H), 3.65 (m, 2H), 3.40 (m, 2H), 3.07 (m, 2H), 2.90 (m, 2H), 2.65 (m, 2H), 2.5 (s, 3H) ppm.

Step 6.4. tert-Butyl {4-[6-(5-benzylhexahydropyrrolo[3,4-c]pyrrol-2-yl)-2-(4-fluorophenyl)-7,8-dimethylimidazo[1,2-b]pyridazin-3-yl}pyrid-2-yl]carbamate

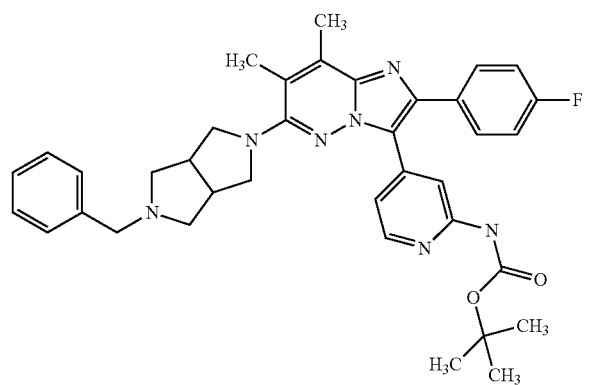 [SMILES: Cc1c(N2CC3CN(Cc4ccccc4)CC3C2)nn2c(-c3ccnc(NC(=O)OC(C)(C)C)c3)c(-c3ccc(F)cc3)nc2c1C]

To a solution of 3.60 g (6.34 mmol) of 6-(5-benzylhexahydropyrrolo[3,4-c]pyrrol-2-yl)-2-(4-fluorophenyl)-3-iodo-7,8-dimethylimidazo[1,2-b]pyridazine in 15 mL of a mixture of tetrahydrofuran and water (9:1) are added 6.2 g (19 mmol) of cesium carbonate and 2.4 g (7.6 mmol) of tert-butyl[4-(4,4,5,5-tetramethyl-1,3,2-dioxaborolan-2-yl)pyrid-2-yl]carbamate. After sparging with a stream of argon for a few moments, 0.47 mg (0.57 mmol) of a complex of [1,1'-bis(diphenylphosphino)ferrocene]dichloropalladium(II) and dichloromethane (PdCl₂(dppf).CH₂Cl₂) is added and the reaction mixture is refluxed under argon for 5 hours. The mixture is then poured into 250 mL of water and the product is extracted with ethyl acetate, the organic phase is dried over sodium sulfate and filtered, and the solvent is evaporated off to give a brown solid. The product is purified by chromatography on silica gel, eluting with a mixture of dichloromethane, methanol and aqueous ammonia (95:5:05) to give 2.91 g of a beige-colored solid.

m.p.: 214-216° C.

¹H NMR (CDCl₃) δ: 8.70 (s, 1H), 8.20 (d; 1H), 7.92 (s, 1H), 7.7 (m, 2H), 7.3-7.4 (m, 4H), 7.1 (m, 3H), 3.70 (s, 2H), 3.35 (m, 4H), 3.0 (m, 4H), 2.70 (m, 4H), 2.70 (s, 3H), 2.35 (s+m, 3+2H), 1.55 (s, 9H) ppm.

Step 6.5. 4-[6-(5-Benzylhexahydropyrrolo[3,4-c]pyrrol-2-yl)-2-(4-fluorophenyl)-7,8-dimethylimidazo[1,2-b]pyridazin-3-yl]pyrid-2-ylamine

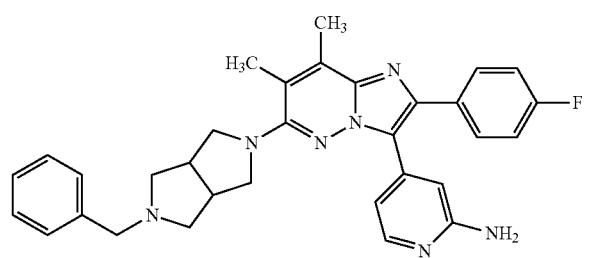 [SMILES: Cc1c(N2CC3CN(Cc4ccccc4)CC3C2)nn2c(-c3ccnc(N)c3)c(-c3ccc(F)cc3)nc2c1C]

To a solution of 2.9 g (4.58 mmol) of tert-butyl {4-[6-(5-benzylhexahydropyrrolo[3,4-c]pyrrol-2-yl)-2-(4-fluorophenyl)-7,8-dimethylimidazo[1,2-b]pyridazin-3-yl]pyrid-2-yl}carbamate in 30 mL of dichloromethane are added 6.8 mL of trifluoroacetic acid and the reaction is stirred for 2 hours. The medium is poured into 200 mL of water and the mixture is basified by addition of aqueous ammonia.

The organic phase is separated out, dried over sodium sulfate and concentrated to dryness under reduced pressure. 2.3 g of a white gummy solid are thus isolated.

m.p.: 113° C.

¹H NMR (CDCl₃) δ: 8.10 (d, 1H), 7.70 (m; 2H), 7.3 (m, 4H), 7.1 (pseudo t, 2H), 7.00 (d, 1H), 6.90 (s, 1H), 4.40 (broad s, 2H), 3.65 (s, 2H), 3.3 (m, 4H), 2.9 (m, 4H), 2.65 (s, 3H), 2.35 (s+m, 3+2H), 1.55 (s, 9H) ppm.

EXAMPLE 7

(Compound 114): 4-[2-(4-Fluorophenyl)-6-(hexahydropyrrolo[3,4-c]pyrrol-2-yl)-7,8-dimethylimidazo[1,2-b]pyridazin-3-yl]pyrid-2-ylamine

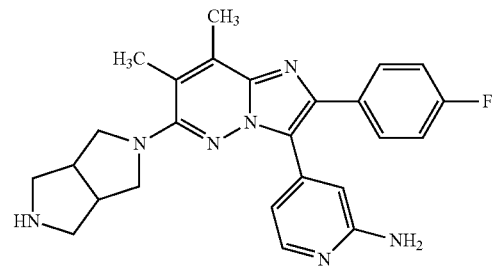 [SMILES: Cc1c(N2CC3CNCC3C2)nn2c(-c3ccnc(N)c3)c(-c3ccc(F)cc3)nc2c1C]

To a solution of 2.30 g (4.3 mmol) of 4-[6-(5-benzylhexahydropyrrolo[3,4-c]pyrrol-2-yl)-2-(4-fluorophenyl)-7,8-dimethylimidazo[1,2-b]pyridazin-3-yl]pyrid-2-ylamine in 150 mL of methanol are added 4 g (64 mmol) of ammonium formate and 1 g of 10% palladium-on-charcoal containing 50% water. The mixture is stirred at reflux for 2 hours and the solvent is then removed under reduced pressure. The residue is taken up in water and the resulting aqueous phase is basified using aqueous 1N sodium hydroxide. The product is extracted with chloroform, the organic phase is washed with water, dried over sodium sulfate and filtered, and the solvent is evaporated off to give an orange-colored oil. After purification by chromatography on a column of silica gel, eluting with a mixture of dichloromethane, methanol and aqueous ammonia (87:13:1.3), 1.23 g of a white powder are obtained after crystallization from ether and drying under reduced pressure.

m.p.: 254-256° C.

¹H NMR (DMSO-d₆) δ: 7.95 (d, 1H), 7.60 (pseudo dd; 2H), 7.20 (pseudo t, 2H), 6.65 (s, 1H), 6.65 (d, 1H), 5.95 (broad s, 1H), 3.3 (m, 6H), 2.8-3.1 (m, 4H), 2.8-2.25 (m), 2.25 (s, 3H), ppm.

EXAMPLE 8

(Compound 111): 4-[2-(4-Chlorophenyl)-6-(hexahydropyrrolo[3,4-c]pyrrol-2(1H)-yl)imidazo[1,2-b]pyridazin-3-yl]pyrid-2-ylamine

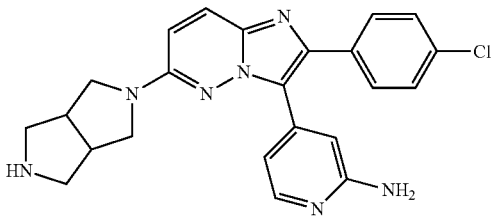 [SMILES: Nc1cc(-c2c(-c3ccc(Cl)cc3)nc3ccc(N4CC5CNCC5C4)nn23)ccn1]

Synthetic Process According to Scheme 1, Route 1:

Step 8.1. 6-Chloro-2-(4-chlorophenyl)-3-iodoimidazo[1,2-b]pyridazine (according to Scheme 6)

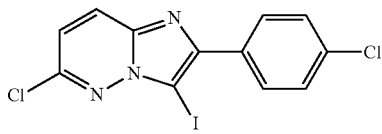 [SMILES: Clc1ccc(-c2nc3ccc(Cl)nn3c2I)cc1]

To a solution, cooled to 0° C., of 3.00 g (11.1 mmol) of 6-chloro-2-(4-chlorophenyl)-3-iodoimidazo[1,2-b]pyridazine (CAS No.: 1844-56-0) in 55 mL of chloroform is rapidly added dropwise a solution of 2.70 g (16.7 mmol) of iodine monochloride in 15 mL of chloroform. After cooling to room temperature and stirring for 3 hours, a further 0.75 g (4.6 mmol) of iodine monochloride is added and the reaction mixture is stirred for a further one hour. The mixture is then treated with aqueous 5% sodium thiosulfate solution. The product is extracted with dichloromethane. The organic phase is dried by filtration through a hydrophobic filter cartridge and concentrated under reduced pressure. The residue is triturated in acetonitrile, and the solid is isolated by filtration. 3.8 g of a beige-colored powder are isolated after drying under vacuum.

m.p.: 201-203° C.

$^1$H NMR (CDCl$_3$) δ: 8.20 (d; 1H), 8.10 (d, 2H), 8.6 (d, 2H), 7.45 (d, 1H) ppm.

Step 8.2. tert-Butyl{-4-[6-chloro-2-(4-chlorophenyl)imidazo[1,2-b]pyridazin-3-yl]pyrid-2-yl}carbamate

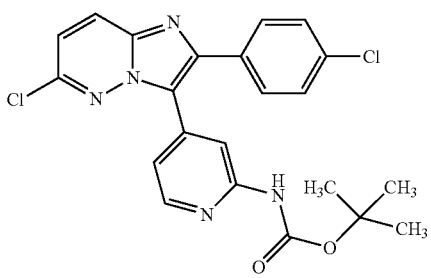 [SMILES: CC(C)(C)OC(=O)Nc1cc(-c2c(-c3ccc(Cl)cc3)nc3ccc(Cl)nn23)ccn1]

To a suspension of 3 g (7.31 mmol) of 6-chloro-2-(4-chlorophenyl)-3-iodoimidazo[1,2-b]pyridazine in 183 mL of a mixture of tetrahydrofuran and water (9:1) are added 7.1 g (22 mmol) of cesium carbonate and 2.90 g (8.8 mmol) of tert-butyl[4-(4,4,5,5-tetramethyl-1,3,2-dioxaborolan-2-yl)pyrid-2-yl]carbamate. After sparging with a stream of argon for a few moments, 0.54 g (0.66 mmol) of [1,1'-bis(diphenylphosphino)ferrocene]dichloropalladium(II) is added and the reaction mixture is refluxed under argon for 18 hours. After filtering through a Whatman filter and through Celite, the filtrate is then concentrated under reduced pressure to give 7.0 g of a brown residue. The residue is taken up in water, the product is extracted with dichloromethane, the organic phase is dried over sodium sulfate and filtered, and the solvent is evaporated off to give 3.5 g of a dark powder.

The product is purified by chromatography on silica gel, eluting with a mixture of dichloromethane and ethyl acetate (100:0 to 80:20) to give 1.8 g of beige-colored crystals after crystallization from diisopropyl ether and drying under reduced pressure.

m.p.: 212-214° C.

$^1$H NMR (DMSO-d$_6$) δ: 9.9 (s; 1H), 8.4 (d, 1H), 8.3 (d, 1H), 7.95 (s, 1H), 7.60 (d, 2H), 7.45 (m, 3H), 7.15 (d, 1H), 4.40 (s, 9H) ppm.

Step 8.3. 4-[6-Chloro-2-(4-chlorophenyl)imidazo[1,2-b]pyridazin-3-yl]pyrid-2-ylamine

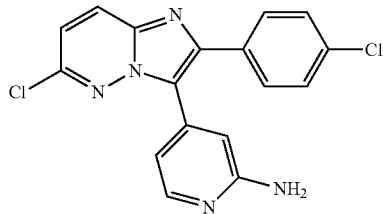 [SMILES: Nc1cc(-c2c(-c3ccc(Cl)cc3)nc3ccc(Cl)nn23)ccn1]

To a suspension of 0.76 g (1.67 mmol) of tert-butyl {4-[6-chloro-2-(4-chlorophenyl)imidazo[1,2-b]pyridazin-3-yl]pyrid-2-yl}carbamate in 8 mL of dichloromethane are added 4 mL (48 mmol) of hydrochloric acid. After stirring for 2 hours at room temperature, the solvent is evaporated off under reduced pressure, the oily residue is taken up with aqueous ammonia and the product is extracted with dichloromethane. The organic phase is filtered on a hydrophobic cartridge and concentrated under reduced pressure. The solid obtained is triturated with diisopropyl ether to give 0.56 g of solid after filtering off and drying under reduced pressure.

m.p.: 269-271° C.

$^1$H NMR (DMSO-d$_6$) δ: 8.25 (d; 1H), 8.05 (d, 1H), 7.65 (d, 1H), 7.45 (m, 3H), 6.65 (m, 2H), 6.1 (broad s, 2H) ppm.

Step 8.4. tert-Butyl 5-[3-(2-aminopyrid-4-yl)-2-(4-chlorophenyl)imidazo[1,2-b]pyridazin-6-yl]hexahydropyrrolo[3,4-c]pyrrole-2-carboxylate

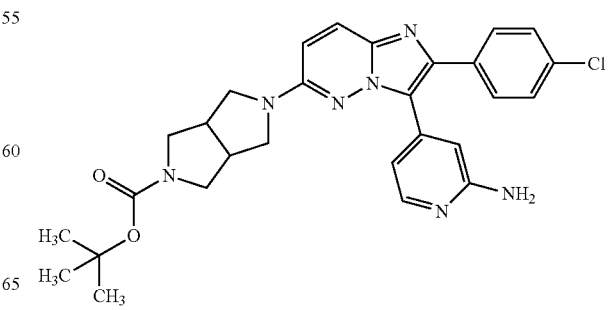

A mixture of 0.15 g (0.42 mmol) of 4-[6-chloro-2-(4-chlorophenyl)imidazo[1,2-b]pyridazin-3-yl]pyrid-2-ylamine and 0.36 g (1.7 mmol) of tert-butyl hexahydropyrrolo[3,4-c]pyrrole-2-carboxylate in 7 mL of pentanol is stirred at 135° C. for 20 hours. The solvent is then evaporated off under reduced pressure and the oily residue is chromatographed on a column of silica gel, eluting with a stepwise gradient of methanol and aqueous ammonia in dichloromethane (0:0:100 to 2:1:98). 0.16 g of product is isolated after trituration in diisopropyl ether, filtering off and drying under reduced pressure.

$^1$H NMR (DMSO-d$_6$) δ: 7.95 (d; 1H), 7.85 (d, 1H), 7.55 (d, 2H), 7.40 (d, 2H), 6.90 (d, 1H), 6.70 (s, 1H), 6.55 (d, 1H), 5.95 (broad s, 2H), 2.9-3.7 (m), 1.35 (s, 9H) ppm.

Step 8.5. 4-[2-(4-Chlorophenyl)-6-(hexahydropyrrolo[3,4-c]pyrrol-2-yl)imidazo[1,2-b]pyridazin-3-yl]pyrid-2-ylamine

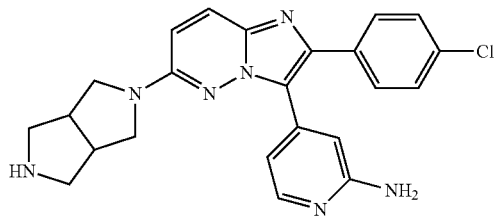 [SMILES: Nc1cc(-c2c(-c3ccc(Cl)cc3)nc3ccc(N4CC5CNCC5C4)nn23)ccn1]

To a solution of 0.16 g (0.29 mmol) of tert-butyl 5-[3-(2-aminopyrid-4-yl)-2-(4-chlorophenyl)imidazo[1,2-b]pyridazin-6-yl]hexahydropyrrolo[3,4-c]pyrrole-2-carboxylate in 3 mL of dichloromethane are added 1.5 mL (18 mmol) of concentrated hydrochloric acid. After stirring for 1 hour at room temperature, the solvent is evaporated off under reduced pressure, the oily residue is taken up with aqueous ammonia and the product is extracted with dichloromethane. The organic phase is filtered on a hydrophobic cartridge and concentrated under reduced pressure. The solid obtained is triturated with diisopropyl ether to give 0.091 g of solid after filtering off and drying under reduced pressure.

m.p.: 267-270° C.

$^1$H NMR (DMSO-d$_6$) δ: 7.95 (d; 1H), 7.85 (d, 1H), 7.60 (d, 2H), 7.40 (d, 2H), 6.95 (d, 1H), 6.70 (s, 1H), 6.60 (d, 1H), 5.95 (broad s, 2H), 3.6 (m, 2H), 3.4-3.1 (m), 2.7-3.95 (m, 4H), 2.6 (d, 2H) ppm.

EXAMPLE 9

(Compound 65): 2-{4-[2-(4-Fluorophenyl)-3-(2-methoxypyrid-4-yl)imidazo[1,2-b]pyridazin-6-yl]piperazin-1-yl}ethanol

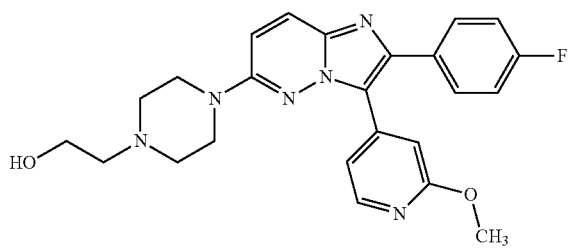 [SMILES: COc1cc(-c2c(-c3ccc(F)cc3)nc3ccc(N4CCN(CCO)CC4)nn23)ccn1]

Synthesis According to Scheme 1, Route 1:

Step 9.1. 6-Chloro-2-(4-fluorophenyl)-3-iodoimidazo[1,2-b]pyridazine

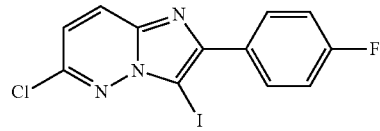 [SMILES: Fc1ccc(-c2nc3ccc(Cl)nn3c2I)cc1]

To a solution, cooled to 0° C., of 5.20 g (21.0 mmol) of 6-chloro-2-(4-fluorophenyl)imidazo[1,2-b]pyridazine (CAS No.: 244081-70-7) in 130 mL of chloroform is rapidly added dropwise a solution of 6.61 g (40.9 mmol) of iodine monochloride in 40 mL of chloroform. After cooling to room temperature and stirring for 4 hours, the mixture is treated with aqueous 5% sodium thiosulfate solution. The product is extracted with dichloromethane. The organic phase is dried by filtration through a hydrophobic filter cartridge and concentrated under reduced pressure. The residue is triturated in acetonitrile, and the solid is isolated after filtering off and rinsing with diisopropyl ether. 5.7 g of a beige-colored powder are isolated after drying under vacuum.

m.p.: 215° C.

$^1$H NMR (DMSO-d$_6$) δ: 8.20 (m; 3H), 7.40 (m, 3H) ppm.

Step 9.2. 6-Chloro-2-(4-fluorophenyl)-3-(2-methoxypyrid-4-yl)imidazo[1,2-b]pyridazine (According to Scheme 6)

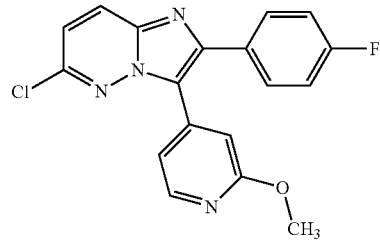 [SMILES: COc1cc(-c2c(-c3ccc(F)cc3)nc3ccc(Cl)nn23)ccn1]

To a suspension of 5.7 g (14.8 mmol) of 6-chloro-2-(4-fluorophenyl)-3-iodoimidazo[1,2-b]pyridazine in 370 mL of a mixture of tetrahydrofuran and water (9:1) are added 14.7 g (44.4 mmol) of cesium carbonate and 2.77 g (17.8 mmol) of (2-methoxypyrid-4-yl)boronic acid. After sparging with a stream of argon for a few moments, 0.98 g (1.2 mmol) of a complex of [1,1'-bis(diphenylphosphino)ferrocene]dichloropalladium(II) and dichloromethane (PdCl$_2$(dppf).CH$_2$Cl$_2$) is added and the reaction mixture is refluxed under argon for 4 hours. The medium is then concentrated under reduced pressure to give a black residue. The residue is taken up in 200 mL of water, the product is extracted with 500 mL of dichloromethane, the organic phase is dried by passing through a hydrophobic filter, filtered and the solvent is evaporated off to give 7 g of residue. The product is purified by chromatography on silica gel, eluting with a mixture of dichloromethane and ethyl acetate (100:0 to 70:30) to give 3.5 g of beige-colored crystals after crystallization from diisopropyl ether and drying under reduced pressure.

m.p.: 184° C.

$^1$H NMR (DMSO-d$_6$) δ: 8.30 (m, 2H), 7.60 (m, 2H), 7.45 (d, 1H), 7.20 (pseudo t, 2H), 7.05 (m, 2H), 2.90 (s, 3H) ppm.

Step 9.3. 2-{4-[2-(4-Fluorophenyl)-3-(2-methoxypyrid-4-yl)imidazo[1,2-b]pyridazin-6-yl]piperazin-1-yl}ethanol

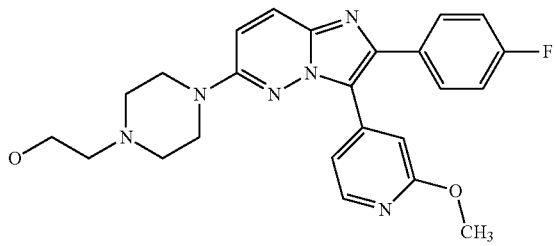 [SMILES: COc1cc(-c2c(-c3ccc(F)cc3)nc3ccc(N4CCN(CCO)CC4)nn23)ccn1]

A mixture of 0.25 g (0.70 mmol) of 6-chloro-2-(4-fluorophenyl)-3-(2-methoxypyrid-4-yl)imidazo-[1,2-b]pyridazine and 0.37 g (2.8 mmol) of 2-(piperazin-1-yl)ethanol in 6 mL of pentanol is stirred at 135° C. for 18 hours. The solvent is then evaporated off under reduced pressure and the oily residue is chromatographed on a column of silica gel, eluting with a stepwise gradient of methanol and aqueous ammonia in dichloromethane (0/0/100 to 2/1/98). 0.136 g of product is isolated after trituration in diisopropyl ether, filtering off and drying under reduced pressure.

m.p.: 176-179° C.

$^1$H NMR (CDCl$_3$) δ: 8.20 (d; 1H), 7.80 (d, 1H), 7.60 (d, 2H), 7.00-7.15 (m, 4H), 4.00 (s, 3H), 3.70 (m, 2H), 3.55 (m, 4H), 2.7 (m, 6H) ppm.

EXAMPLE 10

(Compound 130): 9-[3-(2-Methylpyrid-4-yl)-2-phenylimidazo[1,2-b]pyridazin-6-yl]-2,9-diazaspiro[5.5]undecane

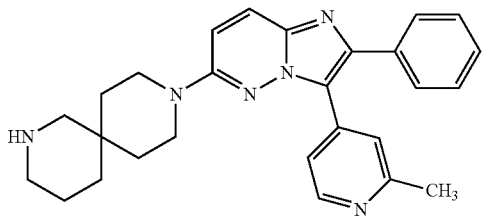 [SMILES: Cc1cc(-c2c(-c3ccccc3)nc3ccc(N4CCC5(CCCNC5)CC4)nn23)ccn1]

Synthetic Process According to Scheme 1, Route 1:

Step 10.1.
6-Chloro-2-phenyl-3-iodoimidazo[1,2-b]pyridazine

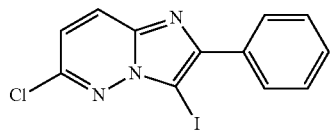 [SMILES: Clc1ccc2nc(-c3ccccc3)c(I)n2n1]

To a solution, cooled to 0° C., of 10.4 g (45.4 mmol) of 6-chloro-2-phenylimidazo[1,2-b]pyridazine (CAS No.: 1844-53-7) in 500 mL of chloroform is rapidly added dropwise a solution of 11.1 g (68.1 mmol) of iodine monochloride in 100 mL of chloroform. After cooling to room temperature and stirring for 1 hour, the mixture is treated with aqueous 5% sodium thiosulfate solution. The product is extracted with dichloromethane and the organic phase is dried over sodium sulfate and concentrated under reduced pressure. The residue is triturated in 150 ml of acetonitrile containing a few mL of isopropyl alcohol and the solid is isolated after filtration. 15 g of a yellow powder are isolated after drying under vacuum.

m.p.: 207-212° C.

$^1$H NMR (DMSO-d$_5$) δ: 8.15 (dd; 2H), 7.90 (d, 1H)), 7.5 (d, 3H)), 7.15 (d, 1H) ppm.

Step 10.2. 6-Chloro-2-phenyl-3-(2-methylpyrid-4-yl)imidazo[1,2-b]pyridazine (According to Scheme 6)

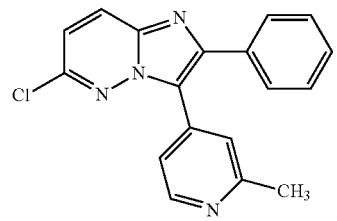 [SMILES: Cc1cc(-c2c(-c3ccccc3)nc3ccc(Cl)nn23)ccn1]

To a suspension of 4.33 g (14.8 mmol) of 6-chloro-2-phenyl-3-iodoimidazo[1,2-b]pyridazine in 200 mL of a mixture of tetrahydrofuran and water (9:1) are added 11.9 g (36.5 mmol) of cesium carbonate and 2 g (14.6 mmol) of (2-methylpyrid-4-yl)boronic acid. After sparging with a stream of argon for a few moments, 0.89 g (1.1 mmol) of a complex of [1,1'-bis(diphenylphosphino)ferrocene]dichloropalladium (II) and dichloromethane (PdCl$_2$(dppf).CH$_2$Cl$_2$) is added and the reaction mixture is refluxed under argon for 18 hours. The medium is then concentrated under reduced pressure to give a black residue.

The residue is taken up in 1N hydrochloric acid and the solution is filtered through a Büchner funnel. The aqueous phase is washed with diethyl ether and is then basified with aqueous ammonia.

The product is then extracted with dichloromethane and the organic phase is dried over sodium sulfate and concentrated under reduced pressure to give 3.3 g of a yellowish residue. The product is purified by chromatography on silica gel, eluting with a mixture of dichloromethane, methanol and aqueous ammonia (98/2/0.2)) to give 2.65 g of a pale yellow solid after drying under reduced pressure.

m.p.: 183-188° C.

$^1$H NMR (DMSO-d$_6$) δ: 8.60 (d, 1H), 8.05 (d, 1H), 7.7 (m, 1H), 7.5 (m, 5H), 7.20 (d, 1H), 2.60 (s, 3H) ppm.

Step 10.3. 9-[3-(2-Methylpyrid-4-yl)-2-phenylimidazo[1,2-b]pyridazin-6-yl]-2,9-diazaspiro[5.5]undecane

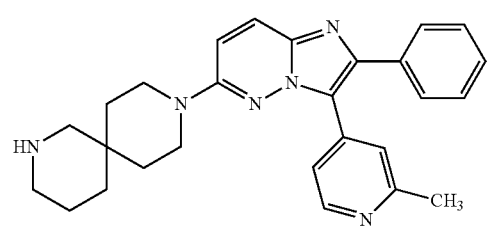 [SMILES: Cc1cc(-c2c(-c3ccccc3)nc3ccc(N4CCC5(CCCNC5)CC4)nn23)ccn1]

A mixture of 0.80 g (2.5 mmol) of 6-chloro-2-phenyl-3-(2-methylpyrid-4-yl)imidazo[1,2-b]pyridazine and 2.2 g (7.5 mmol) of tert-butyl 2,9-diazaspiro[5.5]undecane-2-carboxylate in 8 mL of pentanol is stirred at 150° C. for 40 hours.

The mixture is then poured into 30 mL of aqueous 3N hydrochloric acid and stirred for 2 hours. The aqueous phase is washed with diethyl ether and then basified with aqueous ammonia.

The product is then extracted with dichloromethane and the organic phase is dried over sodium sulfate and concentrated under reduced pressure to give 0.76 g of solid. The product is crystallized from 30 ml of acetonitrile to give 0.577 g of product after drying under reduced pressure.

m.p.: 175-179° C.

$^1$H NMR (CDCl$_3$) δ: 8.50 (d; 1H), 7.75 (d, 1H), 7.65 (m, 2H), 7.50 (s, 1H), 7.30-7.45 (m, 4H), 6.90 (d, 1H), 3.50 (t, 4H), 2.85 (m, 2H), 2.75 (s, 2H), 2.55 (s, 3H), 1.6-1.75 (m, 6H) ppm.

EXAMPLE 11

(Compound 147): 2-Phenyl-3-pyrid-4-yl-6-(4-pyrrolidin-1-ylpiperid-1-yl)imidazo[1,2-b]pyridazine

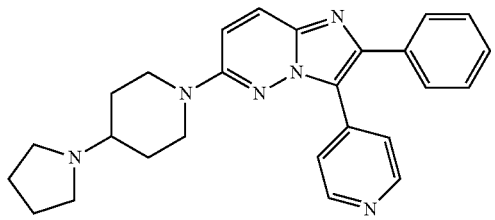 [SMILES: c1ccc(-c2nc3ccc(N4CCC(N5CCCC5)CC4)nn3c2-c2ccncc2)cc1]

Synthetic Process According to Scheme 1, Route 2:

Step 11.1. 2-Bromo-1-phenyl-2-pyrid-4-ylethanone

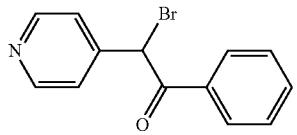 [SMILES: O=C(c1ccccc1)C(Br)c1ccncc1]

To a solution of 36 g (182 mmol) of 1-phenyl-2-pyrid-4-ylethanone in 350 mL of acetic acid are successively added at room temperature 28 ml (210 mmol) of a solution containing 30% by weight of hydrobromic acid in acetic acid and 10.1 ml (197 mmol) of bromine dissolved in 50 mL of acetic acid. The solution is heated at 60° C. for one hour and then cooled. The product is precipitated by adding diethyl ether, and 63 g of a yellow solid are isolated after drying.

$^1$H NMR (DMSO-d$_6$) δ: 8.80 (d; 2H), 8.10 (d, 2H), 7.90 (d, 2H), 7.70 (m, 1H), 7.60 (m, 2H), 7.25 (s, 1H) ppm.

Step 11.2. 6-Chloro-2-phenyl-3-pyrid-4-ylimidazo[1,2-b]pyridazine

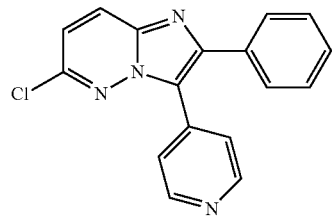 [SMILES: Clc1ccc2nc(-c3ccccc3)c(-c3ccncc3)n2n1]

A mixture of 13 g (36.5 mmol) of 2-bromo-1-phenyl-2-pyrid-4-ylethanone (CAS No.: 741633-76-1) and 18.9 g (146 mmol) of 6-chloropyridazin-3-ylamine in 200 mL of ethanol is maintained at 90° C. for 5 hours 30 minutes. After cooling, the solvent is evaporated off under reduced pressure, the medium is taken up in 50 mL of water and the product is extracted with ethyl acetate. The organic phases are dried over magnesium sulfate and then concentrated under reduced pressure.

The solid obtained is recrystallized from 50 mL of methanol to give 4.0 g of yellow crystals after drying.

$^1$H NMR (CDCl$_3$) δ: 8.80 (d, 2H), 8.10 (d, 1H), 7.55-7.80 (m, 4H), 7.50 (m, 2H), 7.35 (s, 1H), 7.20 (d, 1H) ppm.

Step 11.3. 2-Phenyl-3-pyrid-4-yl-6-(4-pyrrolidin-1-ylpiperid-1-yl)imidazo[1,2-b]pyridazine

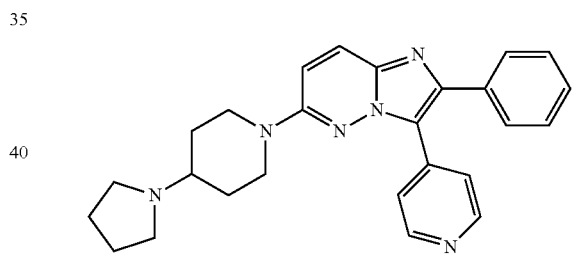

A mixture of 4.03 g (13.1 mmol) of 6-chloro-2-phenyl-3-pyrid-4-ylimidazo[1,2-b]pyridazine and 4.4 g (29 mmol) of 4-pyrrolidin-1-ylpiperidine in 50 mL of ethanol is heated at 155° C. for 4 hours. After cooling, the solvent is evaporated off under reduced pressure and the residue is chromatographed on silica gel, eluting with a mixture of dichloromethane and methanol (93:7).

The product is then recrystallized from 40 mL of methanol to give 1.5 g of yellow crystals after drying under reduced pressure.

m.p.: 165.0-165.5° C.

$^1$H NMR (CDCl$_3$) δ: 8.65 (d; 2H), 7.80 (d, 1H), 7.65 (m, 4H), 7.35 (m, 3H), 6.95 (d, 1H), 4.10 (m, 2H), 3.00 (m, 2H), 2.60 (m, 4H), 2.55 (m, 1H), 2.05 (m, 2H), 1.85 (m, 4H), 1.65 (m, 2H) ppm.

BIOLOGICAL EXAMPLES

The capacity of the compounds of the invention to inhibit the phosphorylation of casein by casein kinases 1 epsilon and delta may be evaluated according to the procedure described in document US 2005/0 131 012.

Filter-Plate Assay of ATP-$^{33}$P for the Screening of CK1 Epsilon Inhibitors:

The effect of the compounds on inhibition of the phosphorylation of casein by the enzyme casein kinase 1 epsilon (CK1 epsilon) is measured, using a casein assay via filtration of ATP-$^{33}$P in vitro.

Casein kinase 1 epsilon (0.58 mg/ml) is obtained via fermentation and purification processes performed according to methods that are well known to those skilled in the art, or may also be obtained from Invitrogen Corporation™ (human CK1 epsilon).

The compounds are tested at five different concentrations so as to generate IC$_{50}$ values, i.e. the concentration at which a compound is capable of inhibiting the enzymatic activity by 50%, or alternatively the percentage of inhibition at a concentration of 10 micromolar.

"U"-bottomed Falcon plates are prepared by placing 5 µL of solutions of the compounds according to the invention at concentrations of 10, 1, 0.1, 0.01 or 0.001 µM in different wells. The solutions of the compounds according to the invention at these various concentrations are prepared by diluting in a test buffer (Tris 50 mM pH 7.5, MgCl$_2$ 10 M, DTT 2 mM and EGTA 1 mM) a stock solution in DMSO at a concentration of 10 mM. Next, 5 µL of dephosphorylated casein are added to a final concentration of 0.2 ng/µL, 20 µL of CK1 epsilon to a final concentration of 3 µg/µL, and 20 µL of ATP-$^{33}$P to a final concentration of 0.02 µCi/µL mixed with cold ATP (10 µM final—approximately 2 10$^6$ CPM per well). The final total test volume per well is equal to 50 µL.

The "U"-bottomed Falcon® test plate mentioned above is vortexed, and then incubated at room temperature for 2 hours. After 2 hours the reaction is stopped by adding an ice-cold solution of 65 µL of cold ATP (2 mM) prepared in test buffer.

100 µL of the reaction mixture are then transferred from the "U"-bottomed Falcon® plate into Millipore® MAPH filter plates, preimpregnated with 25 µL of ice-cold 100% TCA.

The Millipore MAPH filter plates are agitated gently and are left to stand at room temperature for at least 30 minutes to precipitate the proteins.

After 30 minutes, the filter plates are sequentially washed and filtered with 2 150 µL of 20% TCA, 2 150 µL of 10% TCA and 2 150 µL of 5% TCA (6 washes in total per plate/900 µL per well).

The plates are left to dry overnight at room temperature. Next, 40 µL of Microscint-20 Packard® scintillation liquid are added per well and the plates are closed in a leak tight manner. The radiation emitted by each well is then measured for 2 minutes in a TopCount NXT Packard® scintillation counter, in which the values of CPM/well are measured.

The percentage inhibition of the capacity of the enzyme to phosphorylate the substrate (casein) is determined for each concentration of test compound. These inhibition data expressed as percentages are used to calculate the IC$_{50}$ value for each compound compared with the controls.

The kinetic studies determined the K$_M$ value for ATP as being 21 µM in this test system. Under these conditions, the compounds of the invention that are the most active have IC$_{50}$ values (concentrations that inhibit 50% of the enzymatic activity of casein kinase 1 epsilon or casein kinase 1 delta) of between 1 nM and 200 nM.

Table 2 below gives the IC$_{50}$ values for the inhibition of phosphorylation of casein kinase 1 epsilon for a number of compounds according to the invention.

TABLE 2

| Compound | CK1 epsilon IC$_{50}$ (nM) |
| --- | --- |
| 1 | 3 |
| 3 | 1 |
| 30 | 60 |
| 147 | 22-116 |
| 153 | 8 |

The capacity of the compounds of the invention to inhibit the phosphorylation of casein by the casein kinases 1 epsilon and delta may be evaluated using an FRET (Fluorescence Resonance Energy Transfer) fluorescence test with the aid of the "Z'Lyte™ kinase assay kit" (reference PV3670; Invitrogen Corporation™) according to the manufacturer's instructions.

The casein kinases 1 used are obtained from Invitrogen Corporation (human CK1 epsilon PV3500 and human CK1 delta PV3665).

A peptide substrate, labeled at both ends with a fluorophore-donating group (coumarin) and a fluorophore-accepting group (fluorescein) constituting an FRET system is dephosphorylated in the presence of ATP by casein kinase 1 epsilon or delta in the presence of increasing concentrations of compounds of the invention.

The mixture is treated with a site-specific protease that specifically cleaves the substrate peptide to form two fluorescent fragments having a large fluorescence emission ratio.

The fluorescence observed is thus related to the capacity of the products of the invention to inhibit the phosphorylation of the substrate peptide by casein kinase 1 epsilon or casein kinase 1 delta.

The compounds of the invention are dissolved at different concentrations starting with a 10 mM stock solution in DMSO diluted in a buffer containing 50 mM HEPS, pH 7.5, 1 mM EGTA, 0.01% Brij-35, 10 mM MgCl$_2$ for casein kinase 1 epsilon and supplemented with Trizma Base (50 mM), pH 8.0 and NaN$_3$ (0.01% final) for casein kinase 1 delta.

The phosphorylation of the substrate peptide SER/THR 11 obtained from Invitrogen Corporation™ is performed at a final concentration of 2 µM. The ATP concentration is 4 times the K$_M$, this value being 2 µM for casein kinase 1 epsilon and 4 µM for casein kinase 1 delta.

The emitted fluorescence is measured at wavelengths of 445 and 520 nm (excitation at 400 nm). Under these conditions, the compounds of the invention that are the most active have IC$_{50}$ values (concentration that inhibits 50% of the enzymatic activity of casein kinase 1 epsilon or casein kinase 1 delta) of between 1 nM and 200 nM.

Table 3 below gives the IC$_{50}$ values for the inhibition of phosphorylation of casein kinase 1 delta for a number of compounds according to the invention.

TABLE 3

| Compound | CK1 delta IC$_{50}$ (nM) |
| --- | --- |
| 31 | 91-93 |
| 50 | 5 |
| 81 | 59-110 |
| 147 | 50-53 |

It is thus seen that the compounds according to the invention have inhibitory activity on the enzyme casein kinase 1 epsilon or casein kinase 1 delta.

Experimental Protocols for Circadian Cell Assay

Mper1-luc Rat-1 (P2C4) fibroblast cultures were prepared by dividing the cultures every 3-4 days (about 10-20% of confluence) on 150 cm² degassed polystyrene tissue culture flasks (Falcon® #35-5001) and maintained in growth medium [EMEM (Cellgro #10-010-CV); 10% fetal bovine serum (FBS; Gibco #16000-044); and 50 I.U./mL of penicillin-streptomycin (Cellgro #30-001-CI)] at 37° C. and under 5% $CO_2$.

Cells obtained from Rat-1 fibroblast cultures at 30-50% of confluence as described above were co-transfected with vectors containing the selection marker for resistance to zeocin for a stable transfection and a luciferase reporter gene directed by the promoter mPer-1. After 24 to 48 hours, the cultures were divided on 96-well plates and maintained in growth medium supplemented with 50-100 μg/mL of zeocin (Invitrogen® #45-0430) for 10-14 days. The zeocin-resistant stable transfectants were evaluated for expression of the reporter by adding to the growth medium luciferin 100 μM (Promega® #E1603®) and by assaying the luciferase activity on a TopCount® scintillation counter (Packard model #C384V00). The Rat-1 cell clones expressing both zeocin resistance and luciferase activity directed by mPer1 were serum-shock synchronized with 50% horse serum [HS (Gibco® #16050-122)] and the activity of the circadian reporter was evaluated. The P2C4 clone of fibroblasts Mper1-luc Rat-1 was selected to test the compound.

The Mper1-luc Rat-1 (P2C4) fibroblasts at 40-50% of confluence obtained according to the protocol described above were plated out onto 96-well opaque tissue culture plates (Perkin Elmer® #6005680). The cultures are maintained in growth medium supplemented with 100 μg/mL of zeocin (Invitrogen #45-0430) until they reached 100% of confluence (48-72 hours). The cultures were then synchronized with 100 μL of synchronization medium [EMEM (Cellgro #10-010-CV); 100 I.U./mL of penicillin-streptomycin (Cellgro #30-001-C1); 50% HS (Gibco #16050-122)] for 2 hours at 37° C. and under 5% $CO_2$. After synchronization, the cultures were rinsed with 100 μL of EMEM (Cellgro #10-010-CV) for 10 minutes at room temperature. After rinsing, the medium is replaced with 300 μL of $CO_2$-independent medium [$CO_2$I (Gibco #18045-088); L-glutamine 2 mM (Cellgro #25-005-C1); 100 I.U./mL of penicillin-streptomycin (Cellgro #30-001-C1); luciferin 100 μM (Promega #E 1603)]. The compounds of the invention tested for the circadian effects were added to $CO_2$-independent medium in DMSO at 0.3% (final concentration). The cultures were immediately closed in a leak tight manner with TopSeal-A® film (Packard #6005185) and transferred for the luciferase activity measurement.

After synchronization, the test plates were maintained at 37° C. in a tissue culture oven (Form a Scientific Model #3914). The in vivo luciferase activity was estimated by measuring the relative light emission on a TopCount scintillation counter (Packard model #C384V00).

The period analysis was performed either by determining the interval between the relative light emission minima over several days or by Fourier transform.

The two methods produced a virtually identical period estimation on a range of circadian periods. The power is given in CE Delta (t+1 h), which is presented as the effective micromolar concentration that induce a 1-hour prolongation of the period. The data were analyzed by adjusting a hyperbolic curve to the data expressed as change of period (y-axis) as a function of the concentration of the test compound (x-axis) in the XLfit™ software and the CE Delta (t+1 h) was interpolated from this curve.

Table 4 below gives the CE Delta (t+1 h) for a number of compounds according to the invention.

TABLE 4

| Compound | CE Delta (t + 1 h) (nM) |
|---|---|
| 50 | 28 |
| 115 | 2 |
| 146 | 39 |
| 153 | 2-9 |

By inhibiting the enzymes CK1 epsilon and/or CK1 delta, the compounds that are the subject of the invention modulate the circadian periodicity, and may be useful for treating circadian rhythm disorders.

The compounds according to the invention may especially be used for the preparation of a medicament for preventing or treating sleep disorders; circadian rhythm disorders, especially such as those caused by jetlag or shift work.

Among the sleep disorders that are especially distinguished are primary sleep disorders such as dyssomnia (for example primary insomnia), parasomnia, hypersomnia (for example excessive somnolence), narcolepsy, sleep disorders related to sleep apnea, sleep disorders related to the circadian rhythm and other unspecified dyssomnias, sleep disorders associated with medical/psychiatric disorders.

The compounds that are the subject of the invention also cause a circadian phase shift and such a property may be useful in the context of a potential monotherapy or combined therapy that is clinically effective in the case of mood disorders.

Among the mood disorders that are especially distinguished are depressive disorders (unipolar depression), bipolar disorders, mood disorders caused by a general medical complaint and also mood disorders induced by pharmacological substances. Among the bipolar disorders that are especially distinguished are bipolar I disorders and bipolar II disorders, especially including seasonal affective disorders.

The compounds that are the subject of the invention, which modulate the circadian periodicity, may be useful in the treatment of anxiety and depressive disorders caused in particular by an impairment in the secretion of CRF.

Among the depressive disorders that are especially distinguished are major depressive disorders, dysthymic disorders and other unspecified depressive disorders.

The compounds that are the subject of the invention, which modulate the circadian periodicity, may be useful for preparing a medicament for treating diseases related to dependency on abuse substances such as cocaine, morphine, nicotine, ethanol and cannabis.

By inhibiting casein kinase 1 epsilon and/or casein kinase 1 delta, the compounds according to the invention may be used for preparing medicaments, especially for preparing a medicament for preventing or treating diseases related to hyperphosphorylation of the tau protein, especially Alzheimer's disease.

These medicaments also find their use in therapy, especially in the treatment or prevention of diseases caused or exacerbated by the proliferation of cells and in particular of tumor cells.

As tumor cell proliferation inhibitors, these compounds are useful in the prevention and treatment of liquid tumors such as leukemias, solid tumors that are both primary and metastatic, carcinomas and cancers, in particular: breast cancer; lung cancer; small intestine cancer and colorectal cancer; cancer of the respiratory pathways, of the oropharynx and of the hypopharynx; cancer of the esophagus; liver cancer, stomach cancer, cancer of the bile ducts, cancer of the bile vesicle, pancreatic cancer; cancers of the urinary pathways including the kidney, urothelium and bladder; cancers of the female genital tract, including cancer of the uterus, of the cervix, of the ovaries, choriocarcinoma and trophoblastoma; cancers of the male genital tract, including cancer of the prostate, of the seminal vesicles, of the testicles and germinal cell tumors; cancers of the endocrine glands, including cancer of the thyroid, of the pituitary and of the adrenal glands; skin cancers including hemiangiomas, melanomas and sarcomas, including Kaposi's sarcoma; brain, nerve, eye or meningeal tumors, including astrocytomas, gliomas, glioblastomas, retinoblastomas, neurinomas, neuroblastomas, schwannomas and meningiomas; malignant hematopoietic tumors; leukemias (Acute Lymphocytic Leukemia (ALL), Acute Myeloid Leukemia (AML), Chronic Myeloid Leukemia (CML), Chronic lymphocytic leukemia (CLL)) chloromas, plasmocytomas, T or B cell leukemias, Hodgkin or non-Hodgkin lymphomas, myelomas and various malignant hemopathies.

The compounds according to the invention may thus be used for the preparation of medicaments, in particular of medicaments for inhibiting casein kinase 1 epsilon and/or casein kinase 1 delta.

Thus, according to another of its aspects, a subject of the invention is medicaments comprising a compound of formula (I), or an addition salt thereof with a pharmaceutically acceptable acid, or alternatively a hydrate or solvate of the compounds of formula (I).

According to another of its aspects, the present invention relates to pharmaceutical compositions comprising, as active principle, a compound according to the invention. These pharmaceutical compositions contain an effective dose of at least one compound according to the invention or a pharmaceutically acceptable salt, a hydrate or solvate of said compound, and also at least one pharmaceutically acceptable excipient.

Said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to man and animals for the prophylaxis or treatment of the above disorders or diseases.

The appropriate unit administration forms include oral-route forms such as tablets, soft or hard gel capsules, powders, granules and oral solutions or suspensions, sublingual, buccal, intratracheal, intraocular and intranasal administration forms, inhalation forms, topical, transdermal, subcutaneous, intramuscular or intravenous administration forms, rectal administration forms and implants. For topical administration, the compounds according to the invention may be used in creams, gels, ointments or lotions.

By way of example, a unit administration form of a compound according to the invention in tablet form may comprise the following components:

| Compound according to the invention | 50.0 mg |
|---|---|
| Mannitol | 223.75 mg |
| Sodium croscarmellose | 6.0 mg |

-continued

| Corn starch | 15.0 mg |
|---|---|
| Hydroxypropylmethylcellulose | 2.25 mg |
| Magnesium stearate | 3.0 mg |

Via the oral route, the dose of active principle administered per day may range from 0.1 to 20 mg/kg, in one or more dosage intakes.

There may be particular cases in which higher or lower dosages are appropriate; such dosages are not outside the context of the invention. According to the usual practice, the dosage that is appropriate to each patient is determined by the practitioner according to the mode of administration and the weight and response of said patient.

According to another of its aspects, the present invention also relates to a method for treating the pathologies indicated above, which comprises the administration to a patient of an effective dose of a compound according to the invention, or a pharmaceutically acceptable salt or hydrate or solvate thereof.

What is claimed is:

1. A process for preparing a compound of formula (I),

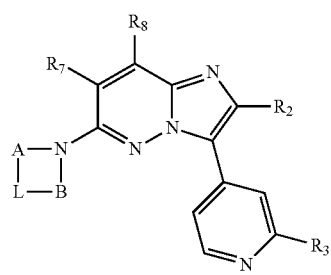

or salt thereof, which comprises
reacting a compound of formula (IIa):

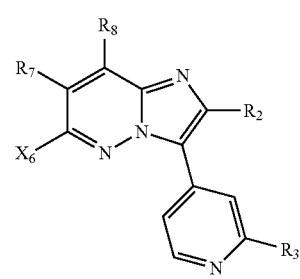

with an amine of formula (IIIa):

in a polar solvent
wherein X6 is a leaving group;
$R_2$ represents an aryl group optionally substituted with one or more substituents selected from the group consisting of halogen atoms, $C_{1-6}$ alkyl, $C_{1-6}$ alkyloxy, $C_{1-6}$ alkylthio, $C_{1-6}$ fluoroalkyl, $C_{1-6}$-fluoroalkyloxy and —CN;

$R_3$ represents a hydrogen atom, $C_{1-3}$ alkyl, —$NR_4R_5$, hydroxyl or $C_{1-4}$ alkyloxy;

A represents a group $C_{1-7}$-alkylene optionally substituted with one or two groups $R_a$;

B represents a group $C_{1-7}$-alkylene optionally substituted with a group $R_b$;

L represents either a nitrogen atom substituted with a group $R_c$ or $R_d$, or a carbon atom substituted with a group $R_{e1}$ and a group $R_d$ or two groups $R_{e2}$;

the carbon atoms of A and B being optionally substituted with one or more groups $R_f$ which may be identical to or different than each other;

$R_a$, $R_b$ and $R_c$ are defined such that:

two groups $R_a$ may together form a group $C_{1-6}$-alkylene;

$R_a$ and $R_b$ may together form a bond or a group $C_{1-6}$-alkylene;

$R_a$ and $R_c$ may together form a bond or a group $C_{1-6}$-alkylene;

$R_b$ and $R_c$ may together form a bond or a group $C_{1-6}$-alkylene;

$R_d$ represents a group selected from the group consisting of a hydrogen atom and the groups $C_{1-6}$-alkyl, $C_{3-7}$-cycloalkyl, $C_{3-7}$-cycloalkyl, $C_{1-6}$-alkyl, $C_{1-6}$-alkylthio, $C_{1-6}$-alkyl, $C_{1-6}$-alkyloxy, $C_{1-6}$-alkyl, $C_{1-6}$-fluoroalkyl, benzyl, $C_{1-6}$-acyl and hydroxy-$C_{1-6}$-alkyl;

$R_{e1}$ represents a group —$NR_4R_5$ or a cyclic monoamine optionally comprising an oxygen atom, the cyclic monoamine being optionally substituted with one or more substituents selected from the group consisting of a fluorine atom and the groups $C_{1-6}$-alkyl, $C_{1-6}$-alkyloxy and hydroxyl;

two groups $R_{e2}$ form, with the carbon atom that bears them, a cyclic monoamine optionally comprising an oxygen atom, this cyclic monoamine being optionally substituted with one or more groups $R_f$ which may be identical to or different than each other;

$R_f$ represents a group $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or benzyl;

$R_4$ and $R_5$ represent, independently of each other, a hydrogen atom or a group $C_{1-4}$ alkyl, $C_{3-7}$-cycloalkyl or $C_{3-7}$-cycloalkyl-$C_{1-6}$-alkyl; and $R_7$ and $R_8$ represent, independently of each other, a hydrogen atom or a group $C_{1-6}$-alkyl.

2. A process for preparing a compound of formula (I),

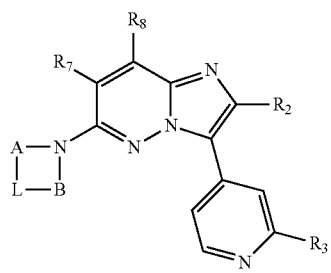

or salt thereof
which comprises
reacting a compound of formula (Vb):

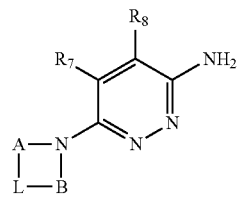

with a compound of formula (VIb):

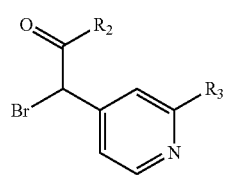

in a polar solvent, wherein $R_2$ represents an aryl group optionally substituted with one or more substituents selected from the group consisting of halogen atoms, $C_{1-6}$ alkyl, $C_{1-6}$ alkyloxy, $C_{1-6}$ alkylthio, $C_{1-6}$ fluoroalkyl, $C_{1-6}$-fluoroalkyloxy and —CN;

$R_3$ represents a hydrogen atom, $C_{1-3}$ alkyl, —$NR_4R_5$, hydroxyl or $C_{1-4}$ alkyloxy;

A represents a group $C_{1-7}$-alkylene optionally substituted with one or two groups $R_a$;

B represents a group $C_{1-7}$-alkylene optionally substituted with a group $R_b$;

L represents either a nitrogen atom substituted with a group $R_c$ or $R_d$, or a carbon atom substituted with a group $R_{e1}$ and a group $R_d$ or two groups $R_{e2}$;

the carbon atoms of A and B being optionally substituted with one or more groups $R_f$ which may be identical to or different than each other;

$R_a$, $R_b$ and $R_c$ are defined such that:

two groups $R_a$ may together form a group $C_{1-6}$-alkylene;

$R_a$ and $R_b$ may together form a bond or a group $C_{1-6}$-alkylene;

$R_a$ and $R_c$ may together form a bond or a group $C_{1-6}$-alkylene;

$R_b$ and $R_c$ may together form a bond or a group $C_{1-6}$-alkylene;

$R_d$ represents a group selected from the group consisting of a hydrogen atom and the groups $C_{1-6}$-alkyl, $C_{3-7}$-cycloalkyl, $C_{3-7}$-cycloalkyl-$C_{1-6}$-alkyl, $C_{1-6}$-alkylthio-$C_{1-6}$-alkyl, $C_{1-6}$-alkyloxy-$C_{1-6}$-alkyl, $C_{1-6}$-fluoroalkyl, benzyl, $C_{1-6}$-acyl and hydroxy-$C_{1-6}$-alkyl;

$R_{e1}$ represents a group —$NR_4R_5$ or a cyclic monoamine optionally comprising an oxygen atom, the cyclic monoamine being optionally substituted with one or more substituents selected from the group consisting of a fluorine atom and the groups $C_{1-6}$-alkyl, $C_{1-6}$-alkyloxy and hydroxyl;

two groups $R_{e2}$ form, with the carbon atom that bears them, a cyclic monoamine optionally comprising an oxygen atom, this cyclic monoamine being optionally substituted with one or more groups $R_f$ which may be identical to or different than each other;

$R_f$ represents a group $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or benzyl;

$R_4$ and $R_5$ represent, independently of each other, a hydrogen atom or a group $C_{1-4}$ alkyl, $C_{3-7}$-cycloalkyl or $C_{3-7}$-cycloalkyl-$C_{1-6}$-alkyl; and $R_7$ and $R_8$ represent, independently of each other, a hydrogen atom or a group $C_{1-6}$-alkyl.

3. A process for preparing a compound of formula (I)

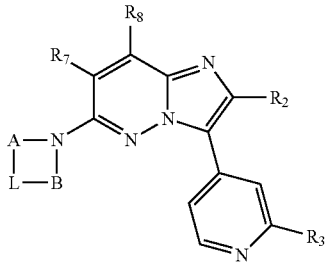

or salt thereof comprising:
reacting a compound of formula (IId):

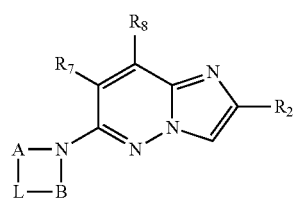

with a compound of formula (IVd):

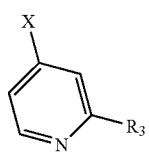

in the presence of a catalyst and a mineral base, and in a polar aprotic solvent wherein X is an iodine atom;

$R_2$ represents an aryl group optionally substituted with one or more substituents selected from the group consisting of halogen atoms, $C_{1-6}$ alkyl, $C_{1-6}$ alkyloxy, $C_{1-6}$ alkylthio, $C_{1-6}$ fluoroalkyl, $C_{1-6}$-fluoroalkyloxy and —CN;

$R_3$ represents a hydrogen atom, $C_{1-3}$ alkyl, —NR$_4$R$_5$, hydroxyl or $C_{1-4}$ alkyloxy;

A represents a group $C_{1-7}$-alkylene optionally substituted with one or two groups $R_a$;

B represents a group $C_{1-7}$-alkylene optionally substituted with a group $R_b$;

L represents either a nitrogen atom substituted with a group $R_c$ or $R_d$, or a carbon atom substituted with a group $R_{e1}$ and a group $R_d$ or two groups $R_{e2}$;

the carbon atoms of A and B being optionally substituted with one or more groups $R_f$ which may be identical to or different than each other;

$R_a$, $R_b$ and $R_c$ are defined such that:
two groups $R_a$ may together form a group $C_{1-6}$-alkylene;
$R_a$ and $R_b$ may together form a bond or a group $C_{1-6}$-alkylene;

$R_a$ and $R_c$ may together form a bond or a group $C_{1-6}$-alkylene;

$R_b$ and $R_c$ may together form a bond or a group $C_{1-6}$-alkylene;

$R_d$ represents a group selected from the group consisting of a hydrogen atom and the groups $C_{1-6}$-alkyl, $C_{3-7}$-cycloalkyl, $C_{3-7}$-cycloalkyl-$C_{1-6}$-alkyl, $C_{1-6}$-alkylthio-$C_{1-6}$-alkyl, $C_{1-6}$-alkyloxy-$C_{1-6}$-alkyl, $C_{1-6}$-fluoroalkyl, benzyl, $C_{1-6}$-acyl and hydroxy-$C_{1-6}$-alkyl, $R_{e1}$ represents a group —NR$_4$R$_5$ or a cyclic monoamine optionally comprising an oxygen atom, the cyclic monoamine being optionally substituted with one or more substituents selected from the group consisting of a fluorine atom and the groups $C_{1-6}$-alkyl, $C_{1-6}$-alkyloxy and hydroxyl;

two groups $R_{e2}$ form, with the carbon atom that bears them, a cyclic monoamine optionally comprising an oxygen atom, this cyclic monoamine being optionally substituted with one or more groups $R_f$, which may be identical to or different than each other $R_f$ represents a group $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or benzyl;

$R_4$ and $R_5$ represent, independently of each other, a hydrogen atom or a group $C_{1-4}$ alkyl, $C_{3-7}$-cycloalkyl or $C_{3-7}$-cycloalkyl-$C_{1-6}$-alkyl; and $R_7$ and $R_8$ represent, independently of each other, a hydrogen atom or a group $C_{1-6}$-alkyl.

4. A process for preparing a compound of formula (I)

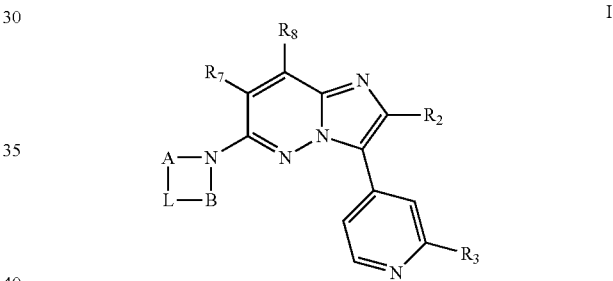

or salt thereof comprising:
reacting a compound of formula (IIc):

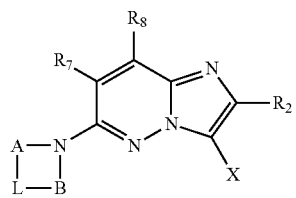

with a compound of formula (IVc):

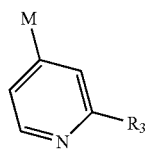

wherein M represents a trialkylstannyl group or a dihydroxyboryl or dialkyloxyboryl group;

X represents an iodine or bromine atom;

$R_2$ represents an aryl group optionally substituted with one or more substituents selected from the group consisting of halogen atoms, $C_{1-6}$ alkyl, $C_{1-6}$ alkyloxy, $C_{1-6}$ alkylthio, $C_{1-6}$ fluoroalkyl, $C_{1-6}$-fluoroalkyloxy and —CN;

$R_3$ represents a hydrogen atom, $C_{1-3}$ alkyl, $-NR_4R_5$, hydroxyl or $C_{1-4}$ alkyloxy;

A represents a group $C_{1-7}$-alkylene optionally substituted with one or two groups $R_a$;

B represents a group $C_{1-7}$-alkylene optionally substituted with a group $R_b$;

L represents either a nitrogen atom substituted with a group $R_c$ or $R_d$, or a carbon atom substituted with a group $R_{e1}$ and a group $R_d$ or two groups $R_{e2}$;

the carbon atoms of A and B being optionally substituted with one or more groups $R_f$ which may be identical to or different than each other;

$R_a$, $R_b$ and $R_c$ are defined such that:

two groups $R_a$ may together form a group $C_{1-6}$-alkylene;

$R_a$ and $R_b$ may together form a bond or a group $C_{1-6}$-alkylene;

$R_a$ and $R_c$ may together form a bond or a group $C_{1-6}$-alkylene;

$R_b$ and $R_c$ may together form a bond or a group $C_{1-6}$-alkylene;

$R_d$ represents a group selected from the group consisting of a hydrogen atom and the groups $C_{1-6}$-alkyl, $C_{3-7}$-cycloalkyl, $C_{3-7}$-cycloalkyl-$C_{1-6}$-alkyl, $C_{1-6}$-alkylthio-$C_{1-6}$-alkyl, $C_{1-6}$-alkyloxy-$C_{1-6}$-alkyl, $C_{1-6}$-fluoroalkyl, benzyl, $C_{1-6}$-acyl and hydroxy-$C_{1-6}$-alkyl;

$R_{e1}$ represents a group $-NR_4R_5$ or a cyclic monoamine optionally comprising an oxygen atom, the cyclic monoamine being optionally substituted with one or more substituents selected from the group consisting of a fluorine atom and the groups $C_{1-6}$-alkyl, $C_{1-6}$-alkyloxy and hydroxyl;

two groups $R_{e2}$ form, with the carbon atom that bears them, a cyclic monoamine optionally comprising an oxygen atom, this cyclic monoamine being optionally substituted with one or more groups $R_f$ which may be identical to or different than each other;

$R_f$ represents a group $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or benzyl;

$R_4$ and $R_5$ represent, independently of each other, a hydrogen atom or a group $C_{1-4}$ alkyl, $C_{3-7}$-cycloalkyl or $C_{3-7}$-cycloalkyl-$C_{1-6}$-alkyl; and $R_7$ and $R_8$ represent, independently of each other, a hydrogen atom or a group $C_{1-6}$-alkyl.

5. A process for preparing a compound of formula (I) or salt thereof or salt thereof comprising:

a) reacting a compound of formula (IId):

(IId)

with a compound of formula (IVe):

(IVe)

in the presence of an alkyl chloroformate, to obtain a compound of formula (IIe):

(IIe)

and b) reacting the product of formula (IIe) obtained in step a) with an oxidizing agent to obtain a compound of formula (I) in which $R_3$ represents a hydrogen atom or a group $C_{1-3}$-alkyl, $R_2$ represents an aryl group optionally substituted with one or more substituents selected from the group consisting of halogen atom, $C_{1-6}$ alkyl, $C_{1-6}$ alkyloxy, $C_{1-6}$ alkylthio, $C_{1-6}$-fluoroalkyl, $C_{1-6}$-fluoroalkyloxy and $-CN$;

A represents a group $C_{1-7}$-alkylene optionally substituted with one or two groups $R_a$;

B represents a group $C_{1-7}$-alkylene optionally substituted with a group $R_b$;

L represents either a nitrogen atom substituted with a group $R_c$ or $R_d$, or a carbon atom substituted with a group $R_{e1}$ and a group $R_d$ or two groups $R_{e2}$;

the carbon atoms of A and B being optionally substituted with one or more groups $R_f$ which may be identical to or different than each other;

$R_a$, $R_b$ and $R_c$ are defined such that:

two groups $R_a$ may together form a group $C_{1-6}$-alkylene;

$R_a$ and $R_b$ may together form a bond or a group $C_{1-6}$-alkylene;

$R_a$ and $R_c$ may together form a bond or a group $C_{1-6}$-alkylene;

$R_b$ and $R_c$ may together form a bond or a group $C_{1-6}$-alkylene;

$R_d$ represents a group selected from the group consisting of a hydrogen atom and the groups $C_{1-6}$-alkyl, $C_{3-7}$-cycloalkyl, $C_{3-7}$-cycloalkyl-$C_{1-6}$-alkyl, $C_{1-6}$-alkylthio-$C_{1-6}$-alkyl, $C_{1-6}$-alkyloxy-$C_{1-6}$-alkyl, $C_{1-6}$-fluoroalkyl, benzyl, $C_{1-6}$-acyl and hydroxy-$C_{1-6}$-alkyl, $R_{e1}$ represents a group —$NR_4R_5$ or a cyclic monoamine optionally comprising an oxygen atom, the cyclic monoamine being optionally substituted with one or more substituents selected from the group consisting of a fluorine atom and the groups $C_{1-6}$-alkyl, $C_{1-6}$-alkyloxy and hydroxyl;

two groups $R_{e2}$ form, with the carbon atom that bears them, a cyclic monoamine optionally comprising an oxygen atom, this cyclic monoamine being optionally substituted with one or more groups $R_f$, which may be identical to or different than each other;

$R_f$ represents a group $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or benzyl;

$R_4$ and $R_5$ represent, independently of each other, a hydrogen atom or a group $C_{1-4}$ alkyl, $C_{3-7}$-cycloalkyl or $C_{3-7}$-cycloalkyl-$C_{1-6}$-alkyl; and $R_7$ and $R_8$ represent, independently of each other, a hydrogen atom or a group $C_{1-6}$-alkyl;

or a salt thereof.

6. A method for treating a circadian rhythm disorder in a patient comprising administering to said patient a therapeutically effective amount of a compound of formula (I)

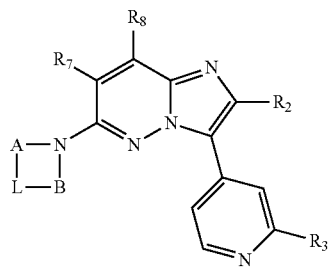

or a pharmaceutically acceptable salt thereof,
wherein $R_2$ represents an aryl group optionally substituted with one or more substituents selected from the group consisting of halogen atoms, $C_{1-6}$ alkyl, $C_{1-6}$ alkyloxy, $C_{1-6}$ alkylthio, $C_{1-8}$ fluoroalkyl, $C_{1-6}$-fluoroalkyloxy and —CN;

$R_3$ represents a hydrogen atom, $C_{1-3}$ alkyl, —$NR_4R_5$, hydroxyl or $C_{1-4}$ alkyloxy;

A represents a group $C_{1-7}$-alkylene optionally substituted with one or two groups $R_a$;

B represents a group $C_{1-7}$-alkylene optionally substituted with a group $R_b$;

L represents either a nitrogen atom substituted with a group $R_c$ or $R_d$, or a carbon atom substituted with a group $R_{e1}$ and a group $R_d$ or two groups $R_{e2}$;

the carbon atoms of A and B being optionally substituted with one or more groups $R_f$, which may be identical to or different than each other;

$R_a$, $R_b$ and $R_c$ are defined such that:
two groups $R_a$ may together form a group $C_{1-6}$-alkylene;
$R_a$ and $R_b$ may together form a bond or a group $C_{1-6}$-alkylene;
$R_a$ and $R_c$ may together form a bond or a group $C_{1-6}$-alkylene;
$R_b$ and $R_c$ may together form a bond or a group $C_{1-6}$-alkylene;

$R_d$ represents a group selected from the group consisting of a hydrogen atom and the groups $C_{1-6}$-alkyl, $C_{3-7}$-cycloalkyl, $C_{3-7}$-cycloalkyl-$C_{1-6}$-alkyl, $C_{1-6}$-alkylthio-$C_{1-6}$-alkyl, $C_{1-6}$-alkyloxy-$C_{1-6}$-alkyl, $C_{1-6}$-fluoroalkyl, benzyl, $C_{1-6}$-alkylC(O) and hydroxy-$C_{1-6}$-alkyl;

$R_{e1}$ represents a group —$NR_4R_5$ or pyrrolidinyl or morpholinyl, optionally substituted with one or more substituents selected from the group consisting of a fluorine atom and the groups fluoro $C_{1-6}$-alkyl, $C_{1-6}$-alkyloxy and hydroxyl;

two groups $R_{e2}$ form, with the carbon atom that bears them, a cyclic monoamine optionally comprising an oxygen atom, this cyclic monoamine being pyrrolidinyl, piperidinyl, or morpholinyl optionally substituted with one or more groups $R_f$, which may be identical to or different than each other;

$R_f$ represents a group $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or benzyl;

$R_4$ and $R_5$ represent, independently of each other, a hydrogen atom or a group $C_{1-4}$ alkyl, $C_{3-7}$-cycloalkyl or $C_{3-7}$-cycloalkyl-$C_{1-6}$-alkyl; and $R_7$ and $R_8$ represent, independently of each other, a hydrogen atom or a group $C_{1-6}$-alkyl.

7. The method for treating a circadian rhythm disorder in a patient according to claim 6 wherein the compound is selected from the group consisting of:
2-Phenyl-6-piperazin-1-yl-3-pyrid-4-ylimidazo[1,2-b]pyridazine;
2-(4-Fluorophenyl)-6-piperazin-1-yl-3-pyrid-4-ylimidazo[1,2-b]pyridazine;
2-(4-Fluorophenyl)-7,8-dimethyl-6-piperazin-1-yl-3-pyrid-4-ylimidazo[1,2-b]pyridazine;
4-[2-(4-Fluorophenyl)-6-piperazin-1-ylimidazo[1,2-b]pyridazin-3-yl]pyrid-2-ylamine;
2-(4-Fluorophenyl)-3-(2-methoxypyrid-4-yl)-6-piperazin-1-ylimidazo[1,2-b]pyridazine;
2-(4-Chlorophenyl)-6-piperazin-1-yl-3-pyrid-4-ylimidazo[1,2-b]pyridazine;
2-(4-Chlorophenyl)-7-methyl-6-piperazin-1-yl-3-pyrid-4-ylimidazo[1,2-b]pyridazine;
2-(4-Chlorophenyl)-8-methyl-6-piperazin-1-yl-3-pyrid-4-ylimidazo[1,2-b]pyridazine;
2-(3,5-Dimethylphenyl)-6-piperazin-1-yl-3-pyrid-4-ylimidazo[1,2-b]pyridazine;
2-(3,5-Difluorophenyl)-6-piperazin-1-yl-3-pyrid-4-ylimidazo[1,2-b]pyridazine;
2-(3,5-Difluorophenyl)-3-(2-methylpyrid-4-yl)-6-piperazin-1-ylimidazo[1,2-b]pyridazine;
2-(3,4-Difluorophenyl)-6-piperazin-1-yl-3-pyrid-4-ylimidazo[1,2-b]pyridazine;
2-(3,5-Dichlorophenyl)-6-piperazin-1-yl-3-pyrid-4-ylimidazo[1,2-b]pyridazine;
2-(3,5-Dichlorophenyl)-3-(2-methylpyrid-4-yl)-6-piperazin-1-ylimidazo[1,2-b]pyridazine;
(±)-6-(3-Methylpiperazin-1-yl)-2-phenyl-3-pyrid-4-ylimidazo[1,2-b]pyridazine;
6-((R)-3-Methylpiperazin-1-yl)-2-phenyl-3-pyrid-4-ylimidazo[1,2-b]pyridazine;
6-((R)-3-Methylpiperazin-1-yl)-3-(2-methylpyrid-4-yl)-2-phenylimidazo[1,2-b]pyridazine;
6-((S)-3-Methylpiperazin-1-yl)-2-phenyl-3-pyrid-4-ylimidazo[1,2-b]pyridazine;
2-(3-Fluorophenyl)-6-((R)-3-methylpiperazin-1-yl)-3-pyrid-4-ylimidazo[1,2-b]pyridazine;
2-(4-Fluorophenyl)-6-(3-methylpiperazin-1-yl)-3-pyrid-4-ylimidazo[1,2-b]pyridazine;

2-(4-Fluorophenyl)-6-((R)-3-methylpiperazin-1-yl)-3-pyrid-4-ylimidazo[1,2-b]pyridazine;
2-(4-Fluorophenyl)-6-((S)-3-methylpiperazin-1-yl)-3-pyrid-4-ylimidazo[1,2-b]pyridazine;
2-(4-Fluorophenyl)-3-(2-methoxypyrid-4-yl)-6-((R)-3-methylpiperazin-1-yl)imidazo[1,2-b]pyridazine;
2-(3,4-Difluorophenyl)-6-((R)-3-methylpiperazin-1-yl)-3-pyrid-4-ylimidazo[1,2-b]pyridazine;
6-(3,3-Dimethylpiperazin-1-yl)-2-phenyl-3-pyrid-4-ylimidazo[1,2-b]pyridazine;
6-(3,3-Dimethylpiperazin-1-yl)-2-(4-fluorophenyl)-3-pyrid-4-ylimidazo[1,2-b]pyridazine;
6-(3,3-Dimethylpiperazin-1-yl)-2-(4-fluorophenyl)-3-(2-methoxypyrid-4-yl)imidazo[1,2-b]pyridazine;
2-(3,5-Dimethylphenyl)-6-(3,3-dimethylpiperazin-1-yl)-3-pyrid-4-ylimidazo[1,2-b]pyridazine;
2-(3,5-Dimethylphenyl)-6-(3,3-dimethylpiperazin-1-yl)-3-(2-methylpyrid-4-yl)imidazo[1,2-b]pyridazine;
4-[2-(3,5-Dimethylphenyl)-6-(3,3-dimethylpiperazin-1-yl)imidazo[1,2-b]pyridazin-3-yl]pyrid-2-ylamine;
2-(3,5-Difluorophenyl)-6-(3,3-dimethylpiperazin-1-yl)-3-pyrid-4-ylimidazo[1,2-b]pyridazine;
2-(3,5-Difluorophenyl)-6-(3,3-dimethylpiperazin-1-yl)-3-(2-methylpyrid-4-yl)imidazo[1,2-b]pyridazine;
4-[2-(3,5-Difluorophenyl)-6-(3,3-dimethylpiperazin-1-yl)imidazo[1,2-b]pyridazin-3-yl]pyrid-2-ylamine;
2-(3,5-Dichlorophenyl)-6-(3,3-dimethylpiperazin-1-yl)-3-pyrid-4-ylimidazo[1,2-b]pyridazine;
2-(3,5-Dichlorophenyl)-6-(3,3-dimethylpiperazin-1-yl)-3-(2-methylpyrid-4-yl)imidazo[1,2-b]pyridazine;
(±)-6-(3,4-Dimethylpiperazin-1-yl)-2-(4-fluorophenyl)-3-pyrid-4-ylimidazo[1,2-b]pyridazine;
6-((cis)-3,5-Dimethylpiperazin-1-yl)-2-phenyl-3-pyrid-4-ylimidazo[1,2-b]pyridazine;
6-((cis)-3,5-Dimethylpiperazin-1-yl)-3-(2-methylpyrid-4-yl)-2-phenylimidazo[1,2-b]pyridazine;
6-((cis)-3,5-Dimethylpiperazin-1-yl)-2-(3-fluorophenyl)-3-pyrid-4-ylimidazo[1,2-b]pyridazine;
6-((cis)-3,5-Dimethylpiperazin-1-yl)-2-(4-fluorophenyl)-3-pyrid-4-ylimidazo[1,2-b]pyridazine;
6-((cis)-3,5-Dimethylpiperazin-1-yl)-2-(4-fluorophenyl)-3-(2-methoxypyrid-4-yl)imidazo[1,2-b]pyridazine;
2-(3,5-Dimethylphenyl)-6-((cis)-3,5-dimethylpiperazin-1-yl)-3-pyrid-4-ylimidazo[1,2-b]pyridazine;
2-(3,4-Difluorophenyl)-6-((cis)-3,5-dimethylpiperazin-1-yl)-3-pyrid-4-ylimidazo[1,2-b]pyridazine;
2-(4-Chlorophenyl)-6-((cis)-3,5-dimethylpiperazin-1-yl)-7-methyl-3-pyrid-4-ylimidazo[1,2-b]pyridazine;
6-((cis)-3,5-Dimethylpiperazin-1-yl)-2-(4-fluorophenyl)-8-methyl-3-pyrid-4-ylimidazo[1,2-b]pyridazine;
2-(2-Chlorophenyl)-6-(4-methylpiperazin-1-yl)-3-pyrid-4-ylimidazo[1,2-b]pyridazine;
2-(3-Chlorophenyl)-6-(4-methylpiperazin-1-yl)-3-pyrid-4-ylimidazo[1,2-b]pyridazine;
2-(4-Chlorophenyl)-6-(4-methylpiperazin-1-yl)-3-pyrid-4-ylimidazo[1,2-b]pyridazine;
2-(3-Fluorophenyl)-6-(4-methylpiperazin-1-yl)-3-pyrid-4-ylimidazo[1,2-b]pyridazine;
2-(4-Fluorophenyl)-6-(4-methylpiperazin-1-yl)-3-pyrid-4-ylimidazo[1,2-b]pyridazine;
2-(3,4-Difluorophenyl)-6-(4-methylpiperazin-1-yl)-3-pyrid-4-ylimidazo[1,2-b]pyridazine;
2-(3-Methoxyphenyl)-6-(4-methylpiperazin-1-yl)-3-pyrid-4-ylimidazo[1,2-b]pyridazine;
2-(4-Methoxyphenyl)-6-(4-methylpiperazin-1-yl)-3-pyrid-4-ylimidazo[1,2-b]pyridazine;
6-(4-Methylpiperazin-1-yl)-3-pyrid-4-yl-2-p-tolylimidazo[1,2-b]pyridazine;
6-(4-Methylpiperazin-1-yl)-3-pyrid-4-yl-2-(4-trifluoromethylphenyl)imidazo[1,2-b]pyridazine;
2-(4-Fluorophenyl)-6-(4-methylpiperazin-1-yl)-3-(2-methylpyrid-4-yl)imidazo[1,2-b]pyridazine;
4-[2-(4-Fluorophenyl)-6-(4-methylpiperazin-1-yl)imidazo[1,2-b]pyridazin-3-yl]pyrid-2-ylamine;
{4-[2-(4-Fluorophenyl)-6-(4-methylpiperazin-1-yl)imidazo[1,2-b]pyridazin-3-yl]pyrid-2-yl}dimethylamine;
2-(4-Fluorophenyl)-3-(2-methoxypyrid-4-yl)-6-(4-methylpiperazin-1-yl)imidazo[1,2-b]pyridazine;
6-(4-Ethylpiperazin-1-yl)-2-(4-fluorophenyl)-3-pyrid-4-ylimidazo[1,2-b]pyridazine;
2-(3,5-Dimethylphenyl)-6-(4-ethylpiperazin-1-yl)-3-pyrid-4-ylimidazo[1,2-b]pyridazine;
2-[4-(2-Phenyl-3-pyrid-4-ylimidazo[1,2-b]pyridazin-6-yl)piperazin-1-yl]ethanol;
2-{4-[2-(3-Fluorophenyl)-3-pyrid-4-ylimidazo[1,2-b]pyridazin-6-yl]piperazin-1-yl}ethanol;
2-{4-[2-(4-Fluorophenyl)-3-pyrid-4-ylimidazo[1,2-b]pyridazin-6-yl]piperazin-1-yl}ethanol;
2-{4-[2-(4-Fluorophenyl)-3-(2-methoxypyrid-4-yl)imidazo[1,2-b]pyridazin-6-yl]piperazin-1-yl}ethanol;
2-{4-[2-(3,4-Difluorophenyl)-3-pyrid-4-ylimidazo[1,2-b]pyridazin-6-yl]piperazin-1-yl}ethanol;
2-{4-[2-(4-Chlorophenyl)-3-pyrid-4-ylimidazo[1,2-b]pyridazin-6-yl]piperazin-1-yl}ethanol;
2-{4-[3-(2-Aminopyrid-4-yl)-2-(4-chlorophenyl)imidazo[1,2-b]pyridazin-6-yl]piperazin-1-yl}ethanol;
2-(4-Chlorophenyl)-6-[4-(2-methoxyethyl)piperazin-1-yl]-3-pyrid-4-ylimidazo[1,2-b]pyridazine;
6-[4-(2-Fluoroethyl)piperazin-1-yl]-2-(4-fluorophenyl)-3-pyrid-4-ylimidazo[1,2-b]pyridazine;
6-[4-(2-Fluoroethyl)piperazin-1-yl]-2-(4-fluorophenyl)-3-(2-methoxypyrid-4-yl)imidazo[1,2-b]pyridazine;
2-Phenyl-3-pyrid-4-yl-6-[4-(2,2,2-trifluoroethyl)piperazin-1-yl]imidazo[1,2-b]pyridazine;
2-(4-Fluorophenyl)-3-pyrid-4-yl-6-[4-(2,2,2-trifluoroethyl)piperazin-1-yl]imidazo[1,2-b]pyridazine;
6-(4-Cyclopropylpiperazin-1-yl)-2-(4-fluorophenyl)-3-pyrid-4-ylimidazo[1,2-b]pyridazine;
6-(4-Cyclopropylpiperazin-1-yl)-2-(4-fluorophenyl)-3-(2-methoxypyrid-4-yl)imidazo[1,2-b]pyridazine;
6-(4-Isopropylpiperazin-1-yl)-3-(2-methoxypyrid-4-yl)-2-phenylimidazo[1,2-b]pyridazine;
2-(3-Fluorophenyl)-6-(4-isopropylpiperazin-1-yl)-3-pyrid-4-ylimidazo[1,2-b]pyridazine;
2-(4-Fluorophenyl)-6-(4-isopropylpiperazin-1-yl)-3-pyrid-4-ylimidazo[1,2-b]pyridazine;
2-(4-Fluorophenyl)-6-(4-isopropylpiperazin-1-yl)-3-(2-methoxypyrid-4-yl)imidazo[1,2-b]pyridazine;
2-(3,4-Difluorophenyl)-6-(4-isopropylpiperazin-1-yl)-3-pyrid-4-ylimidazo[1,2-b]pyridazine;
4-[2-(4-Chlorophenyl)-6-(4-isopropylpiperazin-1-yl)imidazo[1,2-b]pyridazin-3-yl]pyrid-2-ylamine;
2-Methyl-1-[4-(2-phenyl-3-pyrid-4-ylimidazo[1,2-b]pyridazin-6-yl)piperazin-1-yl]propan-2-ol;
1-{4-[2-(3-Fluorophenyl)-3-pyrid-4-ylimidazo[1,2-b]pyridazin-6-yl]piperazin-1-yl}-2-methylpropan-2-ol;
1-{4-[2-(4-Fluorophenyl)-3-(2-methoxypyrid-4-yl)imidazo[1,2-b]pyridazin-6-yl]piperazin-1-yl}-2-methylpropan-2-ol;
6-(4-Butylpiperazin-1-yl)-2-(4-chlorophenyl)-3-pyrid-4-ylimidazo[1,2-b]pyridazine;

4-{4-[2-(4-Fluorophenyl)-3-(2-methoxypyrid-4-yl)imi-
  dazo[1,2-b]pyridazin-6-yl]piperazin-1-yl}-2-meth-
  ylbutan-2-ol;
6-(4-Cyclohexylpiperazin-1-yl)-2-(4-fluorophenyl)-3-py-
  rid-4-ylimidazo[1,2-b]pyridazine;
1-{4-[2-(4-Fluorophenyl)-3-pyrid-4-ylimidazo[1,2-b]py-
  ridazin-6-yl]piperazin-1-yl}ethanone;
1-{4-[2-(4-Fluorophenyl)-3-pyrid-4-ylimidazo[1,2-b]py-
  ridazin-6-yl]piperazin-1-yl}-2-methylpropan-1-one;
(±)-2-(4-Fluorophenyl)-6-(hexahydropyrrolo[1,2-a]
  pyrazin-2-yl)-3-pyrid-4-ylimidazo[1,2-b]pyridazine;
2-(4-Fluorophenyl)-6-(S)-hexahydropyrrolo[1,2-a]
  pyrazin-2-yl-3-(2-methoxypyrid-1-4-yl)imidazo[1,2-b]
  pyridazine;
6-((1S,4S)-2,5-Diazabicyclo[2.2.1]hept-2-yl)-2-phenyl-
  3-pyrid-4-ylimidazo[1,2-b]pyridazine;
6-((1S,4S)-5-Benzyl-2,5-diazabicyclo[2.2.1]hept-2-yl)-2-
  (3-fluorophenyl)-3-pyrid-4-ylimidazo[1,2-b]py-
  ridazine;
6-((1S,4S)-2,5-Diazabicyclo[2.2.1]hept-2-yl)-2-(4-fluo-
  rophenyl)-3-pyrid-4-ylimidazo[1,2-b]pyridazine;
6-((1S,4S)-5-Benzyl-2,5-diazabicyclo[2.2.1]hept-2-yl)-2-
  (4-fluorophenyl)-3-pyrid-4-ylimidazo[1,2-b]py-
  ridazine;
6-((1S,4S)-2,5-Diazabicyclo[2.2.1]hept-2-yl)-2-(4-fluo-
  rophenyl)-3-(2-methoxypyrid-4-yl)imidazo[1,2-b]py-
  ridazine;
2-{(1S,4S)-5-[2-(4-Fluorophenyl)-3-(2-methoxypyrid-4-
  yl)imidazo[1,2-b]pyridazin-6-yl]-2,5-diazabicyclo
  [2.2.1]hept-2-yl}ethanol;
2-(4-Fluorophenyl)-6-(5-isopropyl-2,5-diazabicyclo
  [2.2.1]hept-2-yl)-3-(2-methoxypyrid-4-yl)imidazo[1,
  2-b]pyridazine;
2-(4-Fluorophenyl)-6-(4-methyl[1,4]diazepan-1-yl)-3-
  pyrid-4-ylimidazo[1,2-b]pyridazine;
(±)-3-[2-(4-Fluorophenyl)-3-pyrid-4-ylimidazo[1,2-b]py-
  ridazin-6-yl]octahydro(1H)pyrrolo[1,2-d][1,4]diaz-
  epine;
(±)-4-[2-(4-Fluorophenyl)-3-pyrid-4-ylimidazo[1,2-b]py-
  ridazin-6-yl]-1,4-diazabicyclo[3.2.2]nonane;
(±)-4-[2-(3,5-Dimethylphenyl)-3-pyrid-4-ylimidazo[1,2-
  b]pyridazin-6-yl]-1,4-diazabicyclo[3.2.2]nonane;
(±)-3,6-diazabicyclo[3.2.0]hept-3-yl-2-phenyl-3-pyrid-4-
  ylimidazo[1,2-b]pyridazine;
(±)-6-(Hexahydropyrrolo[3,4-b]pyrrol-5(1H)-yl)-2-phe-
  nyl-3-pyrid-4-ylimidazo[1,2-b]pyridazine;
(±)-6-(Hexahydropyrrolo[3,4-b]pyrrol-5(1H)-yl)-3-(2-
  methylpyrid-4-yl)-2-phenylimidazo[1,2-b]pyridazine;
6-Hexahydropyrrolo[3,4-c]pyrrol-2(1H)-yl-2-phenyl-3-
  pyrid-4-ylimidazo[1,2-b]pyridazine;
6-Hexahydropyrrolo[3,4-c]pyrrol-2(1H)-yl-3-(2-meth-
  ylpyrid-4-yl)-2-phenylimidazo[1,2-b]pyridazine;
2-(3-Fluorophenyl)-6-hexahydropyrrolo[3,4-c]pyrrol-2
  (1H)-yl-3-(2-methylpyrid-4-yl)imidazo[1,2-b]py-
  ridazine;
2-(4-Fluorophenyl)-6-hexahydropyrrolo[3,4-c]pyrrol-2
  (1H)-yl-3-pyrid-4-ylimidazo[1,2-b]pyridazine;
2-(4-Fluorophenyl)-6-hexahydropyrrolo[3,4-c]pyrrol-2
  (1H)-yl-3-(2-methylpyrid-4-yl)imidazo[1,2-b]py-
  ridazine;
4-[2-(4-Chlorophenyl)-6-(hexahydropyrrolo[3,4-c]pyr-
  rol-2(1H)-yl)imidazo[1,2-b]pyridazin-3-yl]pyrid-2-
  ylamine;
2-(4-Fluorophenyl)-6-(hexahydropyrrolo[3,4-c]pyrrol-2
  (1H)-yl)-3-(2-methoxypyrid-4-yl)imidazo[1,2-b]py-
  ridazine;
4-[6-(5-Benzylhexahydropyrrolo[3,4-c]pyrrol-2(1H)-7,8-
  dimethyl-2-(4-fluorophenyl)imidazo[1,2-b]pyridazin-
  3-yl]pyrid-2-ylamine;
4-[2-(4-Fluorophenyl)-6-hexahydropyrrolo[3,4-c]pyrrol-
  2(1H)-yl-7,8-dimethylimidazo[1,2-b]pyridazin-3-yl]
  pyrid-2-ylamine;
6-(5-Cyclopropyl hexahydropyrrolo[3,4-c]pyrrol-2(1H)-
  yl)-2-(4-fluorophenyl)-3-pyrid-4-ylimidazo[1,2-b]py-
  ridazine;
2-(4-Fluorophenyl)-6-(5-isopropylhexahydropyrrolo[3,4-
  c]pyrrol-2(1H)-yl)-3-pyrid-4-ylimidazo[1,2-b]py-
  ridazine;
2-(4-Fluorophenyl)-6-(5-isopropylhexahydropyrrolo[3,4-
  c]pyrrol-2-(1H)-yl)-3-(2-methylpyrid-4-yl)imidazo[1,
  2-b]pyridazine;
2-(4-Fluorophenyl)-6-(5-isopropylhexahydropyrrolo[3,4-
  c]pyrrol-2(1H)-yl)-3-(2-methoxypyrid-4-yl)imidazo[1,
  2-b]pyridazine
(±)-6-(Octahydro-6H-pyrrolo[3,4-b]pyrid-6-yl)-2-phe-
  nyl-3-pyrid-4-ylimidazo[1,2-b]pyridazine;
(±)-3-(2-Methylpyrid-4-yl)-6-(octahydro-6H-pyrrolo[3,
  4-b]pyrid-6-yl)-2-phenylimidazo[1,2-b]pyridazine;
(±)-(cis-2-[2-(4-Fluorophenyl)-3-pyrid-4-ylimidazo[1,2-
  b]pyridazin-6-yl]decahydro[2,6]-naphthyridine;
(±)-6-(2,7-Diazaspiro[4.4]non-2-yl)-2-(3-fluorophenyl)-
  3-pyrid-4-ylimidazo[1,2-b]pyridazine;
(±)-6-(2,7-Diazaspiro[4.4]non-2-yl)-2-(4-fluorophenyl)-
  3-pyrid-4-ylimidazo[1,2-b]pyridazine;
(±)-6-(2,8-Diazaspiro[4.5]dec-2-yl)-2-(4-fluorophenyl)-
  3-pyrid-4-ylimidazo[1,2-b]pyridazine;
(±)-6-(2,7-Diazaspiro[4.5]dec-2-yl)-2-(4-fluorophenyl)-
  3-pyrid-4-ylimidazo[1,2-b]pyridazine;
(±)-6-(2,8-Diazaspiro[4.5]dec-8-yl)-2-(4-fluorophenyl)-
  3-pyrid-4-ylimidazo[1,2-b]pyridazine;
(±)-6-(2,7-Diazaspiro[4.5]dec-7-yl)-2-(4-fluorophenyl)-
  3-pyrid-4-ylimidazo[1,2-b]pyridazine;
3-[2-(4-Fluorophenyl)-3-pyrid-4-ylimidazo[1,2-b]py-
  ridazin-6-yl]-3,9-diazaspiro[5.5]undecane;
9-(2-Phenyl-3-pyrid-4-ylimidazo[1,2-b]pyridazin-6-yl)-
  2,9-diazaspiro[5.5]undecane;
9-[3-(2-Methylpyrid-4-yl)-2-phenylimidazo[1,2-b]py-
  ridazin-6-yl]-2,9-diazaspiro[5.5]undecane;
9-[2-(3-Fluorophenyl)-3-(2-methylpyrid-4-yl)imidazo[1,
  2-b]pyridazin-6-yl]-2,9-diazaspiro[5.5]undecane;
9-[2-(4-Fluorophenyl)-3-pyrid-4-ylimidazo[1,2-b]py-
  ridazin-6-yl]-2,9-diazaspiro[5.5]undecane;
9-[2-(4-Fluorophenyl)-3-(2-methylpyrid-4-yl)imidazo[1,
  2-b]pyridazin-6-yl]-2,9-diazaspiro[5.5]undecane;
4-[2-(4-Chlorophenyl)-6-(2,9-diazaspiro[5.5]undec-9-yl)
  imidazo[1,2-b]pyridazin-3-yl]pyrid-2-ylamine;
9-[2-(4-Fluorophenyl)-3-(2-methoxypyrid-4-yl)imidazo
  [1,2-b]pyridazin-6-yl]-2,9-diazaspiro-[5.5]undecane;
2-[2-(4-Fluorophenyl)-3-(pyrid-4-yl)imidazo[1,2-b]py-
  ridazin-6-yl]-2,9-diazaspiro[5.5]undecane
2-[2-(4-Fluorophenyl)-3-(pyrid-4-yl)imidazo[1,2-b]py-
  ridazin-6-yl]-2,8-diazaspiro[5.5]undecane
9-[2-(phenyl)-3-(pyrid-4-yl)imidazo[1,2-b]pyridazin-6-
  yl]-1-oxa-4,9-diazaspiro[5.5]undecane;
9-[2-(4-Fluorophenyl)-3-(pyrid-4-yl)imidazo[1,2-b]py-
  ridazin-6-yl]-1-oxa-4,9-diazaspiro[5.5]undecane;
9-[2-(4-Fluorophenyl)-3-(2-methoxypyrid-4-yl)imidazo
  [1,2-b]pyridazin-6-yl]-1-oxa-4,9-diazaspiro[5.5]unde-
  cane;
4-{[2-(4-Chlorophenyl)-3-(2-methoxypyrid-4-yl)imidazo
  [1,2-b]pyridazin-6-yl]-1-oxa-4,9-diazaspiro[5.5]un-
  dec-9-yl}-2-ylamine;

(±)-{1-[2-(4-Fluorophenyl)-3-pyrid-4-ylimidazo[1,2-b]pyridazin-6-yl]pyrrolidin-3-yl}dimethylamine;
2-(3,5-Dimethylphenyl)-3-pyrid-4-yl-6-(4-pyrrolidin-1-ylpiperid-1-yl)imidazo[1,2-b]pyridazine;
6-(4-Morpholin-4-ylpiperid-1-yl)-2-phenyl-3-pyrid-4-ylimidazo[1,2-b]pyridazine;
6-[4-(2,6-Dimethylmorpholin-4-yl)piperid-1-yl]-2-phenyl-3-pyrid-4-ylimidazo[1,2-b]pyridazine;
{1-[2-(4-Fluorophenyl)-3-pyrid-4-ylimidazo[1,2-b]pyridazin-6-yl]piperid-4-yl}dimethylamine;
2-Phenyl-3-pyrid-4-yl-6-(4-pyrrolidin-1-ylpiperid-1-yl)imidazo[1,2-b]pyridazine;
2-(4-Fluorophenyl)-3-pyrid-4-yl-6-(4-pyrrolidin-1-ylpiperid-1-yl)imidazo[1,2-b]pyridazine;
2-(4-Fluorophenyl)-3-(2-methoxypyrid-4-yl)-6-(4-pyrrolidin-1-ylpiperid-1-yl)imidazo[1,2-b]pyridazine;
(R)-1-{1-[2-(4-Fluorophenyl)-3-pyrid-4-ylimidazo[1,2-b]pyridazin-6-yl]piperid-4-yl}pyrrolidin-3-ol;
6-(4-Morpholin-4-ylpiperid-1-yl)-2-phenyl-3-pyrid-4-ylimidazo[1,2-b]pyridazine;
2-(3-Fluoro-5-methylphenyl)-6-((R)-3-methylpiperazin-1-yl)-3-pyrid-4-ylimidazo-[1,2-b]pyridazine;
{4-[2-(4-Fluorophenyl)-6-((R)-3-methylpiperazin-1-yl)imidazo[1,2-b]pyridazin-3-yl]pyrid-2-yl}methylamine;
6-(3,3-Dimethylpiperazin-1-yl)-2-(4-fluorophenyl)-7-methyl-3-pyrid-4-ylimidazo-[1,2-b]pyridazine;
6-(3,3-Dimethylpiperazin-1-yl)-2-(4-fluorophenyl)-8-methyl-3-pyrid-4-ylimidazo-[1,2-b]pyridazine;
6-(3,3-Dimethylpiperazin-1-yl)-2-(3-fluoro-5-methylphenyl)-3-pyrid-4-ylimidazo-[1,2-b]pyridazine;
{4-[6-(3,3-Dimethylpiperazin-1-yl)-2-(4-fluorophenyl)imidazo[1,2-b]pyridazin-3-yl]pyrid-2-yl}methylamine;
6-((R)-3-Ethylpiperazin-1-yl)-2-(4-fluorophenyl)-3-pyrid-4-ylimidazo[1,2-b]pyridazine;
6-(3,3-Diethylpiperazin-1-yl)-2-(4-fluorophenyl)-3-pyrid-4-ylimidazo[1,2-b]pyridazine;
(±)-6-(3-Fluoromethylpiperazin-1-yl)-2-(4-fluorophenyl)-3-pyrid-4-ylimidazo[1,2-b]pyridazine;
(±)-{(4-[2-(4-Fluorophenyl)-3-pyrid-4-ylimidazo[1,2-b]pyridazin-6-yl]piperazin-2-yl}methanol;
2-{4-[2-(3-Fluoro-5-methylphenyl)-3-pyrid-4-ylimidazo[1,2-b]pyridazin-6-yl]piperazin-1-yl}ethanol;
2-{4-[2-(4-Fluorophenyl)-3-(2-methylaminopyrid-4-yl)imidazo[1,2-b]pyridazin-6-yl]-piperazin-1-yl}ethanol;
1-{4-[2-(4-Fluorophenyl)-3-pyrid-4-ylimidazo[1,2-b]pyridazin-6-yl]piperazin-1-yl}-2-methylpropan-2-ol;
1-{4-[2-(4-Fluorophenyl)-8-methyl-3-pyrid-4-ylimidazo[1,2-b]pyridazin-6-yl]piperazin-1-yl}-2-methylpropan-2-ol;
1-{4-[2-(4-Fluorophenyl)-7-methyl-3-pyrid-4-ylimidazo[1,2-b]pyridazin-6-yl]piperazin-1-yl}-2-methylpropan-2-ol;
1-{4-[2-(4-Fluorophenyl)-3-(2-methylaminopyrid-4-yl)imidazo[1,2-b]pyridazin-6-yl]-piperazin-1-yl}-2-methylpropan-2-ol;
2-{(R)-4-[2-(4-Fluorophenyl)-3-pyrid-4-ylimidazo[1,2-b]pyridazin-6-yl]piperazin-2-yl}propan-2-ol;
2-(4-Fluorophenyl)-6-((R)-3-isopropylpiperazin-1-yl)-3-pyrid-4-ylimidazo[1,2-b]-pyridazine;
{4-[2-(4-Fluorophenyl)-6-((R)-3-isopropylpiperazin-1-yl)imidazo[1,2-b]pyridazin-3-yl]pyrid-2-yl}methylamine;
2-(3-Fluorophenyl)-6-(4-isopropylpiperazin-1-yl)-3-(2-methoxypyrid-4-yl)imidazo-[1,2-b]pyridazine;
2-(4-Fluorophenyl)-6-(4-isopropylpiperazin-1-yl)-7-methyl-3-pyrid-4-ylimidazo[1,2-b]pyridazine;
2-(4-Fluorophenyl)-6-(4-isopropylpiperazin-1-yl)-8-methyl-3-pyrid-4-ylimidazo[1,2-b]pyridazine;
{4-[2-(4-Fluorophenyl)-6-(4-isopropylpiperazin-1-yl)imidazo[1,2-b]pyridazin-3-yl]-pyrid-2-yl}methylamine;
2-(3,4-Difluorophenyl)-6-(4-isopropylpiperazin-1-yl)-3-(2-methoxypyrid-4-yl)imidazo[1,2-b]pyridazine;
2-(3-Fluoro-5-methylphenyl)-6-(4-isopropylpiperazin-1-yl)-3-pyrid-4-ylimidazo[1,2-b]pyridazine;
(±)-6-(3,6-Diazabicyclo[3.2.0]hept-3-yl)-2-phenyl-3-pyrid-4-ylimidazo[1,2-b]pyridazine;
6-(1S,4S)-2,5-Diazabicyclo[2.2.1]hept-2-yl-2-phenyl-3-pyrid-4-ylimidazo[1,2-b]pyridazine;
{4-[(1S,4S)-6-2,5-Diazabicyclo[2.2.1]hept-2-yl-2-(4-fluorophenyl)imidazo[1,2-b]-pyridazin-3-yl]pyrid-2-yl}methylamine;
2-(4-Fluorophenyl)-6-((1S,4S)-5-methyl-2,5-diazabicyclo[2.2.1]hept-2-yl)-3-pyrid-4-ylimidazo[1,2-b]pyridazine;
2-(4-Fluorophenyl)-7-methyl-6-((1S,4S)-5-methyl-2,5-diazabicyclo[2.2.1]hept-2-yl)-3-pyrid-4-ylimidazo[1,2-b]pyridazine;
2-(4-Fluorophenyl)-8-methyl-6-((1S,4S)-5-methyl-2,5-diazabicyclo[2.2.1]hept-2-yl)-3-pyrid-4-ylimidazo[1,2-b]pyridazine;
2-(4-Fluorophenyl)-6-((1S,4S)-5-methyl-2,5-diazabicyclo[2.2.1]hept-2-yl)-3-(2-methylpyrid-4-yl)imidazo[1,2-b]pyridazine;
2-Methyl-1-[(1S,4S)-5-(2-phenyl-3-pyrid-4-ylimidazo[1,2-b]pyridazin-6-yl)-2,5-diazabicyclo[2.2.1]hept-2-yl]propan-2-ol;
6-(3,6-Diazabicyclo[3.1.1]hept-3-yl)-2-(4-fluorophenyl)-3-pyrid-4-ylimidazo[1,2-b]-pyridazine;
2-(4-Fluorophenyl)-6-(5-methyl hexahydropyrrolo[3,4-c]pyrrol-2(1H)-yl)-3-pyrid-4-ylimidazo[1,2-b]pyridazine;
2-(4-Fluorophenyl)-7-methyl-6-(5-methyl hexahydropyrrolo[3,4-c]pyrrol-2(1H)-yl)-3-pyrid-4-ylimidazo[1,2-b]pyridazine;
2-(4-Fluorophenyl)-8-methyl-6-(5-methyl hexahydropyrrolo[3,4-c]pyrrol-2(1H)-yl)-3-pyrid-4-ylimidazo[1,2-b]pyridazine;
2-(4-Fluorophenyl)-8-methyl-6-(5-methyl hexahydropyrrolo[3,4-c]pyrrol-2(1H)-yl)-3-(2-methylpyrid-4-yl)imidazo[1,2-b]pyridazine;
{4-[2-(4-Fluorophenyl)-6-(5-methylhexahydropyrrolo[3,4-c]pyrrol-2(1H)-yl)imidazo-[1,2-b]pyridazin-3-yl]pyrid-2-yl}methylamine;
2-(4-Fluorophenyl)-3-(2-methoxypyrid-4-yl)-6-(5-methyl hexahydropyrrolo[3,4-c]-pyrrol-2(1H)-yl)imidazo[1,2-b]pyridazine;
2-(4-Fluorophenyl)-6-(5-methylhexahydropyrrolo[3,4-c]pyrrol-2(1H)-yl)-3-(2-methylpyrid-4-yl)imidazo[1,2-b]pyridazine;
{4-[2-(4-Fluorophenyl)-8-methyl-6-((3aR,6aS)-5-methylhexahydropyrrolo[3,4-c]-pyrrol-2(1H)-yl)imidazo[1,2-b]pyridazin-3-yl]pyrid-2-yl}methylamine;
{4-[2-(4-Fluorophenyl)-7-methyl-6-(5-methyl hexahydropyrrolo[3,4-c]pyrrol-2(1H)-yl)imidazo[1,2-b]pyridazin-3-yl]pyrid-2-yl}methylamine;
(±)-2-(4-Fluorophenyl)-6-(hexahydropyrrolo[3,4-b]pyrrol-5(1H)-yl)-3-pyrid-4-ylimidazo[1,2-b]pyridazine;
(+)-2-(4-Fluorophenyl)-6-hexahydropyrrolo[3,4-b]pyrrol-5(1H)-yl-3-pyrid-4-ylimidazo[1,2-b]pyridazine;

(−)-2-(4-Fluorophenyl)-6-hexahydropyrrolo[3,4-b]pyrrol-5(1H)-yl-3-pyrid-4-ylimidazo[1,2-b]pyridazine;
(±)-{4-[2-(4-Fluorophenyl)-6-(hexahydropyrrolo[3,4-b]pyrrol-5(1H)-yl)imidazo[1,2-b]-pyridazin-3-yl]pyrid-2-yl}methylamine;
6-(4aS,7aS)-octahydropyrrolo[3,4-b]pyrid-6-yl-2-phenyl-3-pyrid-4-ylimidazo[1,2-b]-pyridazine;
3-(2-Methylpyrid-4-yl)-6-(4aS,7aS)-octahydropyrrolo[3,4-b]pyrid-6-yl-2-phenylimidazo[1,2-b]pyridazine;
3-(2-Methylpyrid-4-yl)-6-(4aR,7aR)-octahydropyrrolo[3,4-b]pyrid-6-yl-2-phenylimidazo[1,2-b]pyridazine;
2-(4-Fluorophenyl)-8-methyl-6-(4aS,7aS)-octahydropyrrolo[3,4-b]pyrid-6-yl-3-pyrid-4-ylimidazo[1,2-b]pyridazine;
2-(4-Fluorophenyl)-7-methyl-6-(4aS,7aS)-octahydropyrrolo[3,4-b]pyrid-6-yl-3-pyrid-4-ylimidazo[1,2-b]pyridazine;
2-(4-Fluorophenyl)-7-methyl-6-(4aR,7aR)-octahydropyrrolo[3,4-b]pyrid-6-yl-3-pyrid-4-ylimidazo[1,2-b]pyridazine;
2-(4-Fluorophenyl)-6-(4aS,7aS)-octahydropyrrolo[3,4-b]pyrid-6-yl-3-pyrid-4-ylimidazo[1,2-b]pyridazine;
2-(4-Fluorophenyl)-3-(2-methylpyrid-4-yl)-6-(4aS,7aS)-octahydropyrrolo[3,4-b]-pyrid-6-ylimidazo[1,2-b]pyridazine;
{4-[2-(4-Fluorophenyl)-6-(octahydropyrrolo[3,4-b]pyrid-6-yl)imidazo[1,2-b]pyridazin-3-yl]pyrid-2-yl}methylamine;
6-(4aR,7aR)-Octahydropyrrolo[3,4-b]pyrid-6-yl-2-phenyl-3-pyrid-4-ylimidazo[1,2-b]pyridazine;
2-(4-Fluorophenyl)-6-(4aR,7aR)-octahydropyrrolo[3,4-b]pyrid-6-yl-3-pyrid-4-ylimidazo[1,2-b]pyridazine;
2-(4-Fluorophenyl)-3-(2-methylpyrid-4-yl)-6-(4aR,7aR)-octahydropyrrolo[3,4-b]-pyrid-6-ylimidazo[1,2-b]pyridazine;
2-(4-Fluorophenyl)-8-methyl-6-(4aR,7aR)-octahydropyrrolo[3,4-b]pyrid-6-yl-3-pyrid-4-ylimidazo[1,2-b]pyridazine;
6-(2,7-Diazaspiro[4.4]non-2-yl)-2-(4-fluorophenyl)-8-methyl-3-pyrid-4-ylimidazo[1,2-b]pyridazine;
6-(6,9-Diazaspiro[4.5]dec-9-yl)-2-(4-fluorophenyl)-3-pyrid-4-ylimidazo[1,2-b]-pyridazine;
(±)-2-[2-(4-Fluorophenyl)-8-methyl-3-pyrid-4-ylimidazo[1,2-b]pyridazin-6-yl]-2,8-diazaspiro[5.5]undecane;
9-[2-(4-Fluorophenyl)-8-methyl-3-pyrid-4-ylimidazo[1,2-b]pyridazin-6-yl]-2,9-diazaspiro[5.5]undecane;
{4-[6-(2,9-Diazaspiro[5.5]undec-9-yl)-2-(4-fluorophenyl)imidazo[1,2-b]pyridazin-3-yl]pyrid-2-yl}methyl amine;
9-[2-(3,4-Difluorophenyl)-3-pyrid-4-ylimidazo[1,2-b]pyridazin-6-yl]-2,9-diazaspiro[5.5]undecane;
9-[2-(3-Fluoro-5-methylphenyl)-3-pyrid-4-ylimidazo[1,2-b]pyridazin-6-yl]-2,9-diazaspiro[5.5]undecane;
2-(3-Fluorophenyl)-3-pyrid-4-yl-6-(4-pyrrolidin-1-ylpiperid-1-yl)imidazo[1,2-b]-pyridazine;
{4-[2-(4-Fluorophenyl)-6-(4-pyrrolidin-1-ylpiperid-1-yl)imidazo[1,2-b]pyridazin-3-yl]pyrid-2-yl}methylamine;
2-(4-Fluorophenyl)-6-[4-((R)-3-fluoropyrrolidin-1-yl)piperid-1-yl]-3-pyrid-4-ylimidazo[1,2-b]pyridazine;
(R)-1-[1-(2-Phenyl-3-pyrid-4-ylimidazo[1,2-b]pyridazin-6-yl)piperid-4-yl]pyrrolidin-3-ol; and
(R)-1-{1-[2-(3-Fluoro-5-methylphenyl)-3-pyrid-4-ylimidazo[1,2-b]pyridazin-6-yl]-piperid-4-yl}-pyrrolidin-3-ol;
or a pharmaceutically acceptable salt of said compound.

8. The method as claimed in claim 6, wherein: $R_2$ represents a phenyl group optionally substituted with one or more substituents selected from the group consisting of halogen atoms and the groups $C_{1-6}$ alkyl, $C_{1-6}$ alkyloxy and $C_{1-6}$ fluoroalkyl.

9. The method as claimed in claim 8, wherein: $R_3$ represents a group selected from the group consisting of a hydrogen atom and a group $C_{1-3}$ alkyl, $C_{1-4}$ alkyloxy and —$NR_4R_5$, and wherein $R_4$ and $R_5$ represent a hydrogen atom or a group $C_{1-4}$-alkyl.

10. The method as claimed in claim 9, wherein: $R_3$ represents a group selected from the group consisting of a hydrogen atom and a methyl and methoxy group.

11. The method as claimed in claim 9, wherein: $R_3$ represents a group selected from the group consisting of —$NH_2$ and dimethylamino.

12. The method as claimed in claim 6, wherein: $R_7$ and $R_8$ represent, independently of each other, a hydrogen atom or a methyl group.

13. The method as claimed in claim 6, wherein: A represents a group $C_{1-7}$-alkylene; B represents a group $C_{1-7}$-alkylene; L represents a carbon substituted with a group $R_{e1}$ and a group $R_d$; wherein $R_d$ represents a hydrogen atom; and $R_d$ represents a group $NR_4R_5$, in which $R_4$ and $R_5$ represent, independently of each other, a group $C_{1-4}$-alkyl; or alternatively $R_{e1}$ represents a pyrrolidinyl, morpholinyl, dimethylmorpholinyl, fluoropyrrolidinyl or hydroxypyrrolidinyl.

14. The method as claimed in claim 6, wherein: A represents a group $C_{1-7}$-alkylene optionally substituted with one or two groups $R_a$; B represents a group $C_{1-7}$-alkylene optionally substituted with a group $R_b$; L represents a nitrogen atom substituted with a group $R_c$ or $R_d$; the carbon atoms of A and B being optionally substituted with one or more groups $R_f$, which may be identical to or different than each other; two groups $R_a$ may together form a group $C_{1-6}$-alkylene; $R_a$ and $R_b$ may together form a bond or a group $C_{1-6}$-alkylene; $R_a$ and $R_c$ may together form a bond or a group $C_{1-6}$-alkylene; $R_b$ and $R_c$ may together form a bond or a group $C_{1-6}$-alkylene; $R_d$ represents a substituent selected from the group consisting of $C_{1-6}$-alkyl, $C_{3-7}$-cycloalkyl, hydroxy-$C_{1-6}$-alkyl, $C_{1-6}$-alkyloxy-$C_{1-6}$-alkyl, $C_{1-6}$-fluoroalkyl, benzyl and $C_1$-$C_6$-alkyl-C(O); and $R_f$ represents a group $C_{1-6}$-alkyl.

15. The method as claimed in claim 6, wherein: A represents a group $C_{1-7}$-alkylene; B represents a group $C_{1-7}$-alkylene; L represents a carbon atom substituted with two groups $R_{e2}$; the carbon atoms of A and B being optionally substituted with one or more groups $R_f$, which may be identical to or different than each other; two groups $R_{e2}$ form, with the carbon atom that bears them, a pyrrolidine, piperidine, or morpholine group; and $R_f$ represents a group $C_{1-6}$-alkyl.

16. The method as claimed in claim 6, wherein: $R_2$ represents a phenyl group optionally substituted with one or more substituents selected from the group consisting of fluorine and chlorine atoms and the methyl group; $R_3$ represents a hydrogen atom; the cyclic amine formed by —N-A-L-B— represents (±)-3-dimethylaminopyrrolidin-1-yl, 4-(pyrrolidin-1-yl)piperid-1-yl, 4-(morpholin-4-yl)piperid-1-yl, 4-(2,6-dimethylmorpholin-4-yl)piperid-1-yl, 4-dimethylaminopiperid-1-yl, 4-(3-hydroxypyrrolidin-1-yl)piperid-1-yl, and 4-(-3-fluoropyrrolidin-1-yl)piperid-1-yl; and $R_7$ and $R_8$ represent a hydrogen atom.

17. The method as claimed in claim 6, wherein: $R_2$ represents a phenyl group optionally substituted with one or more substituents selected from the group consisting of fluorine and chlorine atoms and methyl, methoxy and trifluoromethyl groups; $R_3$ represents a hydrogen atom or a methyl, methoxy, —$NH_2$, methylamino or dimethylamino group; the cyclic amine formed by —N-A-L-B— represents a piperazin-1-yl, 3-methylpiperazin-1-yl, 4-methylpiperazin-1-yl, 3,3-dimethylpiperazin1-yl, 3,4-dimethylpiperazin-1-yl, cis-3,5-dimethylpiperazin-1-yl, 4-(2-hydroxyethyl)piperazin-1-yl, 4-(2-methoxyethyl)piperazin-1-yl, 4-(2-fluoroethyl)piperazin-1-yl, 4-(2,2,2-trifluoroethyl)piperazin-1-yl, cyclopropylpiperazin-1-yl, 4-isopropylpiperazin-1-yl, 4-(2-hydroxy-2-methylpropyl)piperazin-1-yl, 4-n-butylpiperazin-1-yl, 4-(3-hydroxy-3-methylbutyl)piperazin-1-yl, 4-cyclohexylpiperazin-1-yl, 4-acetylpiperazin-1-yl, 4-isobutyrylpiperazin-1-yl, (±)-hexahydropyrrolo[1,2-a]pyrazin-2-yl, (S)-hexahydropyrrolo[1,2-a]pyrazin-2-yl, (1S,4S)-2,5-diazabicyclo[2.2.1]hept-2-yl, (1S,4S)-5-benzyl-2,5-diazabicyclo[2.2.1]hept-2-yl, (1S,4S)-5-(2-hydroxyethyl)-2,5-diazabicyclo[2.2.1]hept-2-yl, 5-isopropyl-2,5-diaza[2.2.1]hept-2-yl, 4-methyl[1.4]diazepan-1-yl, (±)-octahydropyrrolo[1,2-d][1.4]diazepin-2-yl, 1,4-diazabicyclo[3.3.2]non-4-yl, (±)-3,6-diazabicyclo[3.2.0]hept-3-yl, hexahydropyrrolo[3,4-b]pyrrol-5(1H)-yl, hexahydropyrrolo[3,4-c]pyrrol-2(1H)-yl, 5-benzylhexahydropyrrolo[3,4-c]pyrrol-2(1H)-yl, 5-cyclopropylhexahydropyrrolo[3,4-c]pyrrol-2(1H)-yl, 5-isopropylhexahydropyrrolo[3,4-c]pyrrol-2(1H)-yl, octahydro-6H-pyrrolo[3,4-b]pyrid-6-yl or (±)-(cis)-decahydro[2.6]naphthyridin-2-yl, 3-ethylpiperazin-1-yl, 3,3-diethylpiperazin-1-yl, 3-fluoromethylpiperazin-1-yl, 4-(3-hydroxymethyl)piperazin-1-yl, 3-(1-hydroxy-1-methylethyl)piperazin-1-yl, 3-isopropylpiperazin-1-yl, (1R,5R)-3,6-diazabicyclo[3.2.0]hept-2-yl, 5-methyl-2,5-diazabicyclo[2.2.1]hept-2-yl, 1-((1S,4S)-(2,5-diazabicyclo[2.2.1]hept-2-yl)-2-methylpropan-2-ol, 3,6-diazabicyclo[3.1.1]hept-3-yl, 5-methylhexahydropyrrolo[3,4-c]pyrrol-2(1H)-yl, (±)-hexahydropyrrolo[3,4-b]pyrrol-5(1H)-yl, (+)-hexahydropyrrolo[3,4-b]pyrrol-5(1H)-yl, (−)-hexahydropyrrolo[3,4-b]pyrrol-5(1H)-yl, (4aS,7aS)-octahydropyrrolo[3,4-b]pyrid-6-yl, or 6,9-diazaspiro[4.5]dec-9-yl; and $R_7$ and $R_8$ represent, independently of each other, a hydrogen atom or a methyl group.

18. The method as claimed in claim 6, wherein: $R_2$ represents a phenyl group optionally substituted with one or more substituents selected from the group consisting of fluorine and chlorine atoms; $R_3$ represents a hydrogen atom or a methyl, methoxy or —$NH_2$ group; the cyclic amine formed by —N-A-L-B— represents a (±)-2,7-diazaspiro[4.4]non-2-yl, (±)-2,8-diazaspiro[4.5]dec-2-yl, (±)-2,7-diazaspiro[4.5]dec-2-yl, (±)-2,8-diazaspiro[4.5]dec-8-yl, (±)-2,7-diazaspiro[4.5]dec-7-yl, 3,9-diazaspiro[5.5]undec-3-yl, 2,9-diazaspiro[5.5]undec-9-yl, (±)-2,8-diazaspiro[5.5]undec-2-yl or 1-oxa-4,9-diazaspiro[5.5]undec-9-yl; and $R_7$ and $R_8$ represent a hydrogen atom.

19. The method as claimed in claim 6 wherein the circadian rhythm disorder is a sleep disorder related to the circadian rhythm in a patient comprising administering to said patient a therapeutically effective amount of the compound of formula I.

\* \* \* \* \*

UNITED STATES PATENT AND TRADEMARK OFFICE
CERTIFICATE OF CORRECTION

PATENT NO. : 8,846,676 B2
APPLICATION NO. : 13/617678
DATED : September 30, 2014
INVENTOR(S) : Antonio Almario Garcia et al.

It is certified that error appears in the above-identified patent and that said Letters Patent is hereby corrected as shown below:

Title page:

In the Abstract, item (57), line 2, please replace: "imidazo[I,2-b]pyridazine" with --imidazo[1,2-b]pyridazine--.

In the Claims:

At column 69, claim number 1, line numbers 27-28: please replace "$C_{3-7}$-cycloalky, $C_{1-6}$-alkyl, $C_{1,6}$-alkylthio, $C_{1-6}$-alkyl, $C_{1-6}$-alkyloxy, $C_{1-6}$-alkyl" with --$C_{3-7}$-cycloalkyl-$C_{1-6}$-alkyl, $C_{1,6}$-alkylthio-$C_{1-6}$-alkyl, $C_{1-6}$-alkyloxy-$C_{1-6}$-alkyl--;

At column 73, claim number 5, line numbers 51-52: please delete "or salt thereof";

At column 75, claim number 6, line number 47: please replace "$C_{1-8}$-fluoroalkyl" with --$C_{1-6}$-fluoroalkyl--;

At column 76, claim number 6, line numbers 8-10: please replace "selected from the group consisting of a fluorine atom and fluoro $C_{1-6}$-alkyl, $C_{1-6}$-alkyloxy and hydroxyl;" with --chosen from the group consisting of a fluorine atom and the groups $C_{1-6}$-alkyl, $C_{1-6}$-alkyloxy and hydroxyl;--;

At column 80, claim number 7, line numbers 7-9: please replace "6-(5-Cyclopropyl hexahydropyrrolo[3,4-c]pyrrol-2(1H)-yl)-2-(4-fluorophenyl)-3-pyrid-4-ylimidazo[1,2-b]pyridazine" with --6-(5-Cyclopropylhexahydropyrrolo[3,4-c]pyrrol-2(1H)-yl)-2-(4-fluorophenyl)-3-pyrid-4-ylimidazo[1,2-b]pyridazine--;

Signed and Sealed this
Eighth Day of March, 2016

Michelle K. Lee
*Director of the United States Patent and Trademark Office*

CERTIFICATE OF CORRECTION (continued)
U.S. Pat. No. 8,846,676 B2

At column 80, claim number 7, line number 19: please replace "pyridazine" with --pyridazine;--;

At column 82, claim number 7, line numbers 37-39: please replace "2-(4-Fluorophenyl)-6-(5-methyl hexahydropyrrolo[3,4-c]pyrrol-2(1H)-yl)-3-pyrid-4ylimidazo[1,2-b]pyridazine" with --2-(4-Fluorophenyl)-6-(5-methylhexahydropyrrolo[3,4-c]pyrrol-2(1H)-yl)-3-pyrid-4-ylimidazo[1,2-b]pyridazine--;

At column 82, claim number 7, line numbers 40-42: please replace "2-(4-Fluorophenyl)-7-methyl-6-(5-methyl hexahydropyrrolo[3,4-c]pyrrol-2(1H)-yl)-3-pyrid-4-ylimidazo[1,2-b]pyridazine" with --2-(4-Fluorophenyl)-7-methyl-6-(5-methylhexahydropyrrolo[3,4-c]pyrrol-2(1H)-yl)-3-pyrid-4-ylimidazo[1,2-b]pyridazine--;

At column 82, claim number 7, line numbers 43-45: please replace "2-(4-Fluorophenyl)-8-methyl-6-(5-methyl hexahydropyrrolo[3,4-c]pyrrol-2(1H)-yl)-3-pyrid-4-ylimidazo[1,2-b]pyridazine" with --2-(4-Fluorophenyl)-8-methyl-6-(5-methylhexahydropyrrolo[3,4-c]pyrrol-2(1H)-yl)-3-pyrid-4-ylimidazo[1,2-b]pyridazine--;

At column 82, claim number 7, line numbers 46-48: please replace "2-(4-Fluorophenyl)-8-methyl-6-(5-methyl hexahydropyrrolo[3,4-c]pyrrol-2(1H)-yl)-3-(2-methylpyrid-4-yl)imidazo[1,2-b]pyridazine" with --2-(4-Fluorophenyl)-8-methyl-6-(5-methylhexahydropyrrolo[3,4-c]pyrrol-2(1H)-yl)-3-(2-methylpyrid-4-yl)imidazo[1,2-b]pyridazine--;

At column 82, claim number 7, line numbers 52-54: please replace "2-(4-Fluorophenyl)-3-(2-methoxypyrid-4-yl)-6-(5-methyl hexahydropyrrolo[3,4-c]-pyrrol-2(1H)-yl)imidazo(1,2-b]pyridazine" with --2-(4-Fluorophenyl)-3-(2-methoxypyrid-4-yl)-6-(5-methylhexahydropyrrolo[3,4-c]pyrrol-2(1H)-yl)imidazo(1,2-b]pyridazine--;

At column 82, claim number 7, line numbers 61-63: please replace "methyl hexahydropyrrolo[3,4-c]pyrrol-2(1H)-yl)imidazo[1,2-b]pyridazin-3-yl]pyrid-2-yl}methylamine" with --{4-[2-(4-Fluorophenyl)-7-methyl-6-(5-methylhexahydropyrrolo[3,4-c]pyrrol-2(1H)-yl)imidazo[1,2-b]pyridazin-3-yl]pyrid-2-yl}methylamine--;

At column 84, claim number 13, line number 23: please replace "group $R_d$; wherein $R_d$ represents a hydrogen atom; and $R_d$" with --group $R_d$; wherein $R_d$ represents a hydrogen atom; and $R_{e1}$--;

CERTIFICATE OF CORRECTION (continued)
U.S. Pat. No. 8,846,676 B2

At column 84, claim number 16, line number 60: please replace "4-(-3-fluoropyrrolidin-1-yl)piperid-1-yl" with --4-(3-fluoropyrrolidin-1-yl)piperid-1-yl--; and At column 85, claim number 17, line numbers 2-3: please replace "3,3-dimethylpiperazin1-yl" with --3,3-dimethylpiperazin-1-yl--.